(12) United States Patent
Mullen et al.

(10) Patent No.: US 7,784,687 B2
(45) Date of Patent: Aug. 31, 2010

(54) PAYMENT CARDS AND DEVICES WITH DISPLAYS, CHIPS, RFIDS, MAGNETIC EMULATORS, MAGNETIC DECODERS, AND OTHER COMPONENTS

(75) Inventors: Jeffrey David Mullen, Pittsburgh, PA (US); Bruce Cloutier, Pittsburgh, PA (US)

(73) Assignee: Dynamics Inc., Pittsburgh, PA (US)

( * ) Notice: Subject to any disclaimer, the term of this patent is extended or adjusted under 35 U.S.C. 154(b) by 0 days.

(21) Appl. No.: 12/339,055

(22) Filed: Dec. 19, 2008

(65) Prior Publication Data

US 2009/0159688 A1 Jun. 25, 2009

Related U.S. Application Data

(60) Provisional application No. 61/016,491, filed on Dec. 24, 2007, provisional application No. 61/026,846, filed on Feb. 7, 2008, provisional application No. 61/027,807, filed on Feb. 11, 2008, provisional application No. 61/081,003, filed on Jul. 15, 2008, provisional application No. 61/086,239, filed on Aug. 5, 2008, provisional application No. 61/090,423, filed on Aug. 20, 2008, provisional application No. 61/097,401, filed on Sep. 16, 2008, provisional application No. 61/112,766, filed on Nov. 9, 2008, provisional application No. 61/117,186, filed on Nov. 23, 2008, provisional application No. 61/119,366, filed on Dec. 2, 2008, provisional application No. 61/120,813, filed on Dec. 8, 2008.

(51) Int. Cl.
  *G06K 5/00* (2006.01)
(52) U.S. Cl. ..................................................... 235/380
(58) Field of Classification Search .................. 235/380
  See application file for complete search history.

(56) References Cited

U.S. PATENT DOCUMENTS

| | | | |
|---|---|---|---|
| 4,353,064 A | 10/1982 | Stamm | |
| 4,394,654 A | 7/1983 | Hofmann-Cerfontaine | |
| 4,614,861 A | 9/1986 | Pavlov et al. | |
| 4,667,087 A | 5/1987 | Quintana | |
| 4,701,601 A | 10/1987 | Francini et al. | |
| 4,720,860 A | 1/1988 | Weiss | |
| 4,786,791 A | 11/1988 | Hodama | |
| 4,791,283 A | 12/1988 | Burkhardt | |
| 4,797,542 A | 1/1989 | Hara | |
| 5,038,251 A | 8/1991 | Sugiyama et al. | |

(Continued)

FOREIGN PATENT DOCUMENTS

JP            05210770 A            8/1993

(Continued)

OTHER PUBLICATIONS

The Bank Credit Card Business. Second Edition, American Bankers Association, Washington, D.C., 1996.

(Continued)

*Primary Examiner*—Seung H Lee
*Assistant Examiner*—Tae Kim

(57) ABSTRACT

A payment card (e.g., credit and/or debit card) or other card or device (e.g., mobile telephone) is provided with a magnetic emulator operable to communicate data to a magnetic stripe read-head. User interfaces are provided in a number of different configurations in order to achieve a number of different functionalities.

20 Claims, 50 Drawing Sheets

U.S. PATENT DOCUMENTS

| | | |
|---|---|---|
| 5,168,520 A | 12/1992 | Weiss |
| 5,237,614 A | 8/1993 | Weiss |
| 5,276,311 A | 1/1994 | Hennige |
| 5,347,580 A | 9/1994 | Molva et al. |
| 5,361,062 A | 11/1994 | Weiss et al. |
| 5,412,199 A | 5/1995 | Finkelstein et al. |
| 5,434,398 A | 7/1995 | Goldberg |
| 5,434,405 A | 7/1995 | Finkelstein et al. |
| 5,478,994 A | 12/1995 | Rahman |
| 5,479,512 A | 12/1995 | Weiss |
| 5,484,997 A | 1/1996 | Haynes |
| 5,485,519 A | 1/1996 | Weiss |
| 5,585,787 A | 12/1996 | Wallerstein |
| 5,591,949 A | 1/1997 | Bernstein |
| 5,608,203 A | 3/1997 | Finkelstein et al. |
| 5,657,388 A | 8/1997 | Weiss |
| 5,834,756 A | 11/1998 | Gutman et al. |
| 5,856,661 A | 1/1999 | Finkelstein et al. |
| 5,864,623 A | 1/1999 | Messina et al. |
| 5,907,142 A | 5/1999 | Kelsey |
| 5,913,203 A | 6/1999 | Wong et al. |
| 5,937,394 A | 8/1999 | Wong et al. |
| 5,955,021 A | 9/1999 | Tiffany, III |
| 5,956,699 A | 9/1999 | Wong et al. |
| 6,025,054 A | 2/2000 | Tiffany, III |
| 6,045,043 A | 4/2000 | Bashan et al. |
| 6,068,183 A * | 5/2000 | Freeman et al. ............. 235/375 |
| 6,076,163 A | 6/2000 | Hoffstein et al. |
| 6,085,320 A | 7/2000 | Kaliski |
| 6,095,416 A | 8/2000 | Grant et al. |
| 6,130,621 A | 10/2000 | Weiss |
| 6,145,079 A | 11/2000 | Mitty et al. |
| 6,157,920 A | 12/2000 | Jakobsson et al. |
| 6,161,181 A | 12/2000 | Haynes, III et al. |
| 6,176,430 B1 | 1/2001 | Finkelstein et al. |
| 6,182,894 B1 | 2/2001 | Hackett et al. |
| 6,189,098 B1 | 2/2001 | Kaliski |
| 6,199,052 B1 | 3/2001 | Mitty et al. |
| 6,206,293 B1 | 3/2001 | Gutman et al. |
| 6,240,184 B1 | 5/2001 | Huynh et al. |
| 6,241,153 B1 | 6/2001 | Tiffany, III |
| 6,256,873 B1 | 7/2001 | Tiffany, III |
| 6,269,163 B1 | 7/2001 | Rivest et al. |
| 6,286,022 B1 | 9/2001 | Kaliski et al. |
| 6,313,724 B1 | 11/2001 | Osterweil |
| 6,389,442 B1 | 5/2002 | Yin et al. |
| 6,393,447 B1 | 5/2002 | Jakobsson et al. |
| 6,411,715 B1 | 6/2002 | Liskov et al. |
| 6,446,052 B1 | 9/2002 | Juels |
| 6,460,141 B1 | 10/2002 | Olden |
| 6,607,127 B2 | 8/2003 | Wong |
| 6,609,654 B1 | 8/2003 | Anderson et al. |
| 6,631,849 B2 | 10/2003 | Blossom |
| 6,655,585 B2 | 12/2003 | Shinn |
| 6,681,988 B2 | 1/2004 | Stack et al. |
| 6,705,520 B1 | 3/2004 | Pitroda et al. |
| 6,755,341 B1 | 6/2004 | Wong et al. |
| 6,769,607 B1 * | 8/2004 | Pitroda et al. ............... 235/380 |
| 6,769,618 B1 | 8/2004 | Finkelstein |
| 6,805,288 B2 | 10/2004 | Routhenstein et al. |
| 6,811,082 B2 | 11/2004 | Wong |
| 6,813,354 B1 | 11/2004 | Jakobsson et al. |
| 6,817,532 B2 | 11/2004 | Finkelstein |
| 6,873,974 B1 | 3/2005 | Schutzer |
| 6,902,116 B2 | 6/2005 | Finkelstein |
| 6,970,070 B2 | 11/2005 | Juels et al. |
| 6,980,969 B1 | 12/2005 | Tuchler et al. |
| 6,985,583 B1 | 1/2006 | Brainard et al. |
| 6,991,155 B2 | 1/2006 | Burchette, Jr. |
| 7,013,030 B2 | 3/2006 | Wong et al. |
| 7,035,443 B2 | 4/2006 | Wong |
| 7,039,223 B2 | 5/2006 | Wong |
| 7,044,394 B2 | 5/2006 | Brown |
| 7,051,929 B2 | 5/2006 | Li |
| 7,100,049 B2 | 8/2006 | Gasparini et al. |
| 7,100,821 B2 | 9/2006 | Rasti |
| 7,111,172 B1 | 9/2006 | Duane et al. |
| 7,114,652 B2 | 10/2006 | Moullette et al. |
| 7,136,514 B1 | 11/2006 | Wong |
| 7,140,550 B2 | 11/2006 | Ramachandran |
| 7,163,153 B2 | 1/2007 | Blossom |
| 7,195,154 B2 | 3/2007 | Routhenstein |
| 7,197,639 B1 | 3/2007 | Juels et al. |
| 7,219,368 B2 | 5/2007 | Juels et al. |
| 7,225,537 B2 | 6/2007 | Reed |
| 7,225,994 B2 | 6/2007 | Finkelstein |
| 7,246,752 B2 | 7/2007 | Brown |
| 7,298,243 B2 | 11/2007 | Juels et al. |
| 7,337,326 B2 | 2/2008 | Palmer et al. |
| 7,346,775 B2 | 3/2008 | Gasparini et al. |
| 7,356,696 B1 | 4/2008 | Jakobsson et al. |
| 7,357,319 B1 | 4/2008 | Liu et al. |
| 7,359,507 B2 | 4/2008 | Kaliski |
| 7,360,688 B1 | 4/2008 | Harris |
| 7,363,494 B2 | 4/2008 | Brainard et al. |
| 7,380,710 B2 | 6/2008 | Brown |
| 7,398,253 B1 | 7/2008 | Pinnell |
| 7,404,087 B2 | 7/2008 | Teunen |
| 7,424,570 B2 | 9/2008 | D'Albore et al. |
| 7,427,033 B1 | 9/2008 | Roskind |
| 7,454,349 B2 | 11/2008 | Teunen et al. |
| 7,461,250 B1 | 12/2008 | Duane et al. |
| 7,461,399 B2 | 12/2008 | Juels et al. |
| 7,472,093 B2 | 12/2008 | Juels |
| 7,472,829 B2 | 1/2009 | Brown |
| 7,494,055 B2 | 2/2009 | Fernandes et al. |
| 7,502,467 B2 | 3/2009 | Brainard et al. |
| 7,502,933 B2 | 3/2009 | Jakobsson et al. |
| 7,503,485 B1 | 3/2009 | Routhenstein |
| 7,516,492 B1 | 4/2009 | Nisbet et al. |
| 7,523,301 B2 | 4/2009 | Nisbet et al. |
| 7,532,104 B2 | 5/2009 | Juels |
| 7,543,739 B2 | 6/2009 | Brown et al. |
| 7,559,464 B2 | 7/2009 | Routhenstein |
| 7,562,221 B2 | 7/2009 | Nystrom et al. |
| 7,562,222 B2 | 7/2009 | Gasparini et al. |
| 7,580,898 B2 | 8/2009 | Brown et al. |
| 7,584,153 B2 | 9/2009 | Brown et al. |
| 7,591,426 B2 | 9/2009 | Osterweil et al. |
| 7,591,427 B2 | 9/2009 | Osterweil |
| 7,602,904 B2 | 10/2009 | Juels et al. |
| 7,631,804 B2 | 12/2009 | Brown |
| 7,639,537 B2 | 12/2009 | Sepe et al. |
| 7,641,124 B2 | 1/2010 | Brown et al. |
| 7,660,902 B2 | 2/2010 | Graham et al. |
| 2001/0034702 A1 | 10/2001 | Mockett et al. |
| 2001/0047335 A1 | 11/2001 | Arndt et al. |
| 2002/0059114 A1 | 5/2002 | Cockrill et al. |
| 2002/0082989 A1 | 6/2002 | Fife et al. |
| 2002/0096570 A1 | 7/2002 | Wong et al. |
| 2002/0120583 A1 | 8/2002 | Keresman, III et al. |
| 2003/0034388 A1 | 2/2003 | Routhenstein et al. |
| 2003/0052168 A1 | 3/2003 | Wong |
| 2003/0116635 A1 | 6/2003 | Taban |
| 2003/0152253 A1 | 8/2003 | Wong |
| 2003/0163287 A1 | 8/2003 | Vock et al. |
| 2003/0173409 A1 | 9/2003 | Vogt et al. |
| 2003/0179909 A1 | 9/2003 | Wong et al. |
| 2003/0179910 A1 | 9/2003 | Wong |
| 2003/0209608 A1 * | 11/2003 | Blossom .................... 235/492 |
| 2003/0226899 A1 | 12/2003 | Finkelstein |
| 2004/0035942 A1 | 2/2004 | Silverman |
| 2004/0133787 A1 | 7/2004 | Doughty |
| 2004/0162732 A1 | 8/2004 | Rahim et al. |

| | | |
|---|---|---|
| 2004/0172535 A1 | 9/2004 | Jakobsson |
| 2004/0177045 A1 | 9/2004 | Brown |
| 2005/0043997 A1 | 2/2005 | Sahota et al. |
| 2005/0080747 A1 | 4/2005 | Anderson et al. |
| 2005/0086160 A1 | 4/2005 | Wong et al. |
| 2005/0086177 A1 | 4/2005 | Anderson et al. |
| 2005/0116026 A1 | 6/2005 | Burger et al. |
| 2005/0119940 A1 | 6/2005 | Concilio et al. |
| 2005/0154643 A1 | 7/2005 | Doan et al. |
| 2005/0228959 A1 | 10/2005 | D'Albore et al. |
| 2006/0000900 A1 | 1/2006 | Fernandes et al. |
| 2006/0037073 A1 | 2/2006 | Juels et al. |
| 2006/0041759 A1 | 2/2006 | Kaliski et al. |
| 2006/0085328 A1 | 4/2006 | Cohen et al. |
| 2006/0091223 A1 | 5/2006 | Zellner et al. |
| 2006/0161435 A1 | 7/2006 | Atef et al. |
| 2006/0163353 A1 | 7/2006 | Moulette et al. |
| 2006/0174104 A1 | 8/2006 | Crichton et al. |
| 2006/0196931 A1 | 9/2006 | Holtmanns et al. |
| 2006/0256961 A1 | 11/2006 | Brainard et al. |
| 2006/0283958 A1* | 12/2006 | Osterweil ................... 235/492 |
| 2007/0114274 A1 | 5/2007 | Gibbs et al. |
| 2007/0124321 A1 | 5/2007 | Szydlo |
| 2007/0152070 A1 | 7/2007 | D'Albore |
| 2007/0152072 A1 | 7/2007 | Frallicciardi et al. |
| 2007/0153487 A1 | 7/2007 | Frallicciardi et al. |
| 2007/0174614 A1 | 7/2007 | Duane et al. |
| 2007/0192249 A1 | 8/2007 | Biffle et al. |
| 2007/0241183 A1 | 10/2007 | Brown et al. |
| 2007/0241201 A1 | 10/2007 | Brown et al. |
| 2007/0256123 A1 | 11/2007 | Duane et al. |
| 2007/0291753 A1 | 12/2007 | Romano |
| 2008/0005510 A1 | 1/2008 | Sepe et al. |
| 2008/0008315 A1 | 1/2008 | Fontana et al. |
| 2008/0008322 A1 | 1/2008 | Fontana et al. |
| 2008/0010675 A1 | 1/2008 | Massacusa et al. |
| 2008/0016351 A1 | 1/2008 | Fontana et al. |
| 2008/0019507 A1 | 1/2008 | Fontana et al. |
| 2008/0028447 A1 | 1/2008 | O'Malley et al. |
| 2008/0040271 A1 | 2/2008 | Hammad et al. |
| 2008/0040276 A1 | 2/2008 | Hammad et al. |
| 2008/0058016 A1 | 3/2008 | Di Maggio et al. |
| 2008/0059379 A1 | 3/2008 | Ramaci et al. |
| 2008/0096326 A1 | 4/2008 | Reed |
| 2008/0126398 A1 | 5/2008 | Cimino |
| 2008/0128515 A1 | 6/2008 | Di Iorio |
| 2008/0201264 A1 | 8/2008 | Brown et al. |
| 2008/0209550 A1 | 8/2008 | Di Iorio |
| 2008/0288699 A1 | 11/2008 | Chichierchia |
| 2008/0294930 A1 | 11/2008 | Varone et al. |
| 2008/0302877 A1 | 12/2008 | Musella et al. |
| 2009/0013122 A1 | 1/2009 | Sepe et al. |
| 2009/0036147 A1 | 2/2009 | Romano |
| 2009/0046522 A1 | 2/2009 | Sepe et al. |
| 2009/0108064 A1 | 4/2009 | Fernandes et al. |
| 2009/0152365 A1 | 6/2009 | Li et al. |
| 2009/0242648 A1 | 10/2009 | Di Sirio et al. |
| 2009/0244858 A1 | 10/2009 | Di Sirio et al. |
| 2009/0253460 A1 | 10/2009 | Varone et al. |
| 2009/0255996 A1 | 10/2009 | Brown et al. |
| 2009/0290704 A1 | 11/2009 | Cimino |
| 2009/0303885 A1 | 12/2009 | Longo |

FOREIGN PATENT DOCUMENTS

| | | |
|---|---|---|
| WO | WO9852735 | 11/1998 |
| WO | WO0247019 | 6/2002 |
| WO | WO2006066322 | 6/2006 |
| WO | WO2006080929 | 8/2006 |
| WO | WO2008064403 | 6/2008 |

OTHER PUBLICATIONS

A Day in the Life of a Flux Reversal. http://www.phrack.org/issues.html?issue=37&id=6#article. As viewed on Apr. 12, 2010.

Dynamic Virtual Credit Card Numbers. http://homes.cerias.purdue.edu/~jtli/paper/fc07.pdf. As viewed on Apr. 12, 2010.

USPTO, International Search Report, Apr. 28, 2009.

* cited by examiner

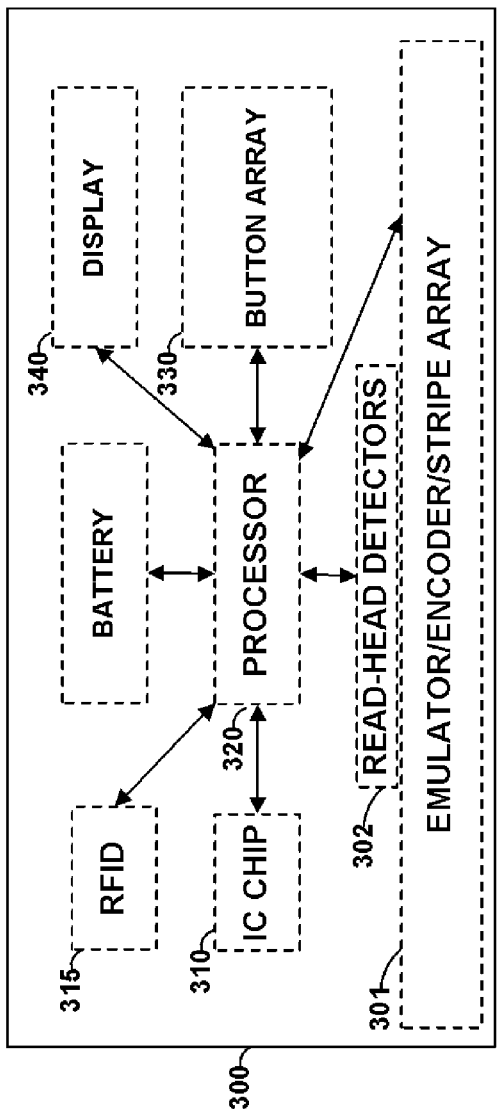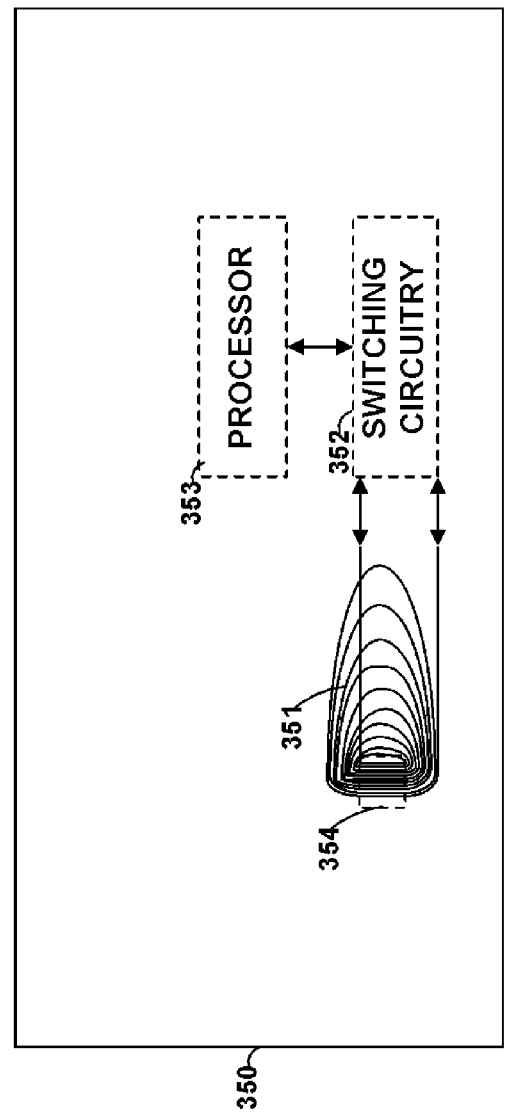
FIG. 3

US 7,784,687 B2

PAYMENT CARDS AND DEVICES WITH DISPLAYS, CHIPS, RFIDS, MAGNETIC EMULATORS, MAGNETIC DECODERS, AND OTHER COMPONENTS

CROSS-REFERENCE TO RELATED APPLICATIONS

This application claims the benefit of U.S. Provisional Patent Application Nos. 61/016,491 filed on Dec. 24, 2007, 61/026,846 filed on Feb. 7, 2008, 61/027,807 filed on Feb. 11, 2008, 61/081,003 filed on Jul. 15, 2008, 61/086,239 filed on Aug. 5, 2008, 61/090,423 filed on Aug. 20, 2008, 61/097,401 filed Sep. 16, 2008, 61/112,766 filed on Nov. 9, 2008, 61/117,186 filed on Nov. 23, 2008, 61/119,366 filed on Dec. 2, 2008, and 61/120,813 filed on Dec. 8, 2008, all of which are hereby incorporated by reference herein in their entirety.

BACKGROUND OF THE INVENTION

This invention relates to magnetic cards and payment systems.

SUMMARY OF THE INVENTION

A card is provided, such as a credit card or security card, that may transmit information to a magnetic stripe reader via a magnetic emulator. The magnetic emulator may be, for example, a circuit that emits electromagnetic fields operable to electrically couple with a read-head of a magnetic stripe reader such that data may be transmitted from the circuit to the magnetic stripe reader. The emulator may be operated serially such that information is transmitted serially to a magnetic stripe reader. Alternatively, for example, portions of a magnetic emulator may emit different electromagnetic fields at a particular instance such that the emulator is operated to provide physically parallel, instantaneous data. Alternatively still, a magnetic medium may be provided and a circuit may be provided to change the magnetic properties of the magnetic medium such that a magnetic stripe reader is operable to read information written on the magnetic medium.

A processor may be provided on a card, or other device, that controls a magnetic emulator. The processor may be configured to operate the emulator such that the emulator transmits serial or parallel information. Particularly, the processor may decouple portions of an emulator from one another such that different portions of the emulator may transmit different information (e.g., transmit data in a parallel operation). The processor may couple portions of an emulator together (or drive the portions together) such that all portions of the emulator transmits the same information (e.g., transmit data in a serial operation). Alternatively, the processor may drive a portion of the emulator to transmit data using one method (e.g., serially) while the processor drives another portion of the emulator using a different method (e.g., in parallel).

The processor may drive an emulator through a switching circuit. The switching circuit may control the direction and magnitude of current that flows through at least a portion of an emulator such that the switching circuit controls the direction and magnitude of the electromagnetic field created by at least that portion of the emulator. An electromagnetic field may be generated by the emulator such that the emulator is operable to electrically couple with a read-head from a magnetic stripe reader without making physical contact with the read-head. Particularly, for example, an emulator that is driven with increased current can be operable to couple with the read-head of a magnetic stripe reader even when placed outside and within the proximity of (e.g., 0.25 inches or more) the read-head.

A processor may detect, for example, the presence of a read-head of a magnetic stripe reader by receiving signals from a magnetic stripe reader detector and, in response, the processor may drive a magnetic emulator in a manner that allows the emulator to couple with the magnetic stripe reader. More than one emulator may be provided on a card or other device and a processor may drive such emulators in a variety of different manners.

A circuit may be provided on a credit card that is operable to receive data from a device, such as a magnetic stripe. In this manner, a card, or other device, may communicate bi-directionally with a device.

An emulator may communicate with a magnetic stripe reader outside of, for example, the housing of a magnetic stripe reader. Accordingly, for example, the emulator may be provided in devices other than cards sized to fit inside of the reading area of a magnetic stripe reader. In other words, for example, the emulator may be located in a device that is thicker than a card—yet the emulator can still communicate with one or more read-heads located in a magnetic stripe reader. Such a device may be, for example, a security token, a wireless communications device, a laptop, a Personal Digital Assistant (PDA), a physical lock key to a house and/or car, or any other device.

Dynamic information may be provided by a processor located on the card, or other device, and communicated through a magnetic emulator. Such dynamic information may, for example, change based on time. For example, the dynamic information may be periodically encrypted differently. One or more displays may be located on a card, or other device, such that the dynamic information may be displayed to a user through the display. Buttons may be provided to accept input from a user to, for example, control the operation of the card or other device.

Dynamic information may include, for example, a dynamic number that is used as, or part of, a number for a credit card number, debit card number, payment card number, and/or payment verification code. Dynamic information may also include, for example, a student identification number or medical identification number. Dynamic information may also, for example, include alphanumeric information such that a dynamic account name is provided.

Read-head detectors may be provided to determine, for example, when a card is being swiped and/or when a read-head is located over a particular portion of a card (e.g., a magnetic emulation circuit). A magnetic emulation circuit may be provided as, for example, a coil. Portions of such a coil may be utilized to detect a read-head while in other portions of the coil may be utilized to communicate information electromagnetically to a read-head. Accordingly, a coil may be utilized to detect a read-head and, after a read-head is detected, the coil may be utilized to, for example, serially transmit information to a magnetic stripe reader.

A read-head detector, or an array of read-head detectors, may be able to, for example, determine the type of reader that the card entered into. For example, a read-head detector array may determine, for example, when a motorized reader was utilized, an insertion reader was utilized, or a user-swipe reader was utilized. Such information may be stored and communicated to a remote storage device (e.g., a remote database). This stored information may be utilized to combat, for example, card cloning. For example, if a particular number of cards (e.g., 10 more) that made consecutive purchases from a machine (e.g., an ATM) detected more than one reader, then, for example, the system may make an autonomous determination that an illegal cloning device was located on front of that ATM machine. If, for example, multiple cards use a restaurant point-of-sale terminal and determine that multiple readers were used then, for example, a computer can make an autonomous determination that cloning may have occurred at the restaurant.

A material may be sandwiched between the two layers to assist in reducing the effect of the electromagnetic fields from one set of coil segments on the side of the material opposite that set of coil segments. Such an interior material may be insulated such that the material does not short the coil segments. Additionally, such an interior material may be chosen, for example, such that the material does not saturate when the coil is conducting current. The coil and material may run, for example, along the location of a track of magnetic data for a payment card. Accordingly, a coil may be fabricated so that the coil wraps around an interior material.

A material may be placed and/or printed on a PCB layer and sandwiched between two other PCB layers. These two other layers may each include coil segments and vias. The middle layer may also include vias such that the material is fabricated to be located in the center of the coil. The material may take a cylindrical, rectangular, square, or any type of shape. Four layers may also be utilized, where the coil segments are printed on a surface of the exterior layers and one or more materials are printed and/or placed on/between the interior layers. A material may be a magnetic material, ferromagnetic material, ferrimagnetic material, or any type of material. For example, copper may be printed on a PCB layer and plated with a material (e.g., nickel, iron, chrome, tin, gold, platinum, cobalt, zinc, alloys). A material, for example, may have a relative permeability multiple times greater than the permeability of a vacuum. A material, for example, may have a relative permeability of 2 to 25,000. A material may include, for example, a permalloy, iron, steel, ferrite, nickel or any other material. A material may be an alloy such as a nickel-iron alloy. Such a nickel-iron alloy may include, for example, nickel (e.g., 75-85%), iron, copper, molybdenum and may be placed through one or more annealing processes. Annealing may occur before and/or after the material is placed/printed on a layer of material (e.g., a PCB layer or other layer). A similar and/or different material may be placed either above and/or below a portion, or the entire, set of paths on a layer for a coil. Accordingly, for example, a material may be placed in the interior of a coil as well as along a side of the coil.

Displays may be provided near user interfaces or other structures. For example, a display may be provided next to an LED. Cards may be programmed during manufacturing so that these displays may display particular information. Accordingly, for example, the same card architecture may be utilized to provide a number of different types of cards. A user may utilize user interfaces (e.g., mechanical or capacitive interfaces) to change the function of the display. For example, codes may be entered to reconfigure the displays. Alternatively, for example, a user may utilize buttons to select information to be displayed on displays associated with user interfaces. A code may associate a name of a store with a button and/or a dollar amount. For example, a display may be configured to read "Target $50." Information may be entered manually, but also may be received by a card. For example, a user may swipe a card a second time through a magnetic stripe reader and receive information via a magnetic emulator. This received information may be utilized to update information on the card (e.g., the balance of a gift card, credit account, and/or debit account). Information may also be received by an RFID antenna and/or IC chip located on a card and in communication with a central processor (or distributed processors). For example, transaction information (e.g., list of past transactions, stores where transactions occurred, amounts of transactions) and account information (e.g., balance information, bill information, amount due information) may be communicated to the card and displayed on one or more displays.

A dynamic card may be manufactured in a variety of ways. For example, a dynamic card may be printed onto a flexible material (e.g., a flexible polymer). Multiple layers of this material may be bonded together to form a multiple layer flexible structure. This multiple layer structure may be laminated (e.g., via hot, warm and/or cold lamination) to form a card. The card may be programmed before or after lamination. A card may be programmed via a direct connection between a programmer and one or more contacts on a card. A card may be programmed via a capacitive, optical, or inductive communication via a communication link between a programmer and one or more components (e.g., a contact) on a card. Accordingly, for example, a card may be laminated and capacitively, optically, or inductively programmed. After programming, a processor on the card may be signaled to burn-out its programming communication channel(s) such that no further programming may occur. A portion of the card may not be laminated. Accordingly, a programmer may connect to this non-laminated portion of the card. The non-laminated portion of the card may be laminated after programming. Alternatively, for example, the non-laminated portion of the card may be cut after programming (e.g., and after the processor burns-out its programming ports so the processor cannot be further programmed).

Additional external communication devices may be provided on a card. For example, a USB port or Wi-Fi antenna may be provided on a card. Such additional external communication devices may, for example, allow a user to communicate with stationary computer, laptop, or other device. Such communication devices may, for example, be utilized to load gift cards, or other information (e.g., transactional or account information) from a laptop to a card or other device. A card is provided that includes a light sensor such that information can be communicated to a card via light (e.g., via a light transmitted from a TV or website).

Components of card may be oriented in a number of ways in order to increase the whimsical and festive nature of a card. Furthermore, the orientation of components may increase the functionality of a card. For example, buttons may be placed on the left-side of a card, but left-handed and right-handed users may naturally operate such buttons differently. Furthermore, buttons may be provided on the center of the card in order to increase the operational similarity of the buttons between left and right-handed users.

Numerous components may be placed on the front or back of a card or other device (e.g., a mobile telephonic device). For example, any number of displays, user interfaces such as buttons, sources of light such as LEDs, vibrational devices, sources of audible signals, microphones, power generating devices, sources of electrical energy, RFID antennas, processors, IC chips, or magnetic communication devices (e.g., magnetic emulators and encoders) may be provided on a card.

Indicia may be provided on the front and back of a card in order to increase the whimsical and festive nature of the card. Such indicia may also increase the functionality of a card. For example, a button may include a written letter (e.g., "A") and multiple numbers (e.g., "0" and "1"). Accordingly, a user may be issued with a letter or numerical PIN number and may utilize the same set of buttons regardless of whether the user received a numerical PIN or a letter-based PIN. In doing so, for example, a ten digit PIN may be represented by less than 10 buttons.

BRIEF DESCRIPTION OF THE DRAWINGS

The principles and advantages of the present invention can be more clearly understood from the following detailed description considered in conjunction with the following drawings, in which the same reference numerals denote the same structural elements throughout, and in which:

FIG. 3 is an illustration of cards constructed in accordance with the principles of the present invention;

DETAILED DESCRIPTION OF THE INVENTION

Figure 1:
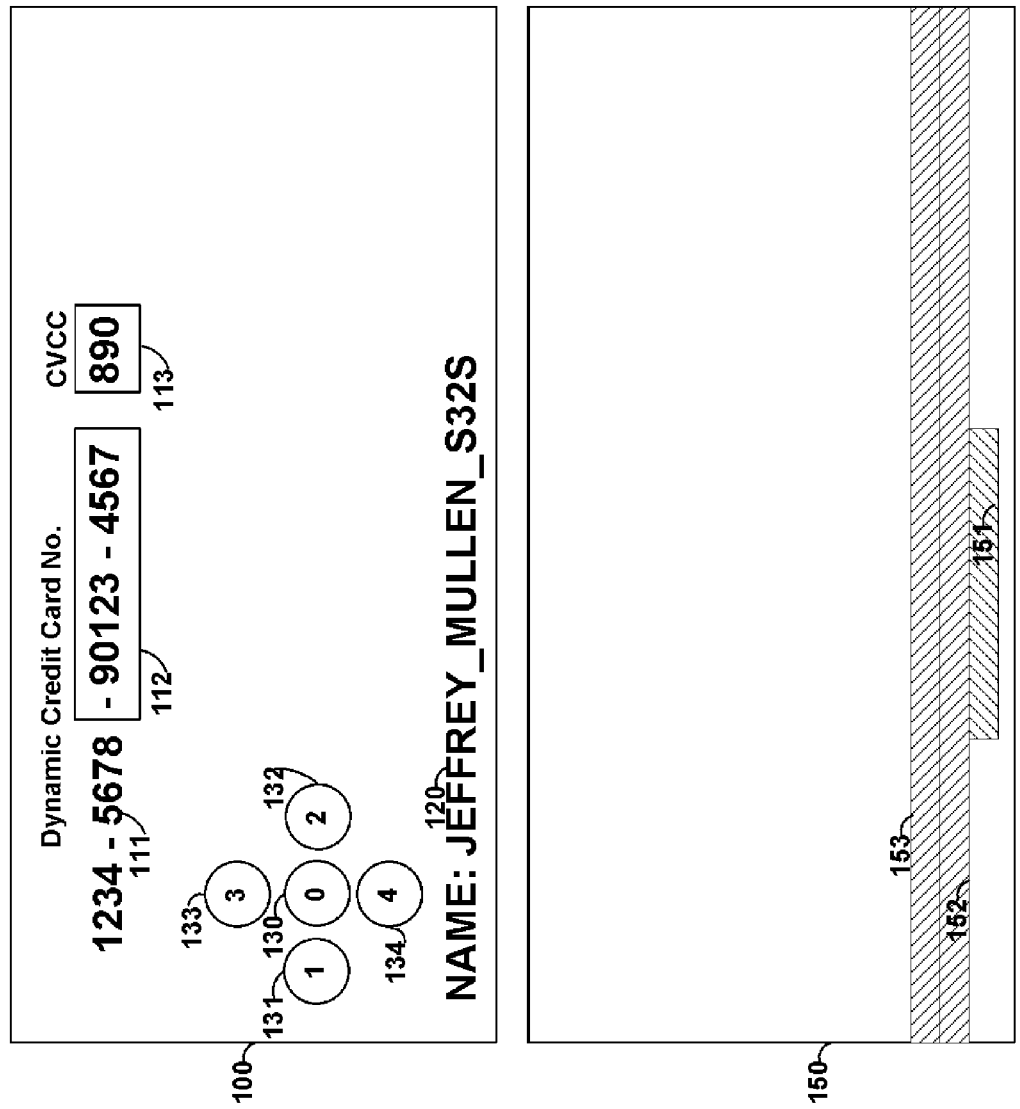
FIG. 1 is an illustration of cards constructed in accordance with the principles of the present invention.

FIG. 1 shows card 100 that includes printed information 111 and 120, displays 112 and 113, and buttons 130-134. Card 100 may be, for example, a payment card such as a credit card, debit card, and/or gift card or other card (e.g., security access or identification card). Payment information, such as a credit/debit card number may be provided as static information 111, dynamic information 112 and/or 113, or any combination thereof.

For example, a particular number of digits of a credit card number (e.g., the last 3 digits) may be provided as dynamic information. Such dynamic information may be changed periodically (e.g., once every hour). Information may be changed via, for example, encryption. Software may be provided at, for example, the payment verification server that verifies the dynamic information for each period of time such that a payment can be validated and processed for a particular user. A user may be identified using, for example, static information that is used to form a credit card number or other static information (e.g., information 120). Additionally, identification information may be derived (e.g., embedded) in dynamic information. Persons skilled in the art will appreciate that a credit card number may have, for example, a length of 15 or 16 digits. A credit card number may also have a length of up to 19 digits. A verification code may be used with some payment systems and such a verification code may be provided statically on the card or may be provided as dynamic information. Such a verification code may be provided on a second display located on, for example, the front or rear surface of card 100. Alternatively, a verification code may be displayed on the same display as other dynamic information (e.g., dynamic information 112). A display may be, for example, a flexible electronic ink display. Such a flexible electronic ink display may, for example, utilize power to change displayed information, but may not utilize power to display information after the information is changed.

Card 150 may be provided. Card 150 may include static magnetic stripe tracks 153 and 152. Magnetic emulator 151 may be included and may be operable to electrically couple with a read-head of a magnetic stripe reader. Persons skilled in the art will appreciate that a read-head housing of a magnetic stripe reader may be provided with one, two, or three active read-heads that are operable to each couple with a separate magnetic track of information. A reader may also have more than one read-head housing and each read-head housing may be provided with one, two, or three active read-heads that are operable to each couple with a separate magnetic track of information. Such read-head housings may be provided different surfaces of a magnetic stripe reader. For example, the read-head housings may be provided on opposite walls of a trough sized to accept payment cards. Accordingly, the devices on the opposite sides of the trough may be able to read a credit card regardless of the direction that the credit card was swiped.

A magnetic emulator may be provided and may be positioned on card 150 such that when card 150 is swiped through a credit card reader, the magnetic emulator passes underneath, or in the proximity of, a read-head for a particular magnetic track. An emulator may be large enough to simultaneously pass beneath, or in the proximity of, multiple read-heads. Information may be transmitted, for example, serially to one or more read-heads. Information from different tracks of data may also be transmitted serially and the magnetic stripe reader may determine the different data received by utilize the starting and/or ending sentinels that define the information for each track. A magnetic emulator may also transmit a string of leading and/or ending zeros such that a magnetic reader may utilize such a string of zeros to provide self-clocking. In doing so, for example, information may be transmitted serially at high speeds to a magnetic stripe reader. For example, credit card information may be transmitted to a magnetic stripe reader at speeds up to, and greater than, 30 kHz.

Different emulators may be provided, and positioned, on card 150 to each couple with a different read-head and each emulator may provide different track information to those different read-heads. Read-head detectors may be utilized to detect when a read-head is over an emulator such that an emulator is controlled by a processor to operate when a read-head detector detects the appropriate presence of a read-head. In doing so, power may be saved. Additionally, the read-head detector may detect how many read-heads are reading the card and, accordingly, only communicate with the associated emulators. In doing so, additional power may be conserved. Accordingly, an emulator may be utilized to communicate dynamic information to a magnetic stripe reader. Such dynamic information may include, for example, dynamic payment card information that changes based on time.

A static magnetic stripe may be provided to transmit data for one or more tracks to a magnetic strip reader where dynamic information is not desired. Card 150, for example, may include static magnetic track 153 and static magnetic track 152. Information on static magnetic tracks 152 and 153 may be encoded via a magnetic stripe encoder. Emulator 151 may be included such that dynamic information may be communicated to a magnetic stripe reader, for example, without a magnetic stripe via an electromagnetic signal transmitted directly from emulator 151 to a read-head of a magnetic stripe reader. Any combination of emulators and static magnetic tracks may be utilized for a card or device (e.g., two magnetic emulators without any magnetic stripes).

One or more batteries, such as flexible lithium polymer batteries, may be utilized to form card 100. Such batteries may be electrically coupled in a serial combination to provide a source of power to the various components of card 100. Alternatively, separate batteries may provide power to different components of card 100. For example, a battery may provide power to a processor and/or display of card 100, while another battery provides a source of energy to one or more magnetic emulators of card 100. In doing so, for example, a processor may operate even after the battery that supplies power to an emulator completely discharges. Accordingly, the processor may provide information to another component of card 100. For example, the processor may display information on a display to indicate to a user that the magnetic emulator is not longer operational due to power exhaustion. Batteries may be, for example, rechargeable and contacts, or other devices, may be provided on card 100 such that the battery may be recharged.

Buttons (e.g., buttons 130-134) may be provided on a card. Such buttons may allow a user to manually provide information to a card. For example, a user may be provided with a personal identification code (e.g., a PIN) and such a personal identification code may be required to be manually inputted into a card using the buttons in order for the card to operate in a particular manner. For example, the use of a magnetic emulator or the use of a display may require a personal identification code.

By dynamically changing a portion of a user's credit card number, for example, credit card fraud is minimized. By allowing the dynamic information to displayed visually to a user, and changed magnetically on a card, user behavior change is minimized (with respect to a credit card with completely static information). By requiring the use of a personal identification code, the fraud associated with lost or stolen credit cards is minimized. Fraud associated with theft/loss is minimized as third party users do not know the personal identification code needed to operate particular aspects of a credit card with dynamic information.

Figure 2:
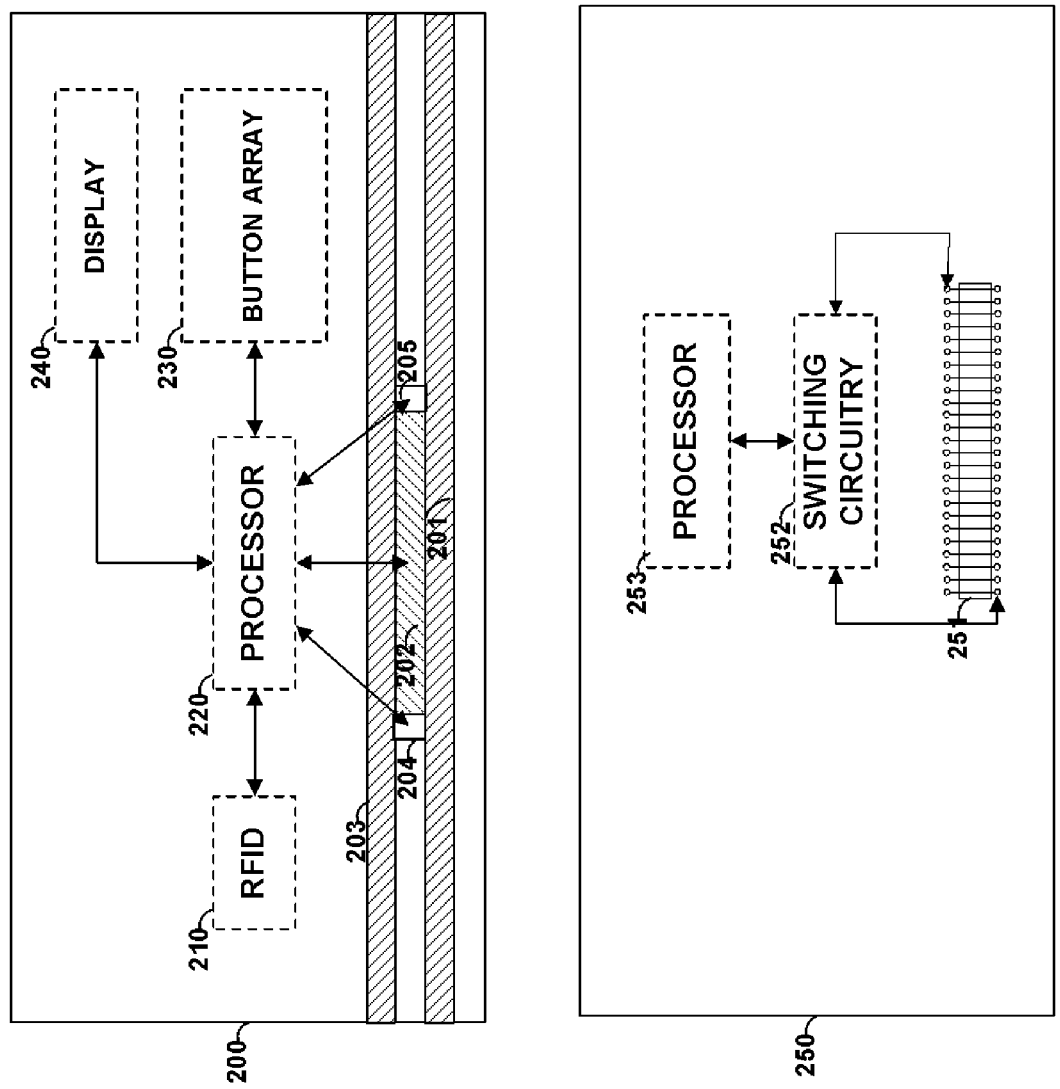
FIG. 2 is an illustration of cards constructed in accordance with the principles of the present invention.

FIG. 2 shows card 200. Card 200 may include, for example, static magnetic stripe track 203, static magnetic stripe track 201, and magnetic emulator 202 sandwiched between read-head detectors 204 and 205. A read-head detector may, for example, be provided as a circuit that detects, for example, changes in capacitance or mechanical coupling to a conductive material. Processor 220 may be provided to, for example, receive information from read-head detectors 204 and 205 and control emulator 202. Persons skilled in the art will appreciate that processor 220 may cause a current to flow through a coil of emulator 202 in a different direction to produce different electromagnetic fields. The transitions between the different electromagnetic fields may be sensed by a magnetic stripe reader as information. Accordingly, a magnetic emulator may transmit data serially while a read-head is electrically coupled with a magnetic reader.

RFID antenna 210 may be provided on card 200. Such an RFID antenna may be operable to transmit information provided by processor 220. In doing so, for example, processor 220 may communicate with an RFID device using RFID antenna 210 and may communicate with a magnetic stripe reader using magnetic emulator 202. Both RFID antenna 210 and magnetic emulator 202 may be utilized to communicate payment card information (e.g., credit card information) to a reader. Processor 240 may also be coupled to display 240 such that dynamic information can be displayed on display 240. Button array 230 may also be coupled to processor 220 such that the operation of card 200 may be controlled, at least in part, by manual input received by button array 230. A smart-card chip may, for example, be included on card 200 in lieu of, or in addition to, RFID 210.

Persons skilled in the art will appreciate that a static magnetic track may be a read-write track such that information may be written to a magnetic track from a magnetic stripe reader that includes a head operable to magnetically encode data onto a magnetic track. Information may be written to a magnetic track as part of a payment process (e.g., a credit card or debit card transaction). Persons skilled in the art will appreciate that a static magnetic track may include a magnetic material that includes ferromagnetic materials that provide for flux-reversals such that a magnetic stripe reader can read the flux-reversals from the static magnetic track. Persons skilled in the art will also appreciate that a magnetic emulator may communicate information that remains the same from payment card transaction to payment card transaction (e.g., static information) as well as information that changes between transactions (e.g., dynamic information).

A card may include magnetic emulators without, for example, including a static magnetic track. Read-head detectors may also be provided. Persons skilled in the art will appreciate that a magnetic reader may include the ability to read two tracks of information (e.g., may include at least two read-heads). All of the information needed to perform a financial transaction (e.g., a credit/debit card transaction) may be included on two magnetic tracks. Alternatively, all of the information needed to perform a financial transaction (e.g., a gift card transaction) may be included on one magnetic track. Accordingly, particular cards, or other devices, may include the ability, for example, to only transmit data associated with the tracks that are needed to complete a particular financial transaction. Persons skilled in the art will appreciate that for systems with three tracks of information, the bottom two tracks may be utilized for credit card information. Persons skilled in the art will also appreciate that a secure credit card transaction may be provided by only changing, for example, one of two magnetic tracks utilized in a credit card transaction (for those transactions that utilize two tracks). Accordingly, one track may be a static magnetic track constructed from a magnetic material and the other track may be provided as a magnetic emulator. Persons skilled in the art will also appreciate that numerous additional fields of data may be provided on a magnetic track in addition to a credit card number (or a security code). Dynamic information may be provided in such additional fields in order to complete a particular financial transaction. For example, such additional dynamic information may be numbers (or characters), encrypted with time and synced to software, at a validating server, operable to validate the encrypted number for a particular period of time.

Card 250 includes emulator 251 that includes a coil operable to communicate data serially to a magnetic stripe reader. Similarly, for example, emulator 251 may receive information for a magnetic stripe encoder. Persons skilled in the art will appreciate that a coil may run across the length of a card such that a read-head moves along the length of the coil and can receive information transmitted serially from the coil. The coil may extend into multiple tracks such that multiple read-heads receive information from the coil. Track information can be sent serially (e.g., track 1 information followed by track 2 information). Multiple coils may be driven separately and placed in different zones such that a single read-head moves from coil-to-coil (e.g., zone-to-zone) and power is conserves as only coils in a particular zone (or zones) may be utilized to communicate information any particular time. Separate coils may be utilized for separate tracks. Materials may be placed in the interior of each coil to assist with manipulating the electromagnetic field produced by the coils. Material may be placed above or below a coil to further manipulate the electromagnetic field produced by the coil.

Switching circuitry 252 may include, for example, one or more transistors that may be utilized to control the direction of current via emulator 251 (e.g., the polarity of voltage(s) across a drive resistor). For example, a coil may be utilized to transmit a string of information to a particular read-head. Different coils may transmit information at different speeds (or at the same speed). Different coils may transmit different amounts of information. For example, three coils may be provided. The coil closest to the bottom of the long-end of a card may transmit at least 79 characters. The coil next closest to the bottom of the long-end of a card may transmit at least 40 characters of information. The coil next closest to the bottom of the long-end of the card may transmit at least 107 characters. One or more coils may have different character sets (e.g., a 6-bit character set or a 7-bit character set). The last bit in a character may include, for example, a parity bit. Additional synching information may be transmitted before and after the data information to assist with synching a magnetic stripe reader. For example, a string of zeros may be communicated before and after communicating primary data. Characters may be included in the data information for other purposes such as an LRC character.

FIG. 3 shows card 300 that may include a number of components. Card 300 may include one or more processors 320. A processor may include, for example, cache memory, RAM, and/or ROM. Additional memory may be provided on card 300. For example, additional non-volatile, volatile, cache memory, RAM, and/or ROM may be provided on card 300. Battery 325 may be provided on card 300. Battery 325 may be, for example, a lithium polymer battery and may have a thickness less than a millimeter (e.g., approximately 0.5 mm). RFID antenna 315 may be provided on card 300 and may communicate data to an RFID reader. Persons skilled in the art will appreciate that an RFID may be included that is a passive or active RFID. IC chip 310 may be included on card 300 and may communicate data to an IC chip reader. Device 301 may be included to communication information to a magnetic stripe reader. Device 301 may include any number of magnetic emulators, magnetic encoders that encode magnetic stripes, and/or magnetic stripes. For example, device 301 may include a magnetic emulator for one track of magnetic data and a magnetic stripe for a second track of data. Alternatively, for example, device 301 may include two emulators for separate tracks of data. An emulator may, for example, communicate information to a read-head of a magnetic stripe reader serially. One or more read-head detectors 302 may be provided to detect a read-head (or other attribute) of a magnetic stripe reader. Additional detectors may be included to detect, for example, when a card is provided into an IC chip reader and/or an electromagnetic field from an RFID reader. Button array 330 may be provided, for example, to receive input from a user. Button array 330 may include any number of buttons (e.g., 4, 5, 10, or more than 10). Button array 330 may include, for example, mechanical buttons, capacitive buttons, or any type of user interface. One or more displays 340 may also be included. A display may be, for example, an electronic ink display (e.g., electrochromic display), LCD display, or any other type of display. Display 340 may be flexible.

Display 340 may be printed onto a layer during a printed fabrication process (e.g., PCB). Additionally, for example, battery 325 may be printed onto a layer during a printed fabrication process (e.g., PCB). Similarly, a magnetic emulator may be printed onto a layer during a printed fabrication process (e.g., PCB). Other components may be printed onto a layer during a printed fabrication process (e.g., PCB) such as capacitive read-head detectors, and capacitive touch sensors.

Accordingly, a display, battery, read-head detector, and button array may be printed on one or more layers that are bonded together and laminated.

FIG. 3 shows card 350 that may include, for example, processor 353, switching circuitry 352, and emulator 351 having active region 354. Switching circuitry 352 may, for example, control the direction of current through emulator 351 in order to change the direction of electromagnetic fields generated by emulator 351 such that data may be communicated serially to a magnetic stripe read-head. Persons skilled in the art will appreciate that emulator 351 may be fabricated on a single layer and that region 354 may include coil segments dense enough to generate an electromagnetic field that can be recognized by a read-head of a magnetic stripe reader.

Figure 4:
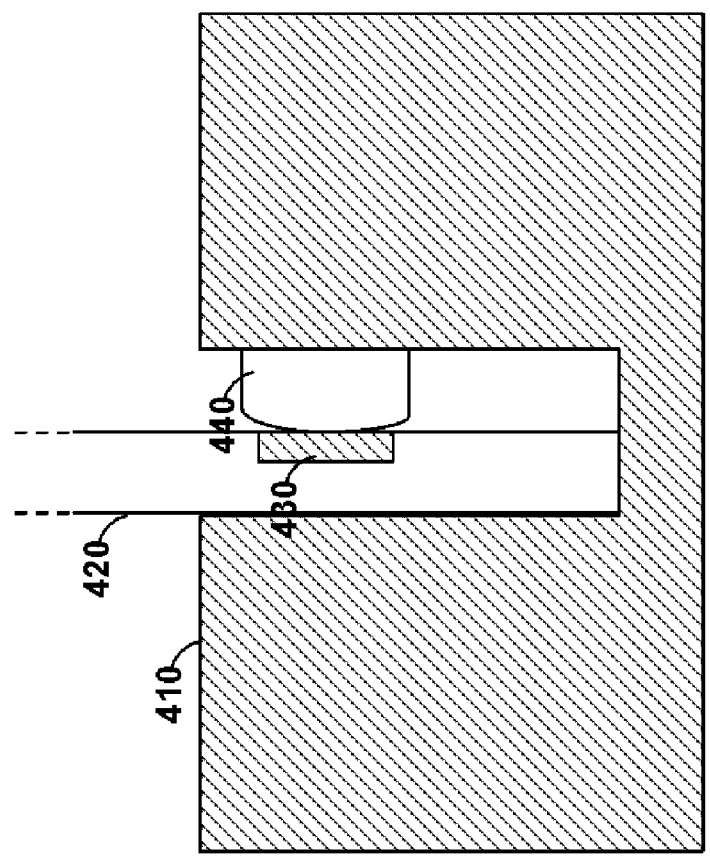
FIG. 4 is an illustration of a card and a reader constructed in accordance with the principles of the present invention.

FIG. 4 shows environment 400 that may include magnetic stripe reader 410, read-head housing 440, card 420, and magnetic emulator 430. Read-head housing 440 may include any number of read-head's such as, for example, one, two, or three read-heads. Each read-head may independently receive magnetic fields from magnetic emulator 430 (or a magnetic stripe, such as a magnetic stripe encoded on-card by card 420). Emulator 430 may be positioned to be adjacent to any one or more read-heads of read-head housing 440 or may be positioned to communicate information to any one or more read-heads of read-head housing 440. Persons skilled in the art will appreciate that emulators with longer lengths may be located within the proximity of one or more read-heads for a longer duration of time when a card is swiped. In doing so, for example, more information may be transmitted from an emulator to a read-head when a card is being swiped.

Figure 5:
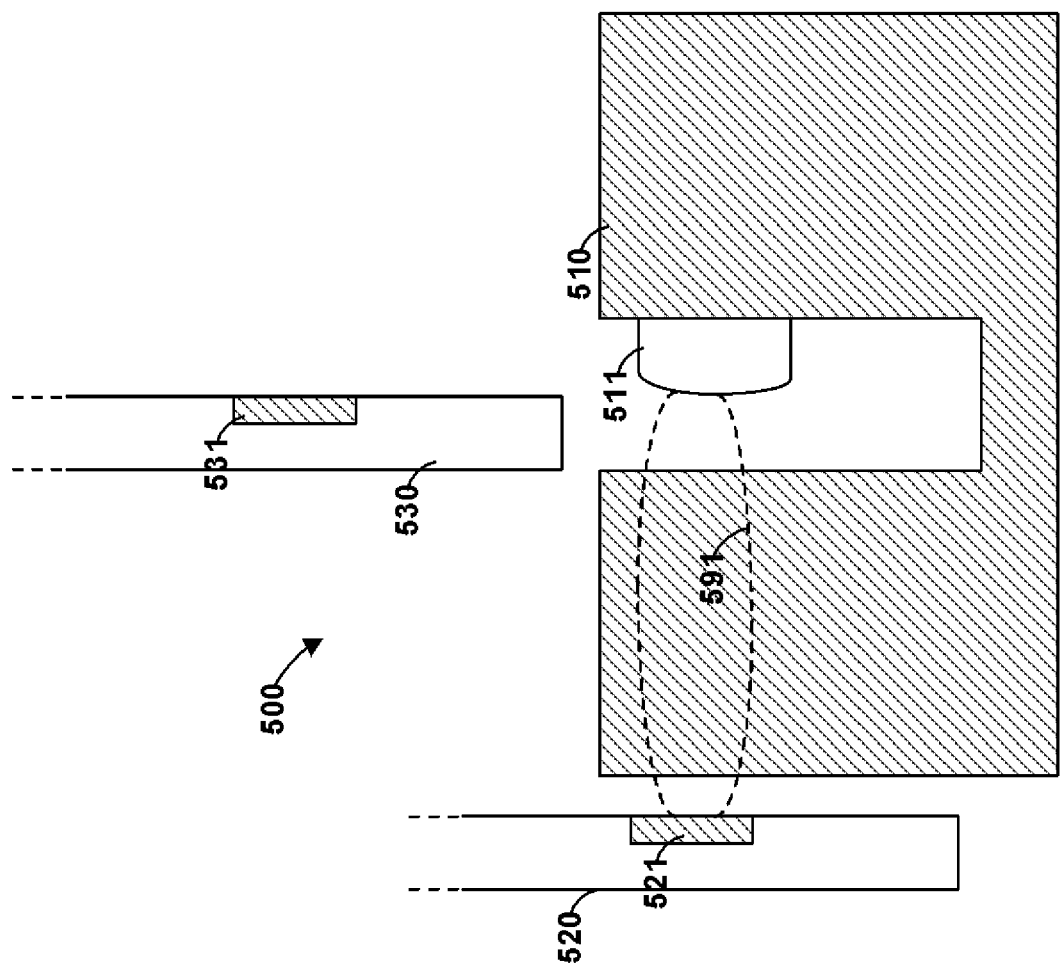
FIG. 5 is an illustration of a card and a reader constructed in accordance with the principles of the present invention.

FIG. 5 includes environment 500 that may include cards 520 and 530 as well as magnetic stripe reader 510. Read-head housing 511 may be included on a wall of a trough of magnetic stripe reader 510. The trough may be sized to accept cards (e.g., credit cards).

Card 520 may include emulator 521. Emulator 521 may provide electromagnetic field 591 that may transmit through a portion of the housing of magnetic stripe reader 510 (e.g., through a wall of a trough to get to read-head housing 511). Accordingly, card 520 may be located outside of a reader—yet still be operable to communicate information to a magnetic stripe reader. A reader may be provided with an outer wall, for example, with a thickness of a quarter of an inch or more. Emulator 521 can provide electromagnetic field 591 over a distance of, for example, a quarter of an inch or more.

Persons skilled in the art will appreciate that card 520 may be coupled to a device via a permanent or removable cable. Such a device may provide power to card 520 as well as control information—such as control information for emulator 530. An external source of power may be utilized, for example, to provide a larger amount of electrical energy to emulator 521 than from a source of power located within card 520. Persons skilled in the art will appreciate that a car having an internal battery may still be able to receive a cable from a device having its own source of electrical energy.

Card 530 may be provided with emulator 531 and may electrically couple with a read-head of magnetic stripe reader 510. Any number of emulators may be provided in card 530 in any number of orientations such that the appropriate electromagnetic field may couple with a read head of read-head housing 511 regardless of the orientation of card 720 with respect to read-head 511. More particularly, for example, additional read-head housings may be provided in magnetic stripe reader 510 at different locations about the reader to electrically couple with a emulators in a number of different configurations. A sticker and/or guide-structures may be provided on a magnetic stripe reader to, for example, direct a user on how to position his/her card (or other device) for contactless transmission of data (e.g., credit card data) to a read-head housing without using the trough that includes that read-head housing.

Persons skilled in the art will appreciate that a magnetic stripe reader may include a trough that includes two (or more) read-head housings 511 located in approximately the same vertical position on a card-swiping trough, but at different horizontal locations on opposite walls of the trough. In doing so, for example, a magnetic stripe may be read regardless of the direction that a card having the magnetic stripe is facing when the card is swiped. Magnetic emulator 521 may, for example, communicate magnetic fields outside both the front and read surfaces of a card. Accordingly, a single emulator 521 may, for example, couple with a single read-head regardless of the direction the card was facing when swiped. In doing so, for example, the costs of readers may be reduced as only a single read-head may be need to receive information regardless of the direction a card is facing when swiped. Accordingly, magnetic readers do not need stickers and/or indicia to show a user the correct orientation to swipe a card through a magnetic stripe reader. An adapter may be provided that coupled directly to a read-head that allows a device not operable to fit in a trough to electrically couple with a read-head.

An emulator may be positioned about a surface of a card (or other device), beneath a surface of a device, or centered within a card. The orientation of a magnetic emulator in a card may provide different magnetic fields (e.g., different strength's of magnetic fields) outside different surfaces of a card. Persons skilled in the art will appreciate that a magnetic emulator may be printed via PCB printing. A card may include multiple flexible PCB layers and may be laminated to form a card using, for example, a hot and/or cold lamination. Portions of an electronic ink display may also be fabricated on a layer during a PCB printing process.

Persons skilled in the art will appreciate that a number does not need to, for example, change with time. Information can change, for example, based on manual input (e.g., a button press or combination of button presses). Additionally, a credit card number may be a static display number and may be wholly or partially displayed by a display. Such a static credit card number may result in the reduction of fraud if, for example, a personal identification code is required to be entered on a manual input entry system to activate the display. Additionally, fraud associated with card cloning may be minimized with the use of a magnetic emulator activated by the correct entry on a manual input entry system.

Person skilled in the art will also appreciate that a card may be cloned by a thief, for example, when the thief puts a illegitimate credit card reader before a legitimate credit card reader and disguising the illegitimate credit card reader. Thus, a read-head detector may detect a read-head housing and then, if a second read-head housing is detected on the same side of the credit card, the reader may transmit information to the second read-head that signifies that two read-head housings were detected. In doing so, for example, a bank, or the police, may be notified of the possibility of the presence of a disguised cloning device. The information representative of multiple read-heads may be included with information that would allow a credit card number to be validated. As such, a server may keep track of the number of read-head housings at each reader and, if more read-head housings are detected than expected, the server may contact an administrator (or the police). The server may also cause the credit card transaction to process or may reject the credit card transaction. If the number of read-head housings (or read-heads) is the number expected by the server, the server can validate the payment transaction.

A payment system using dynamic numbers may, for example, be operable with numbers that are stored outside of the period in which those numbers would otherwise be valid. A server may be included, for example, that accepts a dynamic credit card number, information representative of a past credit card number, and the merchant that is requesting payment. The server may register that merchant for that saved number. The number may be decrypted (or otherwise validated) for that past period of time. Accordingly, the credit card transaction may be validated. Additionally, the merchant identification information may be linked to the stored dynamic credit card number for that past period of time. If the server receives a transaction from a different merchant with that same dynamic credit card number for that same period of time, the server may reject the transaction. In doing so, a merchant may be protected from having credit card numbers stolen from its various storage devices. If a thief steals a number from a merchant's server that is associated with a past period of time, that number cannot be used, for example, anywhere else. Furthermore, such a topology may, for example, allow merchants to provide a one-click shopping, periodic billing, or any other type of feature that may utilize dynamic numbers that are stored and used outside of the period in which the dynamic numbers were generated.

Persons skilled in the art will appreciate that different emulators may be controlled by different switching circuitry (e.g., different transistors).

Persons skilled in the art will appreciate that multiple buttons may be coupled together to form a single-bit bus. If any button is pressed, the bus may change states and signal to the processor to utilize different ports to determine what button was pressed. In this manner, buttons may be coupled to non-triggerable ports of a processor. Each button (or a subset of buttons) may be coupled to one or more triggerable ports of a processor. A port on a microprocessor may be utilized to drive an emulator in addition to, for example, receiving information from a button. For example, once an appropriate personal identification code is received by a processor, the processor may utilize one or more ports that receive information from one or more buttons to drive an emulator (e.g., for a period of time). Alternatively, for example, a magnetic emulator may be coupled to its own triggerable or non-triggerable processor port. A card may also include a voltage regulator to, for example, regulate power received from an internal or external source of power.

Persons skilled in the art will appreciate that any type of device may be utilized to provide dynamic magnetic information on a card to a magnetic stripe reader. As discussed above, a magnetic encoder may be provided that can change information on a magnetic medium where the changed information can be detected by a magnetic stripe reader.

Persons skilled in the art will appreciate that the direction of current through magnetic circuit 650 may be changed and controlled in a pattern that is representative of magnetic stripe data. Particularly, a processor may, for example, transmit information through a coil by changing the direction of the electromagnetic field generated from emulator circuit at particular times. A change in the frequency of field reversals may be representative of, for example, a particular bit of information (e.g., "1" or "0").

Figure 6:
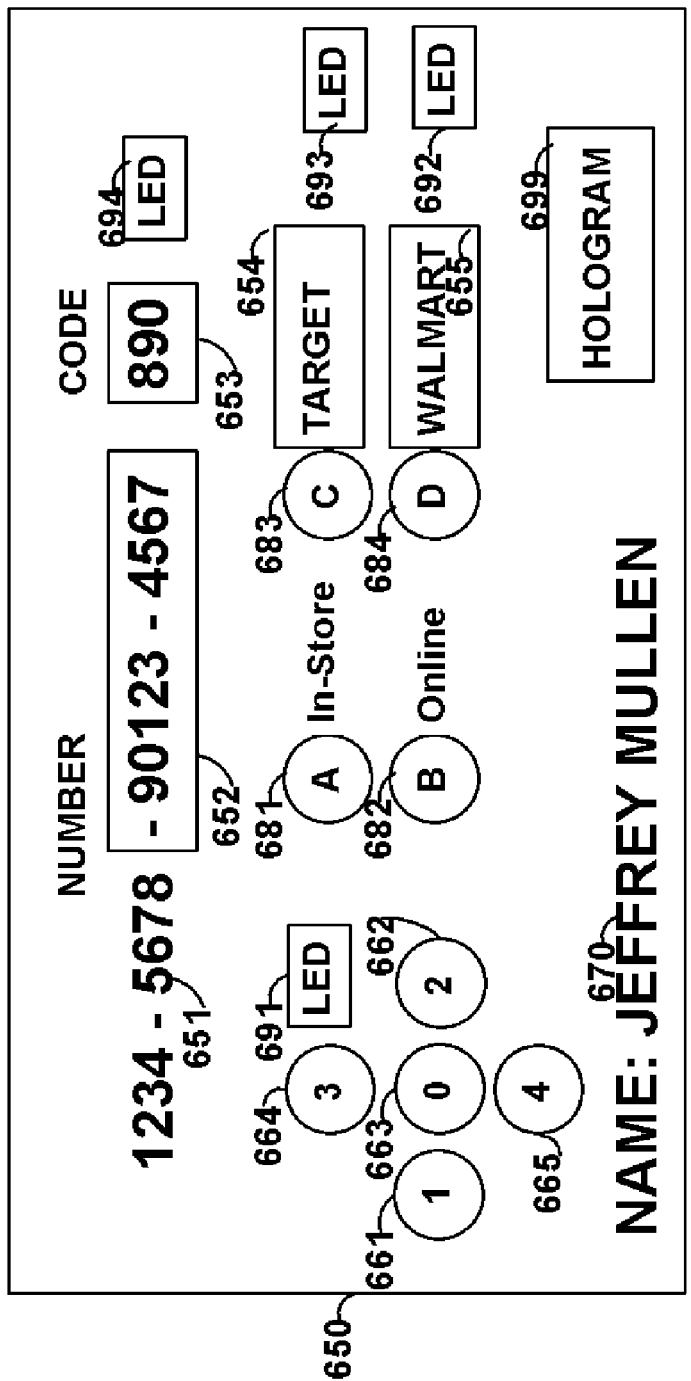
FIG. 6 is an illustration of a card and a payment process constructed in accordance with the principles of the present invention.

FIG. 6 shows card 650 that includes buttons 651-664, light sources 691-694, displays 852-853, permanent information 651 and 670, buttons 681-684, and hologram 699. A user may be provided with a payment number. Such a payment number may be comprised of permanent data, dynamic data, or a combination of permanent and dynamic data. Dynamic data may be provided, for example, on display 652. Display 653 may be utilized to provide a code, which may be dynamic. Such a code may be utilized in authorize a transaction. Persons skilled in the art will appreciate that displays may display a code, payment number, or any type of data that changes based on time or based on use (e.g., utilizes one-time use data). Similarly, data may be static and may not change. Accordingly, for example, a display may be utilized to display the same data when desired such that the data may be hidden when the data is not desired to be displayed. Buttons 651-664, 681-682, and/or 683-684 may be utilized to signal a processor to display information on display 652, display 643, or display 652 and display 653.

A Personal Identification Code (PIC) may be entered to utilize to display data, as well as instruct a processor to provide particular data. For example, a particular PIC may provide one payment number (e.g., a credit card number) while a different PIC may provide a different payment number (e.g., a debit card number). A Personal Identification Code (PIC) may include a sequence of button presses (e.g., 5 particular button presses). Furthermore, a PIC may be utilized to unlock a card so that the card may be utilized. For example, buttons 681, 682, 683, and 684 may not be utilized by a user until an appropriate PIC has been entered via buttons 651-665. A number may be changed based on time (e.g., via display 652, display 653, or display 652 and display 653). Accordingly, a PIC may be entered such that the particular number associated with a particular button (e.g., a number associated with button 651) for a particular time period (e.g., a particular day) may be displayed. One PIC may activate display 652 while another PIC may activate display 653.

Light source 691 may be an LED or other source of light. Light source 691 may display light each time a button associated to light source 691 is pressed (e.g., buttons 661-662). Similarly, light source 692 may display light each time a button associated with light source 692 is pressed (e.g., button 681 or 682). Light source 693 may display light each time a button associated with light source 693 is pressed (e.g., light source 693 or 694). Light source 694 may be associated to a component and may display light each time that component is activated (e.g., display 653 or 652 is activated). Light sources may emit light having different colors. For example, a processor may determine that a PIC provided to the processor via buttons 661-665 matches a valid PIC for performing an operation. Each button press may cause light source 691 to emit light of a first color (e.g., YELLOW). The last button press to complete the PAC, however, may cause light source 691 to emit a different color if the PIC is VALID (e.g., emit GREEN) yet emit another color if the PIC is INVALID (e.g., emit RED). Particular areas of a laminated card may be transparent such that light from a light-source illuminates the transparent area.

Button 681 may be associated with a card of a particular country. Persons skilled in the art will appreciate that a card may be provided with a default number. Such a default number may include, for example, permanent data 651 and data displayed on display 652. Accordingly, a particular PIC may display the default data on display 652.

Persons skilled in the art will appreciate that other default data may be provided to other components of a card upon entry of a PIC. For example, particular default data (e.g., payment card number and discretionary data) may be communicated to a magnetic emulator (or magnetic encoder) such that the information may be communicated to a magnetic stripe read-head. Similarly, default data (e.g., payment card number and discretionary data) may be communicated to an RFID antenna, an IC chip, or an RFID antenna and an IC chip. Such default data may be different for each component (e.g., magnetic encoder/emulator, RFID antenna, IC Chip) and may be in different formats (e.g., one track of payment data for one magnetic emulator and another track of payment data for another magnetic emulator).

Button 681 may cause, for example, display 652, display 653, or display 652 and 653 to display data associated to button 681. Similarly, data associated to button 681 for other components of card 650 (e.g., a magnetic emulator, magnetic encoder, RFID antenna, and IC chip) may be communicated through those components. Button 681 may be associated with, for example a particular territory (e.g., America). Accordingly, for example, information communicated via card 650 may be associated with a default country upon entry of a particular PIC until, for example, a button is pressed associated with a different country. At this time, for example, the information communicated by card 650 may change to the information associated with the particular button pressed. Button 692 may be provided for a country different than, for example, a default country and a country associated with another button (e.g., button 681). A card may not be associated with a default country such that, for example, a button is pressed to determine the type of information communicated by a card.

Button 683 may be utilized to provide instructions to a processor that a gift card is desired to be utilized via card 650. A gift code may be entered (e.g., via buttons 661-665) after button 683 is pressed such that a user may, for example, associate a gift card to card 650. Accordingly, card 650 may be utilized to make a gift purchase such that the original gift card may be thrown out (or left at home). The code entered into card 350 may be utilized, for example, to provide a processor with a number to transmit via the card (e.g., next time button 683 is utilized). Such a number (as well as associated data such as associated discretionary data) may be communicated by card 650 via one or more displays, magnetic emulators, magnetic encoders, RFID antennas, and IC chips. A code may alternatively, for example, transmit a flag (e.g., discretionary data) that a gift card is being utilized (e.g., upon another use of button 683) such that a server may look at a seller ID number and check if there are any gift cards associated to a particular payment card number for that seller ID number. Accordingly, for example, a user may obtain a gift card (e.g., Target gift card) and may link that gift card to his/her payment card account (e.g., credit card account) and may utilize a button (e.g., 683) to send a flag that a gift card is desired to be utilized. A code may be entered to provide a particular flag (e.g., a flag associated with a particular seller). Alternatively, no code may be entered and button 683 may just be utilized to generate a generic flag (e.g., causing a server to check if there are any linked gift cards for the account associated with the seller associated with the utilized point-of-sale reader). A user may be provided with a particular code to be entered when utilize the gift card at an online store (e.g., Target's online store). The online store may, for example, allow a user to enter his/her payment information (e.g., credit card number, expiration date, name on card, zip code associated with card) and allow the user to select whether a gift card should be utilized associated with that card (e.g., via a radio button or other webpage input structure).

Button 684 may be provided. Button 684 may be utilized, for example, to make an in-store purchase. Button 684 may activate, for example, display 652 but not display 653. Code 653 may be utilized, for example, to at least complete a particular online transaction. In not activating display 653, for example, a user that is provided with a card during an in-store purchase may not gain access to information displayed on display 653. Persons skilled in the art will appreciate, for example, that the information on display 653 may be transmitted via a component (e.g., emulator) even though the information is not displayed. Moreover, for example, display 652 and 653 may be the same display but that a particular interface (e.g., button) may display information on different portions of the display.

Display 654 may be provided to display information to instruct a user that interaction with button 683 may result in a processor performing a particular action. For example, display 654 may display the name of a gift card such that if a user utilizes button 683, payment information associated with the gift card may be communicated from a magnetic emulator or encoder. Similarly, display 655 may display information associated with a particular action that would occur if, for example, a user utilizes button 684.

Figure 7:
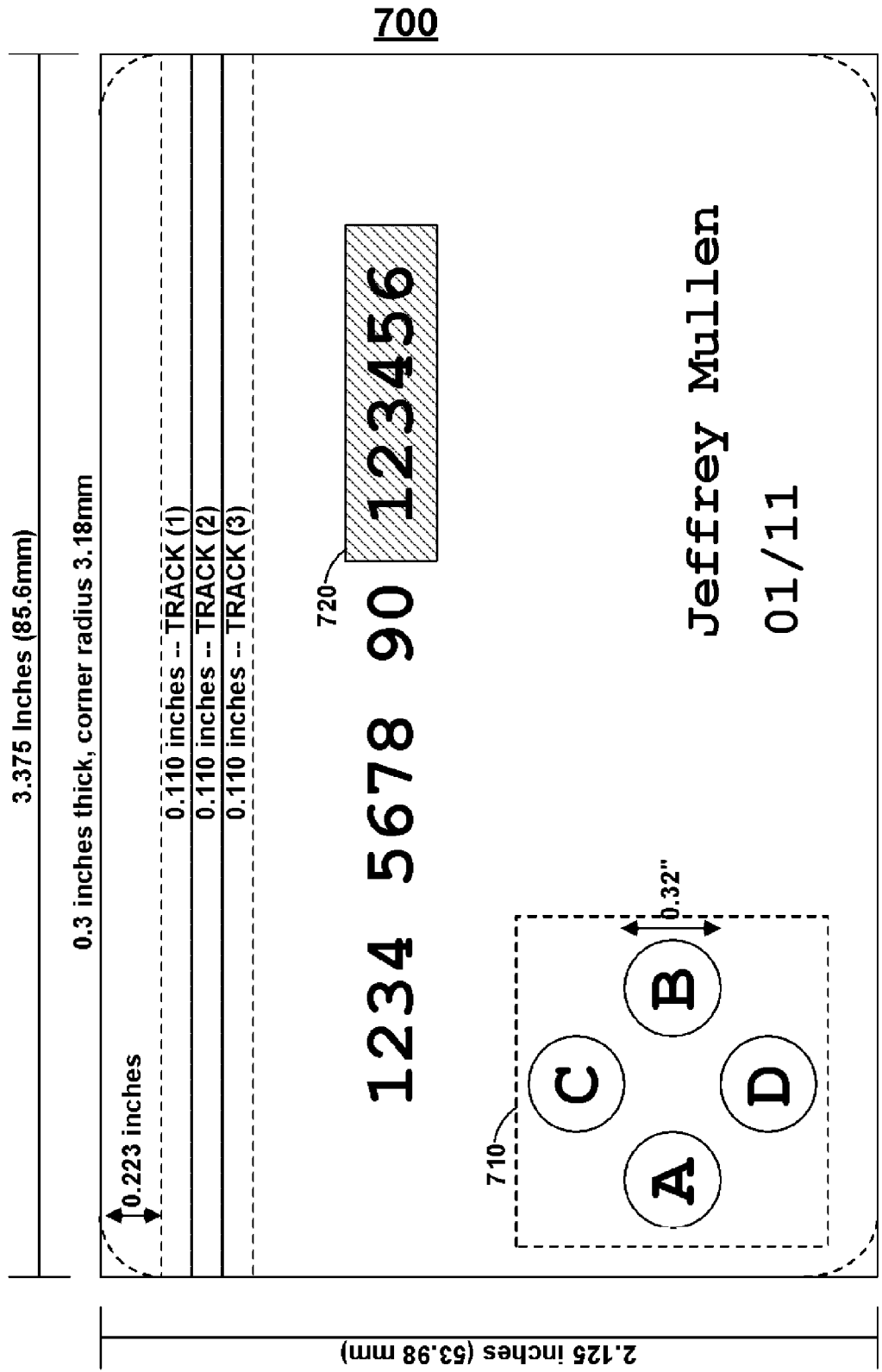
FIGS. 7-49 are illustrations of cards constructed in accordance with the principles of the present invention.

FIG. 7 shows card 700. Card 700 may include display 720 and button array 710. Button array 710 may be located anywhere on a card. For example, one or more buttons of button array 710 may be located over a magnetic emulator without interfering with data communicated from the magnetic emulator to a read-head of a magnetic stripe reader.

A button array may more generally be provided as a user interface array. A user interface may, for example, be able to receive manual input from a user. Any number of buttons (or other user interfaces) may be provided in an array. For example, four buttons may be provided. Alternatively, for example, five or six buttons may be provided. The buttons may be provided in one or more rows or columns. Alternatively, for example, the buttons may be included in another formation to decrease the distance between the most remote buttons. For example, five buttons may be provided in the shape of a directional pad. In reducing the distance between the most remote buttons in an array configuration, a user may be provided with a configuration that allows for very fast, and possibly one-handed, user interaction.

Persons skilled in the art will appreciate that any card face may be located on the obverse or reverse of a card. Accordingly, for example, a magnetic emulator/encoder may be provided on any card face. Similarly, any permanent information (e.g., embossed card number) may be provided on any card face. Additionally, for example, persons skilled in the art will appreciate that a magnetic emulator may be provided inside of a card.

Figure 8:
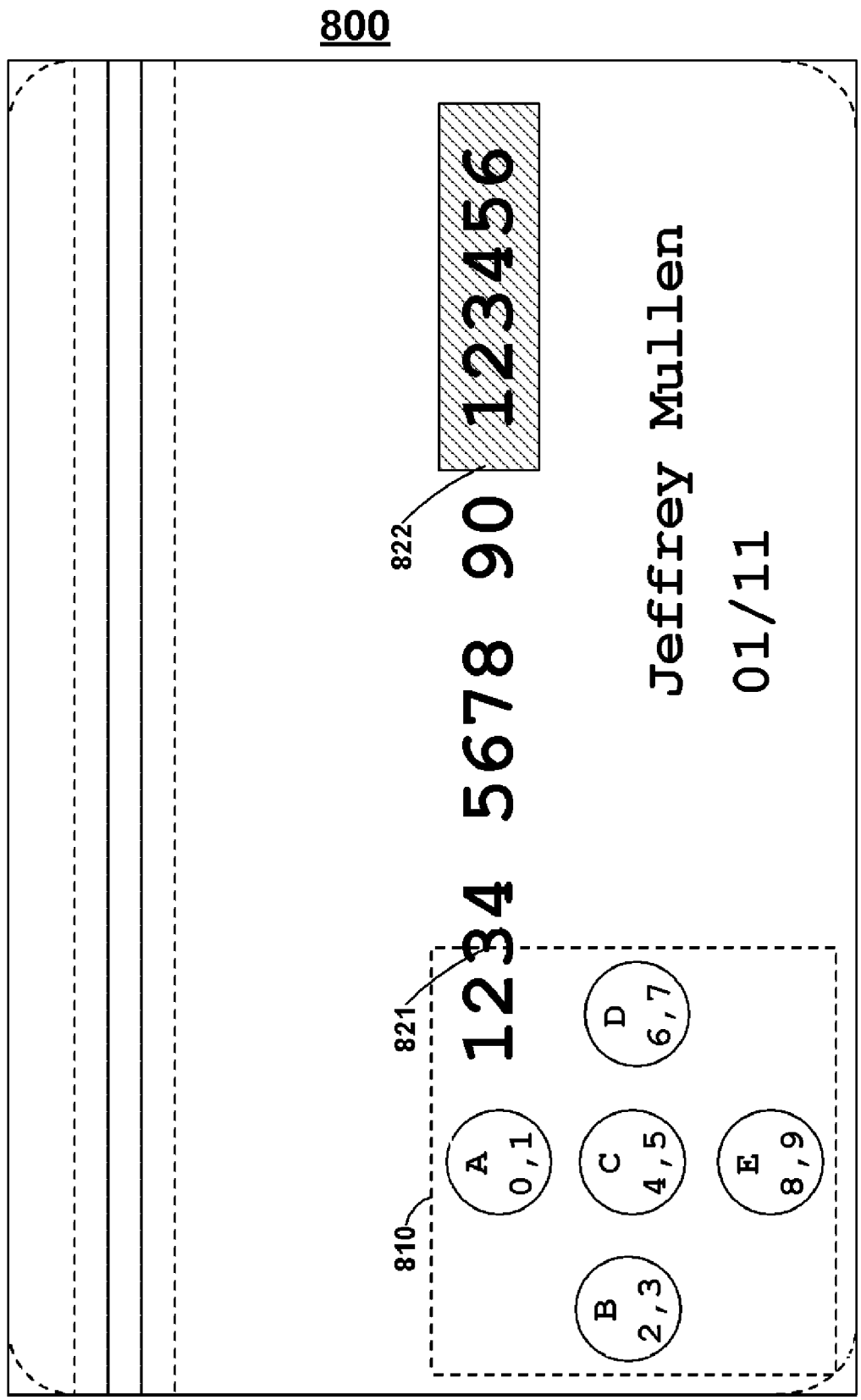

FIG. 8 shows card 800 that may include button array 810. Button array 810 may include any number of buttons, or other user interfaces, such as five buttons. Indicia may be provided on the buttons in order to enhance the functionality of the buttons. For example, a button may include both a character and multiple digits. In doing so, for example, a user may be able to enter in both numerical and character based codes. Button array 810 may be provided in a directional pad configuration. Accordingly, for example, a card may display on a display information that can be scrolled up and down as well as left and right. Accordingly, a directional pad configuration may facilitate a user when the user interfaces with such a display functionality. A directional pad configuration may also, for example, allow for spaces at the corners of the directional pad configuration. Permanent information may be provided in such spaces. For example, one or more digits of number 821 may be provided in such spaces. Display 822 may also be provided to display information such as, for example, payment card number information. Button array 810 may be located in any area on the obverse or reverse side of a card. For example, button array 810 may be located about the lower right, upper right, lower left, or upper left corner of a card.

Figure 9:
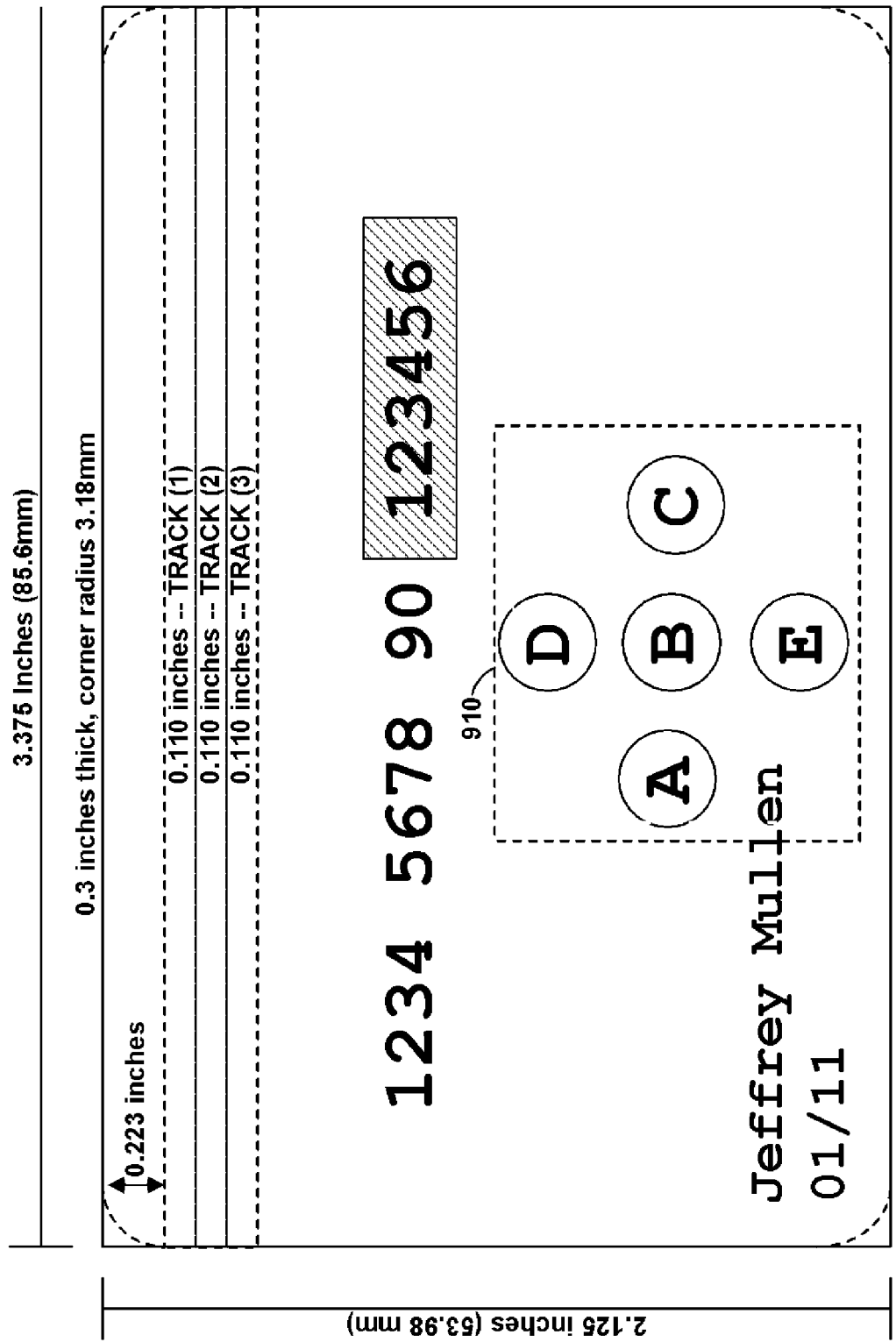

FIG. 9 shows card 900 that may include button array 910. Persons skilled in the art will appreciate that each button of a button array may be coupled to different ports of a microprocessor. Such ports may be, for example, triggerable ports. Additionally, for example, each button of button array 910 may be coupled to intermediary circuitry such as a multiplexer. Button array 910 may be located, for example, in the proximity of the middle of card 900. For example, button array 910 may be located in the middle, near the bottom of card 900 or in the middle, near the top of card 900. Alternatively, for example, button array 910 may be located in the center of card 900.

Figure 10:
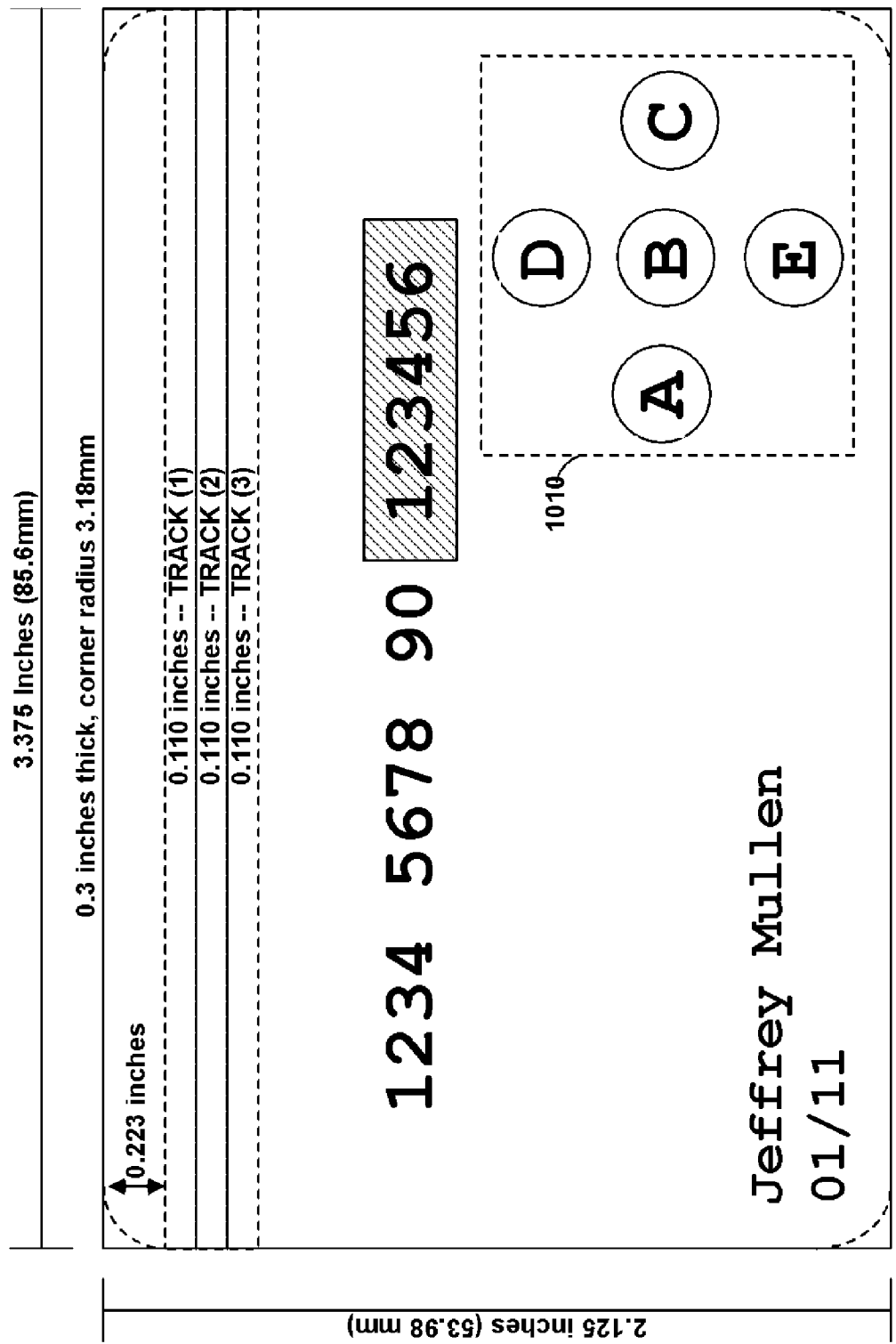

FIG. 10 shows card 1000 that may include button array 1010 located on the lower right corner of a surface of card 1000.

Figure 11:
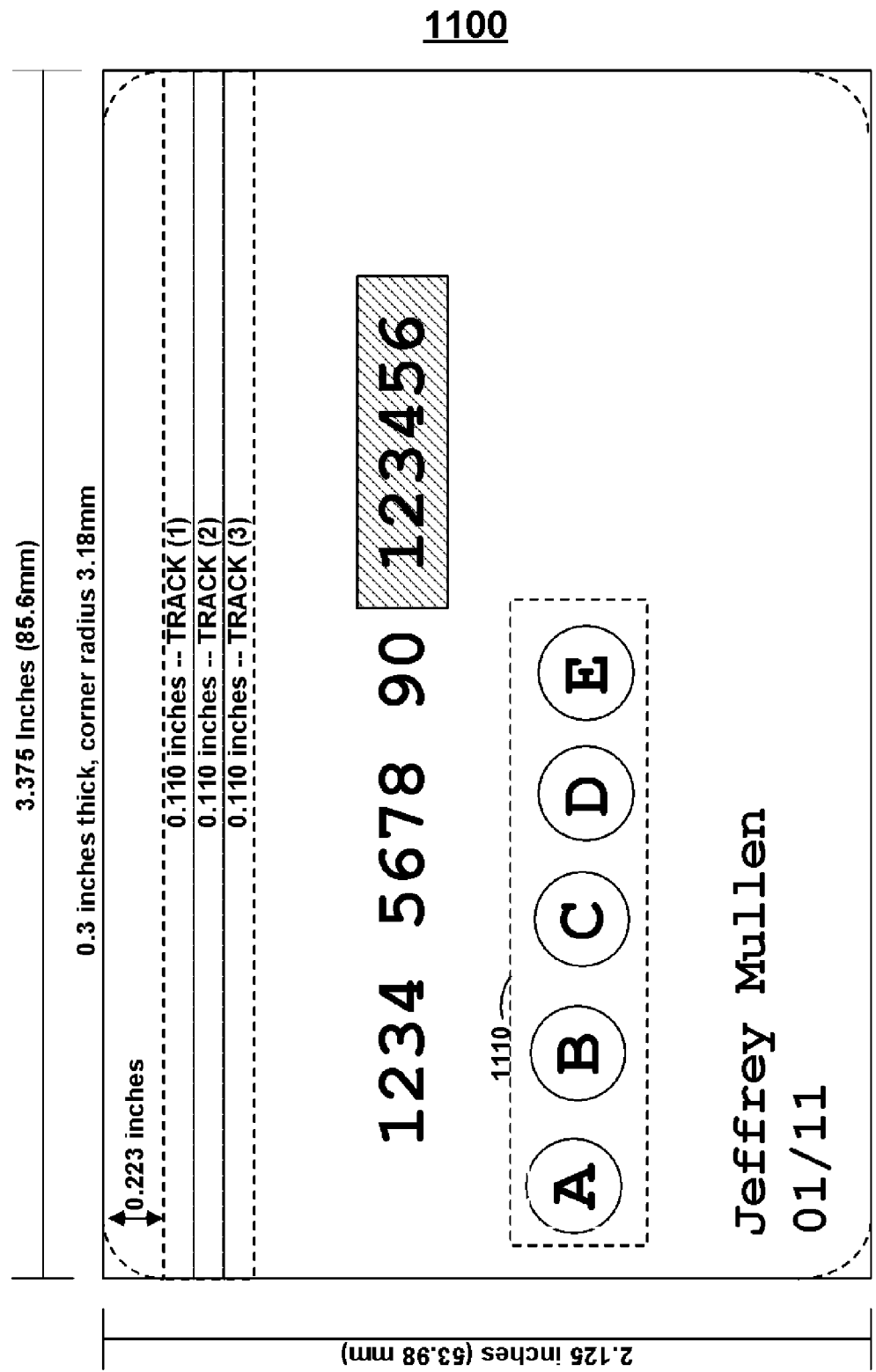

FIG. 11 shows card 1100 that may include button array 1100. Button array 1100 may include, for example, multiple buttons located in a horizontal configuration. By providing buttons in a horizontal configuration, for example, a user may easily understand any numbering scheme of the buttons in the array. For example, buttons may be numbered, or characters ordered, in ascending order from left to right (for users that read left to right) or right to left (for users that read right to left). Array 1110 may be located anywhere on the front or back of a card. For example, array 1110 may be located on the left-side or right-side of card 1100.

Figure 12:
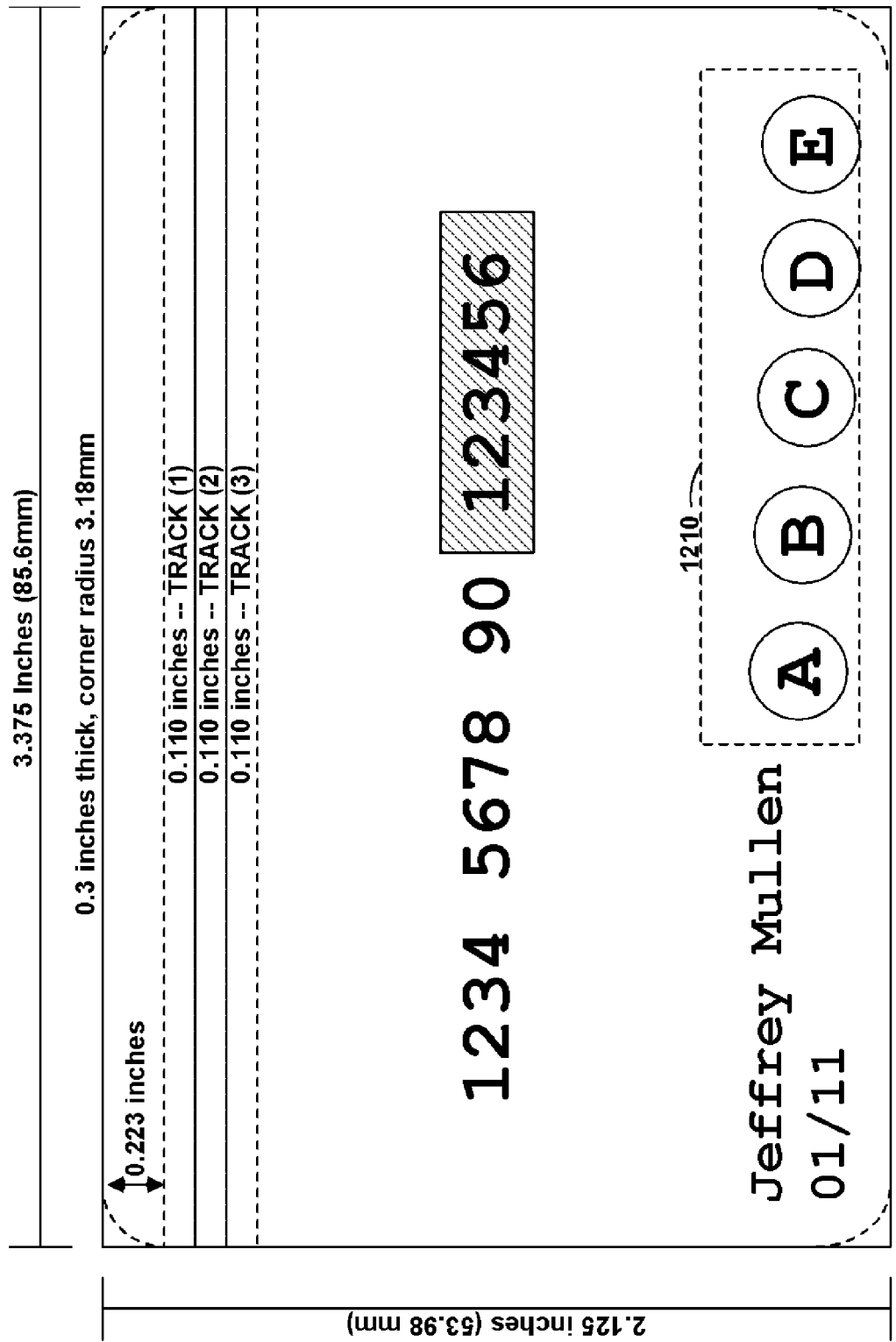

FIG. 12 shows card 1200 that may include button array 1210.

Figure 13:
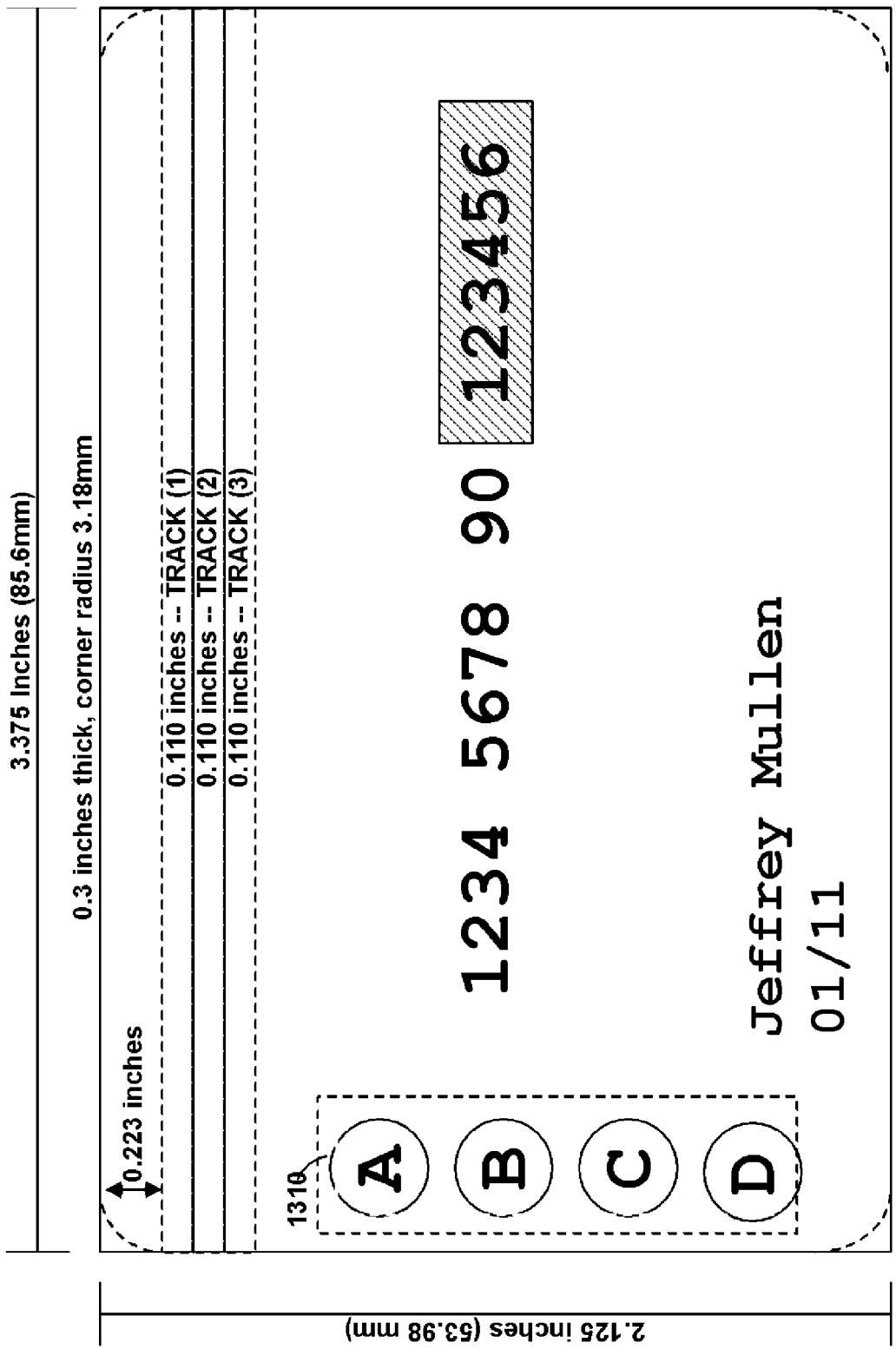

FIG. 13 shows card 1300 that may include button array 1310. Button array 1310 may include, for example, any number of buttons in a vertical configuration. Indica located on the buttons may be oriented such that the indicia is properly read when the buttons are oriented vertically with respect to the user. Alternatively, for example, indicia located on the buttons may be oriented horizontally such that a user may rotate a card so that the vertical configuration is perceived as a horizontal configuration and the indicia is read horizontally.

Figure 14:
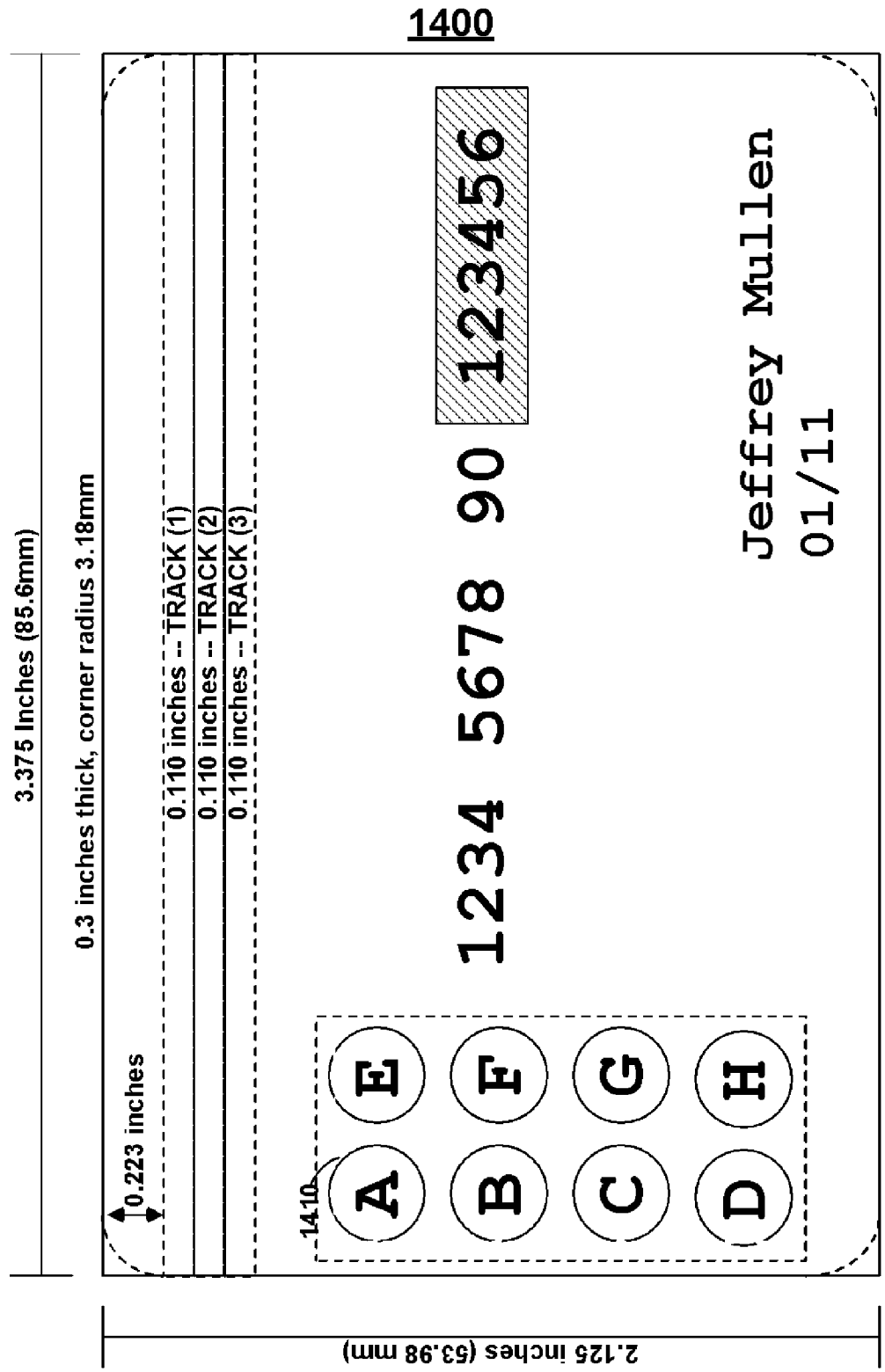

FIG. 14 shows card 1400 that may include, for example, button array 1410. Button array 1410 may include, for example, two columns of buttons. The buttons, liked any of the control interfaces provided, may include indicia such as, for example, numbers, characters, and symbols. Button array 1410 may include an even number of buttons such as, for example, eight buttons.

Figure 15:
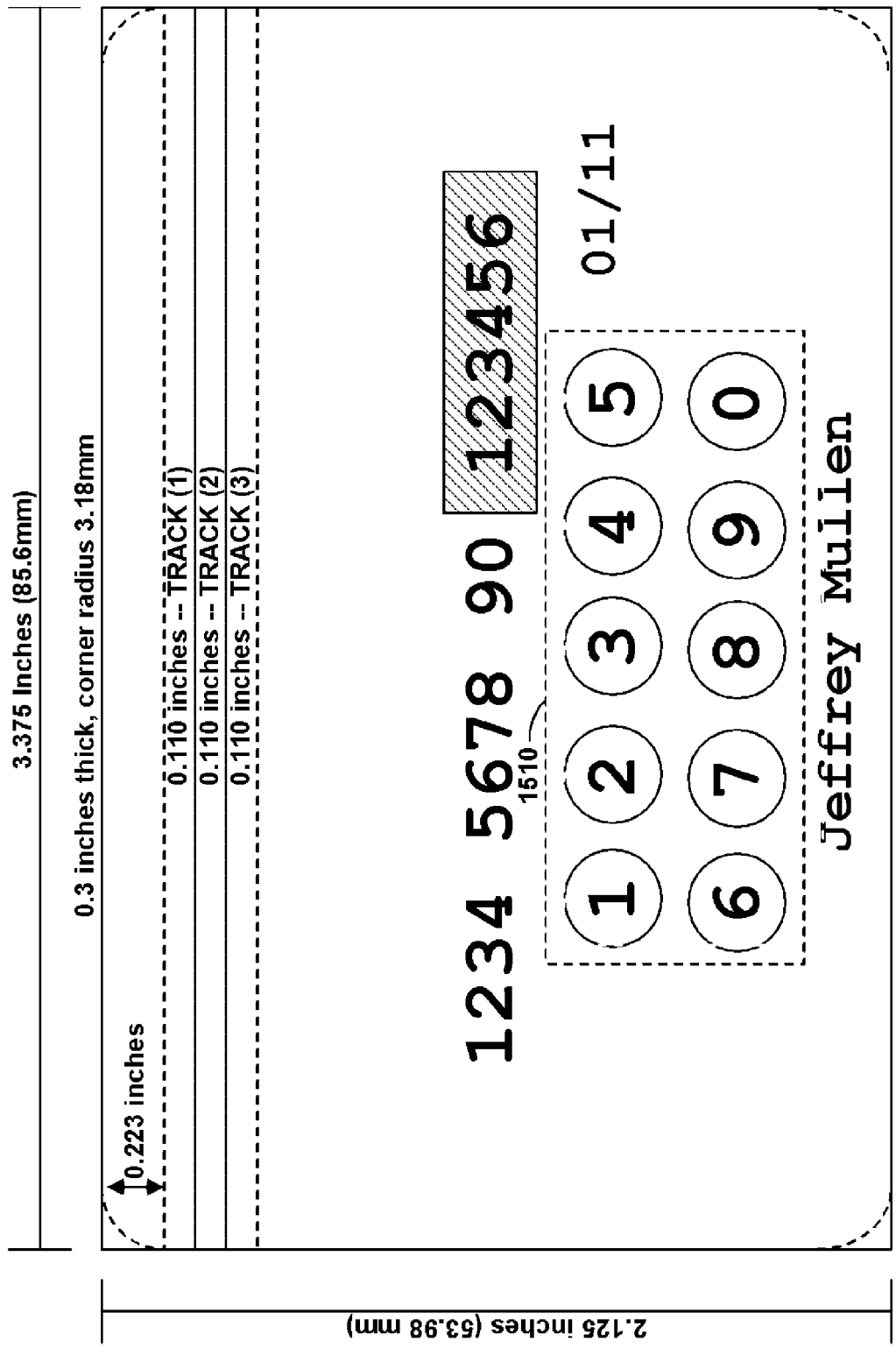

FIG. 15 shows card 1500 that may include, for example, button array 1510. Button array 1510 may include, for example, two rows of buttons. Button array 1510 may include, for example, an even number of buttons. Button array 1510 may include, for example, ten buttons. Persons skilled in the art will appreciate that additional buttons may be provided on a card outside of a button array. Buttons in a button array may, for example, be associated with a particular functionality or set of functionalities (e.g., PIC/PIN entry).

Figure 16:
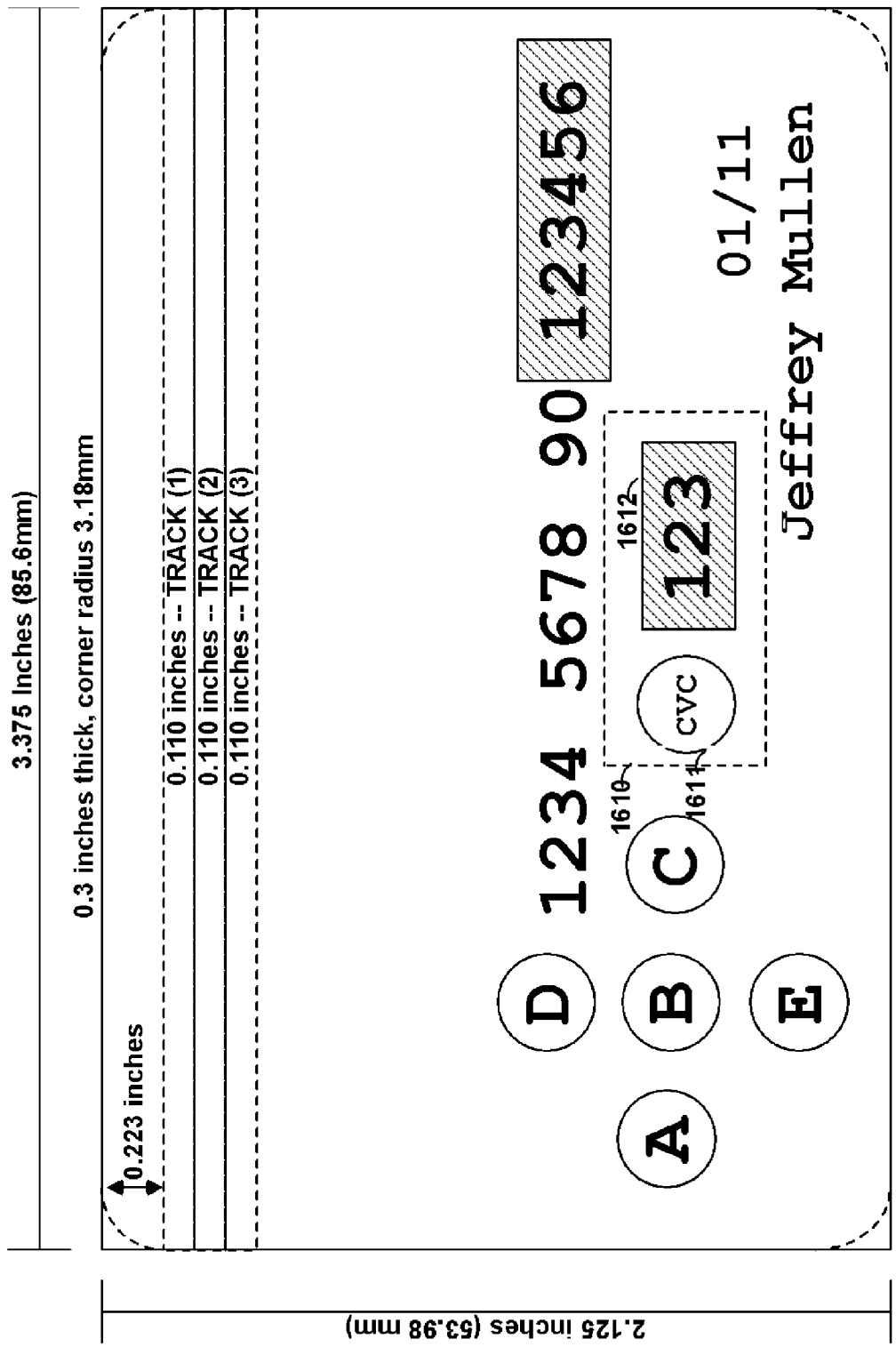

FIG. 16 shows card 1600 that may include button and display portion 1610. Portion 1610 may be located on any surface of any card. Button and display portion 1610 may include, for example, display 1612 and button 1611. Display 1612 may display particular information every time button 1611 is pressed. For example, display 1612 may display a code (e.g., CVC) every time button 1611 is pressed. Any display, such as display 1612 may be, for example, a bi-stable display such that power is utilized to change the state of the display—but is not utilized to maintain the state of the display. Accordingly, for example, a dynamic security code may be provided such that each time button 1611 is pressed, another security code may be displayed on display 1612. Such a security code may be, for example, a one-time security code or, alternatively, a code that is generated based on time. A bi-stable display may utilize power to change the number that is displayed but may not, for example, utilize power to maintain the display of any particular number. Alternatively, for example, a non bi-stable display may be utilized. A non bi-stable display may be utilized that utilizes power to maintain the display of indicia.

A card may include, for example, more than one display. A card may include, for example, both bi-stable and non bi-stable displays. In doing so, for example, a card may properly conserve energy from one or more on-board batteries. Particularly, a bi-stable display may be provided on a card that absorbs a large amount of power in order to change displayed indicia. Accordingly, a non bi-stable display may be provided on a card that absorbs a small amount of power in order to change displayed indicia and a small amount of power to maintain the displayed indicia. Accordingly, for example, a bi-stable display may be utilized to display information that is desired to be viewed for a relatively long period of time while a non bi-stable display may be utilized to display information that is desired to be viewed for a relatively short period of time. In providing both a bi-stable and a non bi-stable display, for example, electrical energy absorbed by a card may be minimized. A security code, for example, may be provided on a non bi-stable display. A portion of a card number may be provided, for example, on a bi-stable display. Alternatively, for example, a security code may be provided on a bi-stable display and a card number may be provided on a non bi-stable display. A non bi-stable display may also be advantageous, for example, when indicia is desired to be frequently changed on a display (e.g., once every few seconds).

Display 1612 may, for example, be provided as a non bi-stable display and may display a code that changes with time. Accordingly, for example, the activation of button 1611 by a user may cause a code to be displayed on display 1612 for a pre-determined period of time (e.g., approximately 10 seconds). Accordingly, for example, the number may change according to a longer period (e.g., an hour or a day). Accordingly, a user may press button 1611 multiple times during that period and the same number may be displayed on display 1612. A code may comprise, for example, three or four digits. Such a code may be provided magnetically through a magnetic emulator or encoder. Alternatively, a different three or four digit code may be provided through a magnetic emulator or encoder. A display may display indicia with two color tones (e.g., black and white) or may display indicia with several color tones.

Figure 17:
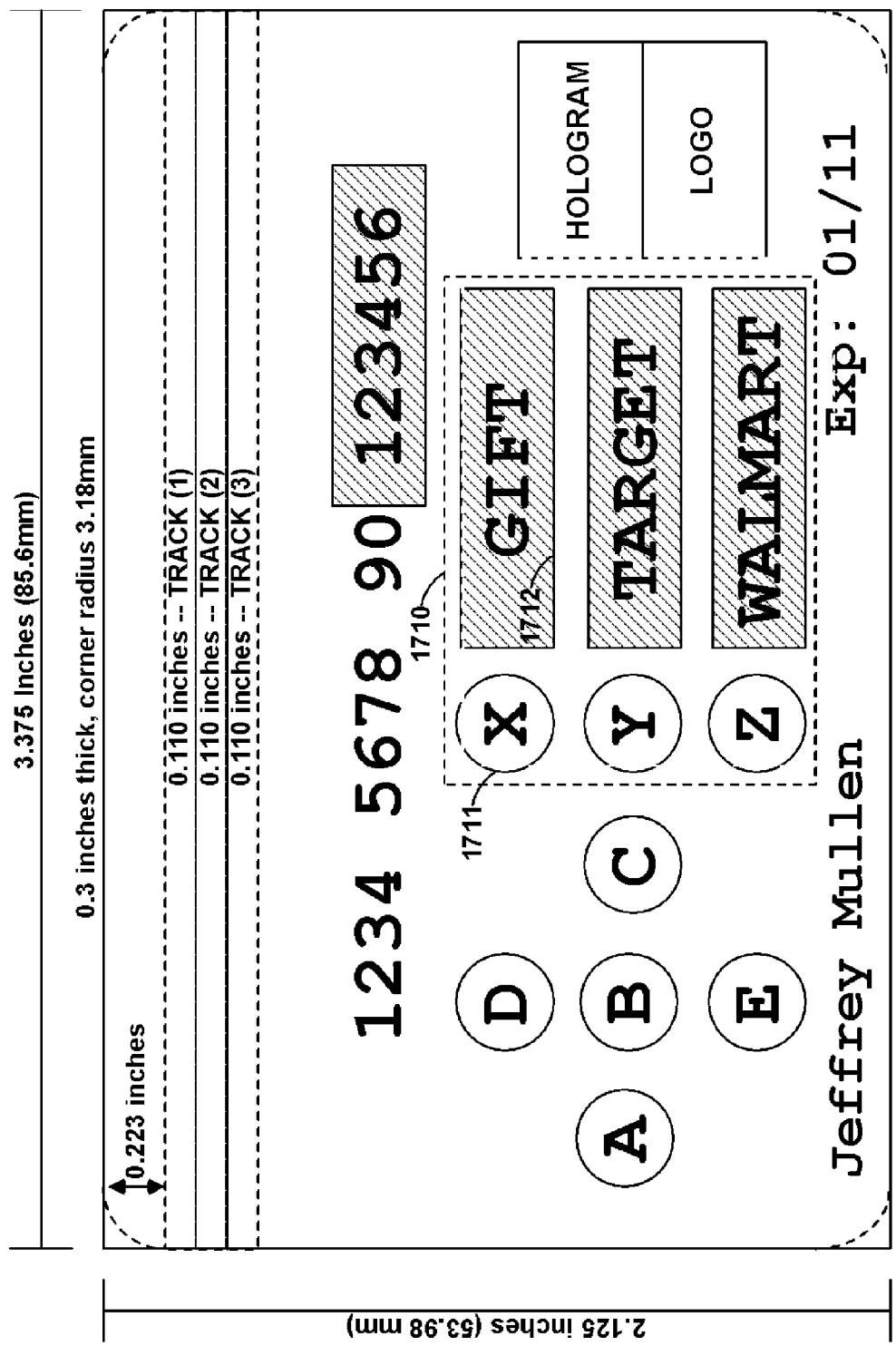

FIG. 17 shows card 1700 that may include portion 1710. Portion 1710 may include multiple buttons, each associated with a different display. Multiple buttons may be associated with a single display. An association may be functional in that interaction with a particular button causes an associated display to perform a particular function. Code executed by a microprocessor may, for example, define the association of a button and a display.

Card 1700 may be utilized as, for example, a programmable gift card. For example, a store may sell card 1700. A purchaser of the gift card may, for example, give the gift card to a friend or relative. The gift card may be associated with, for example, a pre-determined amount of money (e.g., $20, $50, $100, $200, $250, or $500). Alternatively, for example, the amount of the gift card may be determined at purchase by the purchaser. The recipient of the gift card may, for example, visit a webpage associated with the issuer of the gift card. The recipient may, for example, enter in an identification code that identifies the particular gift card. The user may then be provided with a number of stores (e.g., Target, Best Buy, and Walmart). The user may select any number of stores and may allocated the total amount of the gift card amongst the selected stores. The user may then be provided with a code (or several codes). The user may utilize controls (e.g., buttons) located on gift card 1700 to enter this code. The code may, for example, be received by a microprocessor located on card 1700. The microprocessor may utilize the code to identify the stores selected by the user and the associated gift amount allocations. Accordingly, for example, the gift card may associate the selected stores with a particular display and button. The gift card may automatically display the name of the store and the amount of each gift allocation on the display once the microprocessor processes the received code. Accordingly, a user may walk into a store and select an appropriate button to communicate information about the gift card to a card reader (e.g., via an IC chip, RFID antenna, or magnetic encoder/emulator). Persons skilled in the art will appreciate that a programmable gift card may be provided with a static magnetic stripe without a magnetic emulator or encoder. Instead, for example, the programmable gift card's identification may be sent through a reader and a remote server may determine whether the store associated with the reader was selected by the user and allocated a particular gift amount. Alternatively, for example, the card may display and electrically communicate different information depending on, for example, the particular gift a user selected on a programmable gift card.

Figure 18:
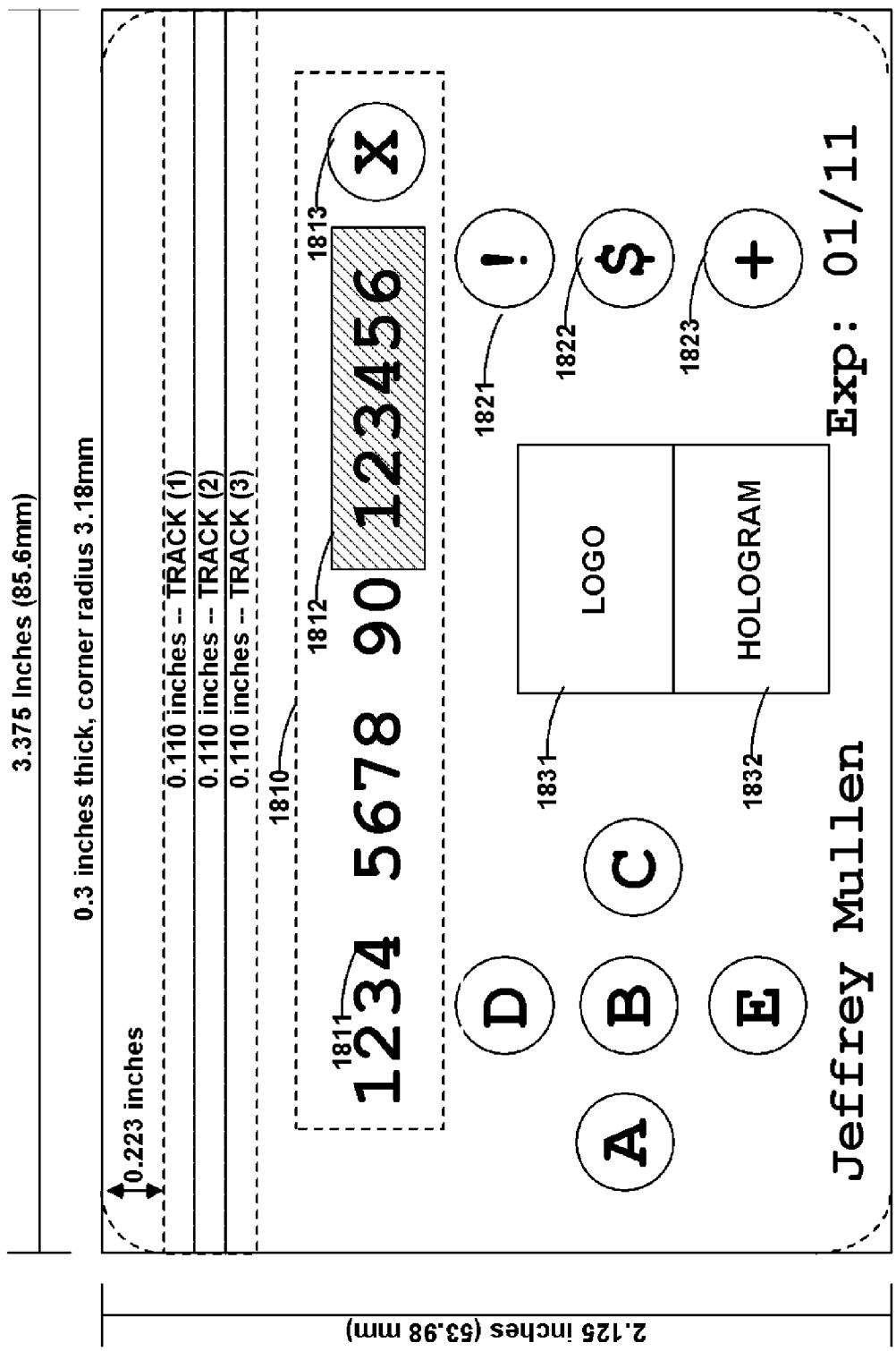
Figure 19:
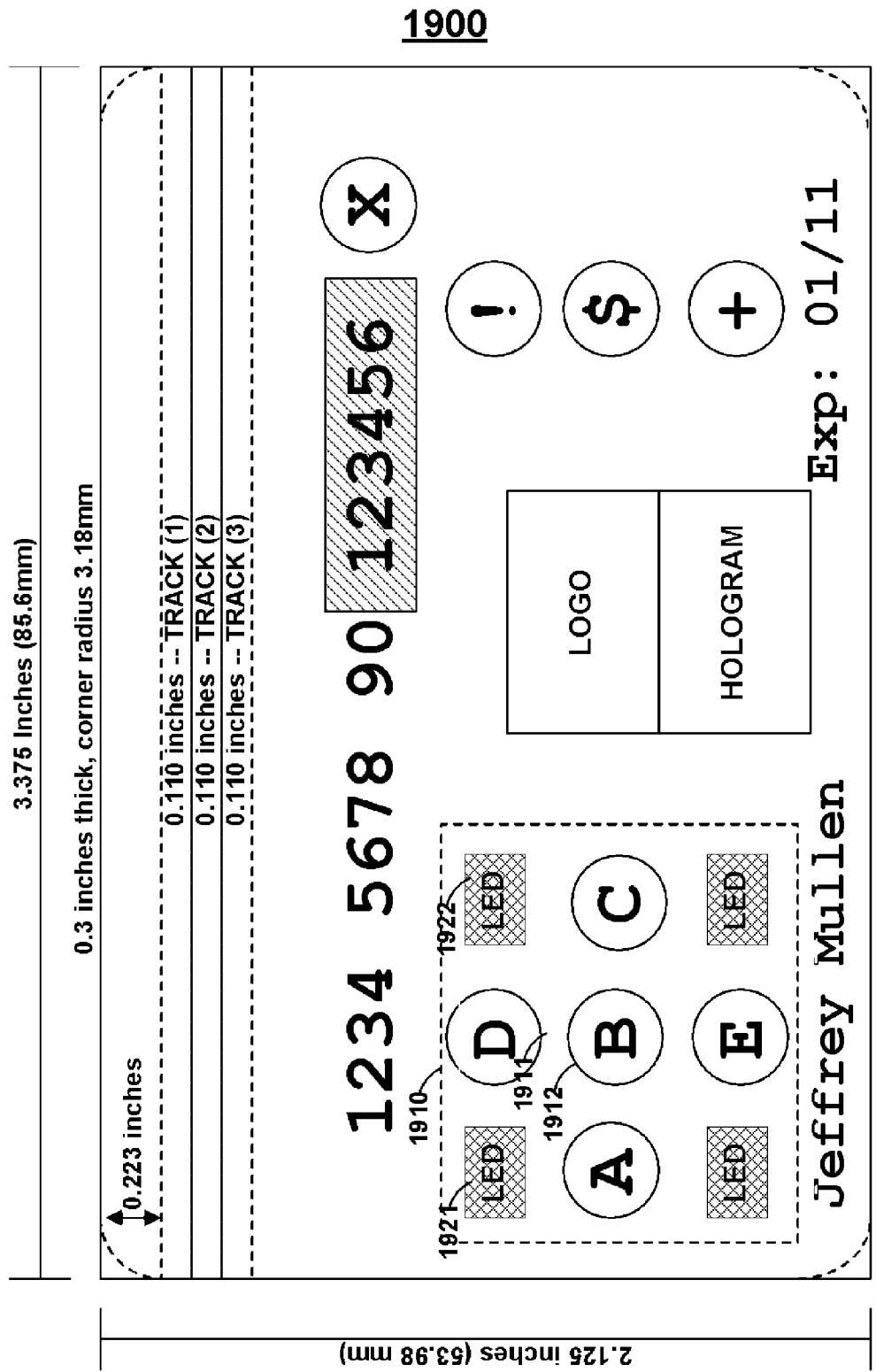

FIG. 18 shows card 1800. Card 1800 may include portion 1810 that may include permanent information 1811, display 1820, and button 1813. Buttons 1821, 1822, and 1823 may also be included. The activation of button 1813, 1821, 1822, and 1823 may cause different information to be displayed on display 1812. Hologram 1832 and logo 1831 may be provided on card 1800. Hologram 1832 and 1831 may be located about the middle of one of the surfaces of card 1800.

Card 1900 may include, for example, portion 1910. Portion 1910 may include, for example, multiple buttons and light sources. For example, portion 1900 may include a light source (e.g., LED) for every button (e.g., four light sources and four buttons). Alternatively, portion 1900 may include a different number of buttons and light sources. For example, portion 1900 may include five buttons and four light sources. The light sources may emit light in order to provide the user of card 1900 with valuable information. For example, the light sources may indicate to a user which button or buttons were pressed by a user. For example, a user pressing button 1910 may cause both light sources 1921 and 1922 to emit light. A user pressing button 1912 may cause all the light sources within portion 1910 to emit light. Sources of light may be provided that emit a single color or more than one color.

Figure 20:
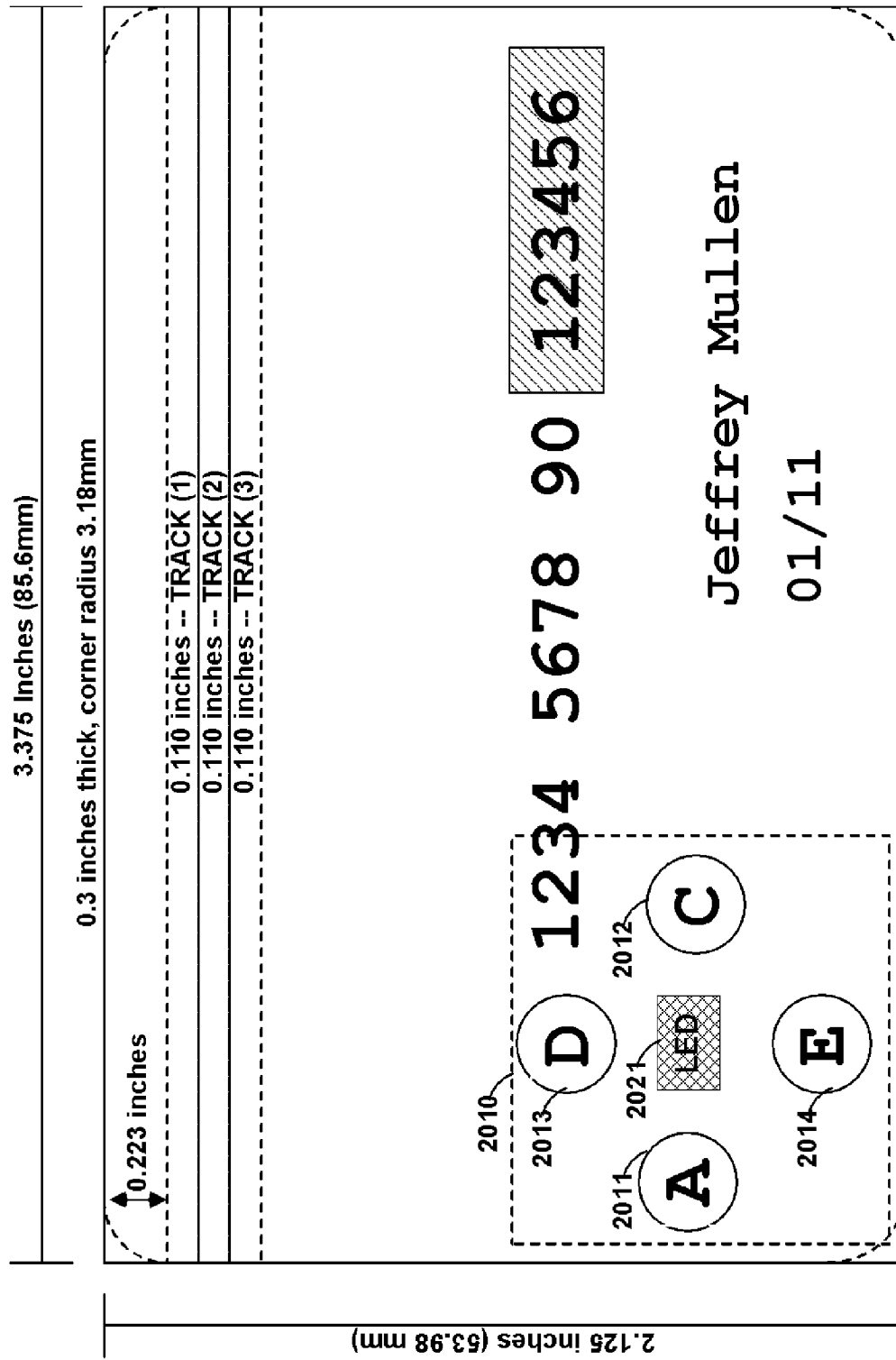

FIG. 20 shows card 2000 that may include portion 2010. Portion 2010 may include, for example, multiple buttons and a single light source. For example, portion 2010 may include buttons 2011-2014 and light source 2021. Portion 2010 may include any number of buttons (e.g., five, six, ten, twelve). Light source 2012 may emit light whenever a button is pressed. In doing so, for example, a user may be able to receive information indicative of a proper button press. Light source 2021 may emit light of two or more colors. For example, light source 2021 may emit three colors. The three colors may be, for example, GREEN, RED, and ORANGE. A button press may cause light source 2021 to emit light of the color ORANGE. The input of a proper PIC/PIN may cause light source 2021 to emit light of the color GREEN. The input of an improper PIC/PIN may cause light source 2021 to emit light of the color RED.

Figure 21:
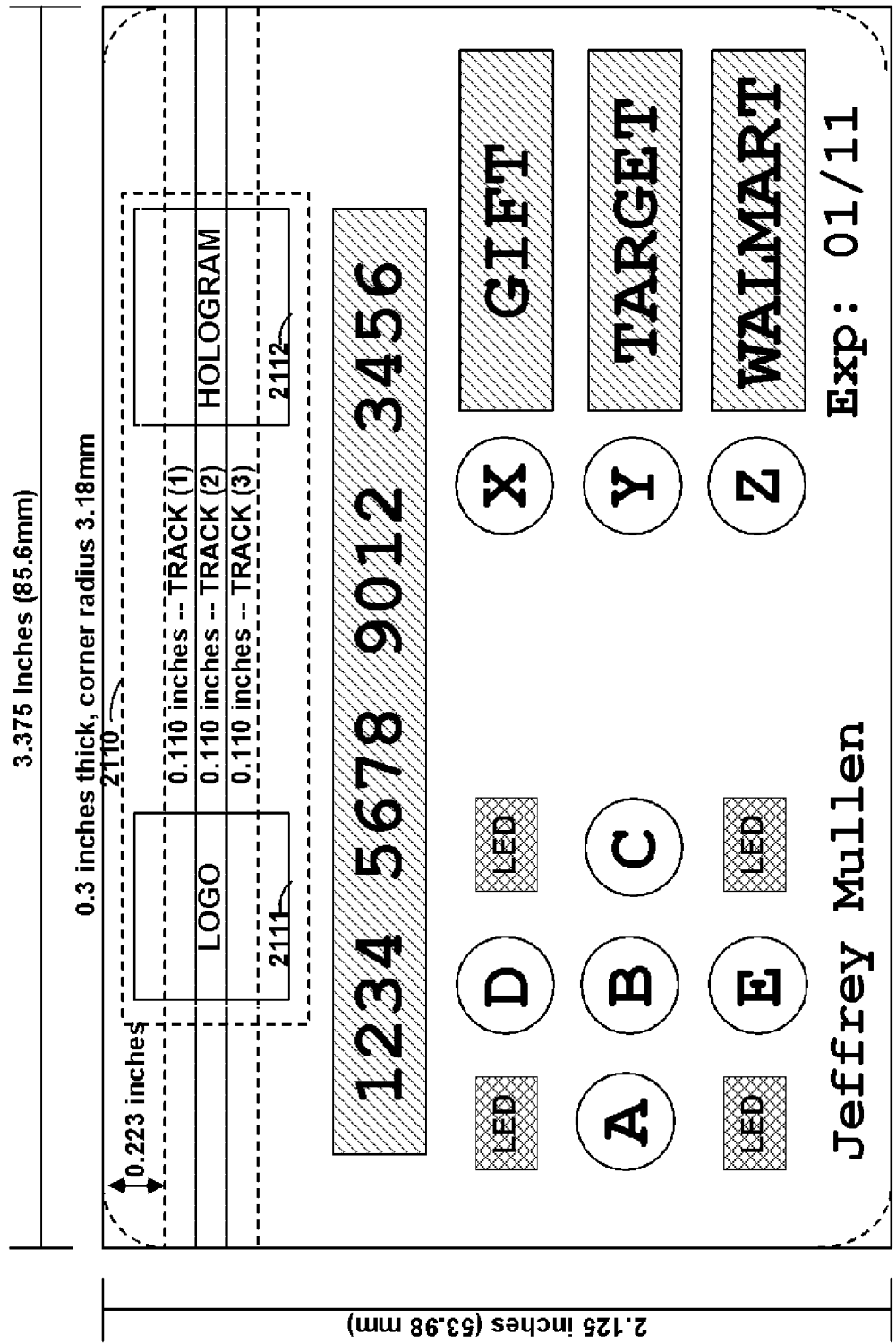

FIG. 21 shows card 2100 that may include, for example, portion 2110. Portion 2110 may be included, for example, over a magnetic emulator and/or encoder. For example, portion 2110 may include logo 2111 and hologram 2112. One or more magnetic emulators, for example, may be provided in card 2100 such that logo 2111 and hologram 2112 may be provided on, or printed upon, one or both surfaces of card 2100 about the magnetic emulator. In doing so, for example, the area of a card surface that a card issuer may personalize may be increased. Persons skilled in the art will appreciate that multiple tracks of data may be communicated to a magnetic stripe reader via one or more emulators. For example, two tracks of data may be communicated by two emulators. As per another example, three tracks of data may be communicated by three emulators.

Figure 22:
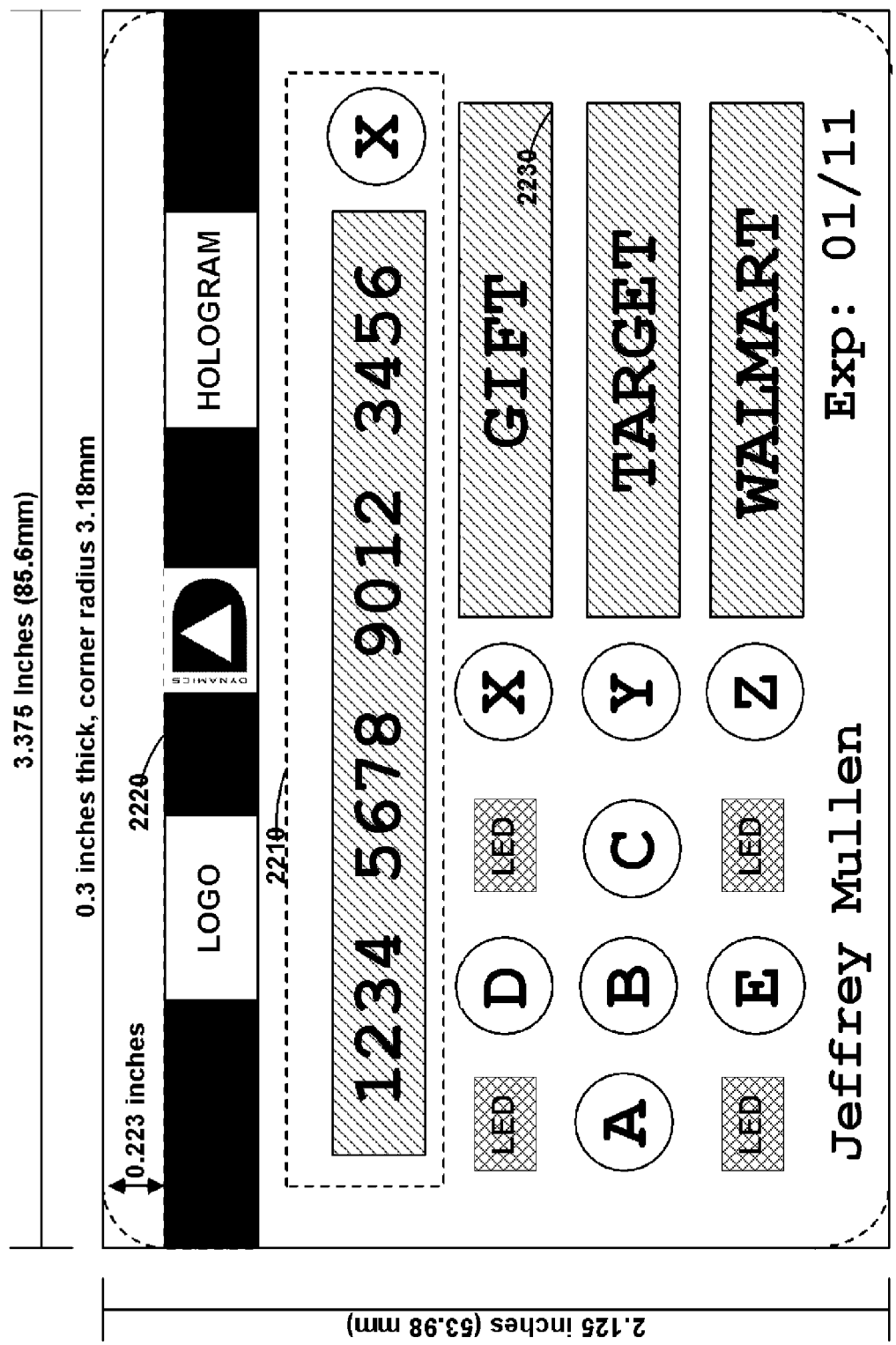

FIG. 22 shows card 2200. Card 2200 may include, for example, printed stripe indicia 2220. Stripe indicia 2220 may be printed on an area over one or more magnetic emulators. Stripe indicia 2220 may be printed such that a user recognizes how to properly swipe card 2220 in a reader. Card 2200 may also include portion 2210. Portion 2210 may include, for example, a display and a button. The display of portion 2210 may display a payment card number when an associated button is pressed or, for example, when an appropriate PIC/PIN is entered into a card. The display of portion 2210 may be longer than the length of ⅔rds the length of a card. Display 2220 may also be included and may have a length between ½ and ⅓ the length of card 2200.

Figure 23:
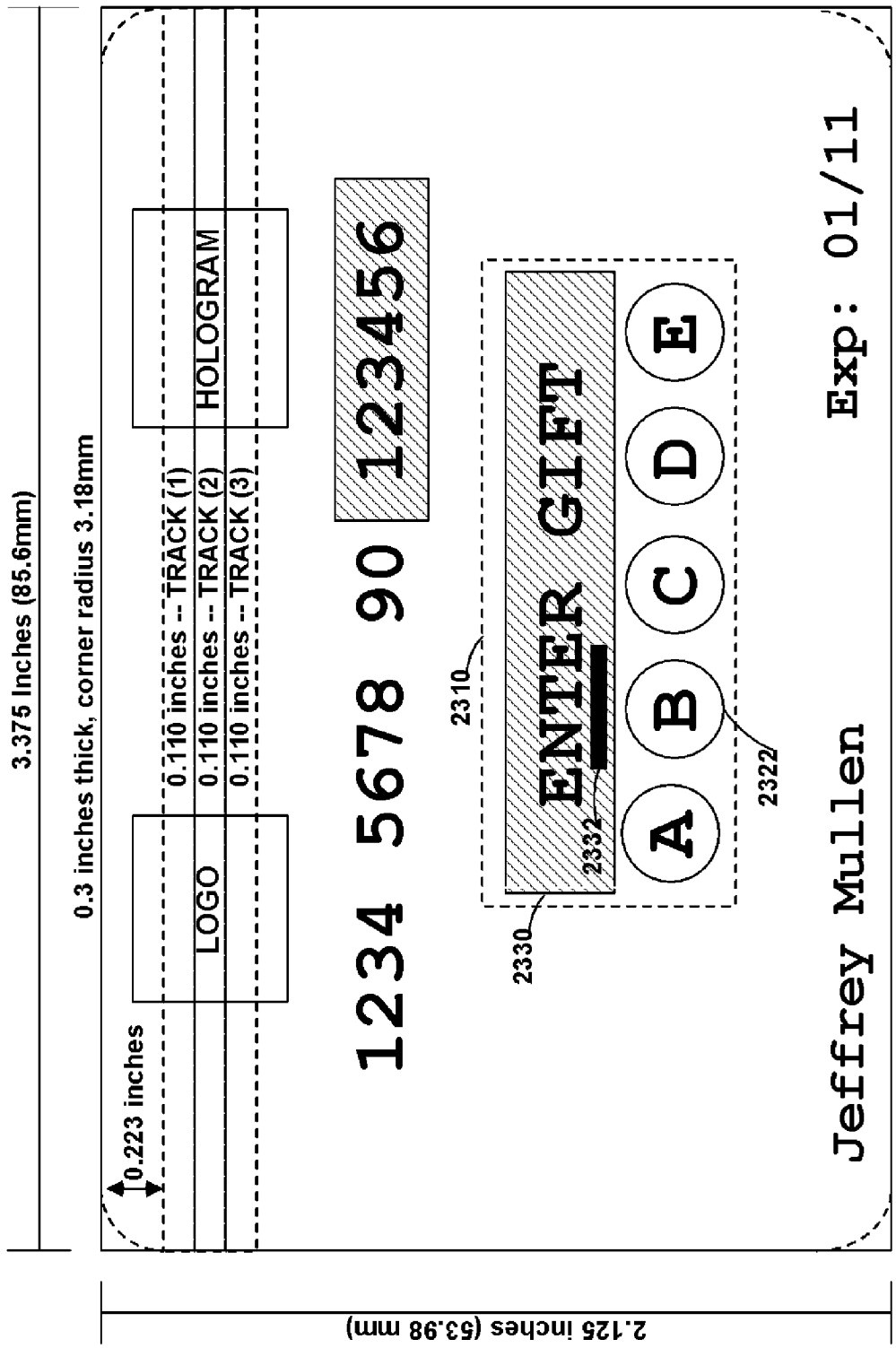

FIG. 23 shows card 2300. Card 2300 may include, for example, portion 2310. Portion 2310 may include, for example, display 2330 and multiple buttons. Button 2322 may be included. Each button of portion 2310 may be associated, for example, with different data that can be displayed on display 2330. When a particular button of portion 2310 is pressed, display 2330 may, for example, display indicia representative that a user has pressed that particular button. For example, the activation of button 2322 may cause, for example, indicia 2332 to be displayed in addition to information associated with button 2322. Accordingly, for example, a user may not only be acknowledged that a button was pressed, but also the particular button that was pressed. Furthermore, for example, power may be conserved as both the information associated with a button and the indicia indicative of a button press may be provided by the same display device. Portion 2310 may include buttons that are aligned along an edge of a display.

Figure 24:
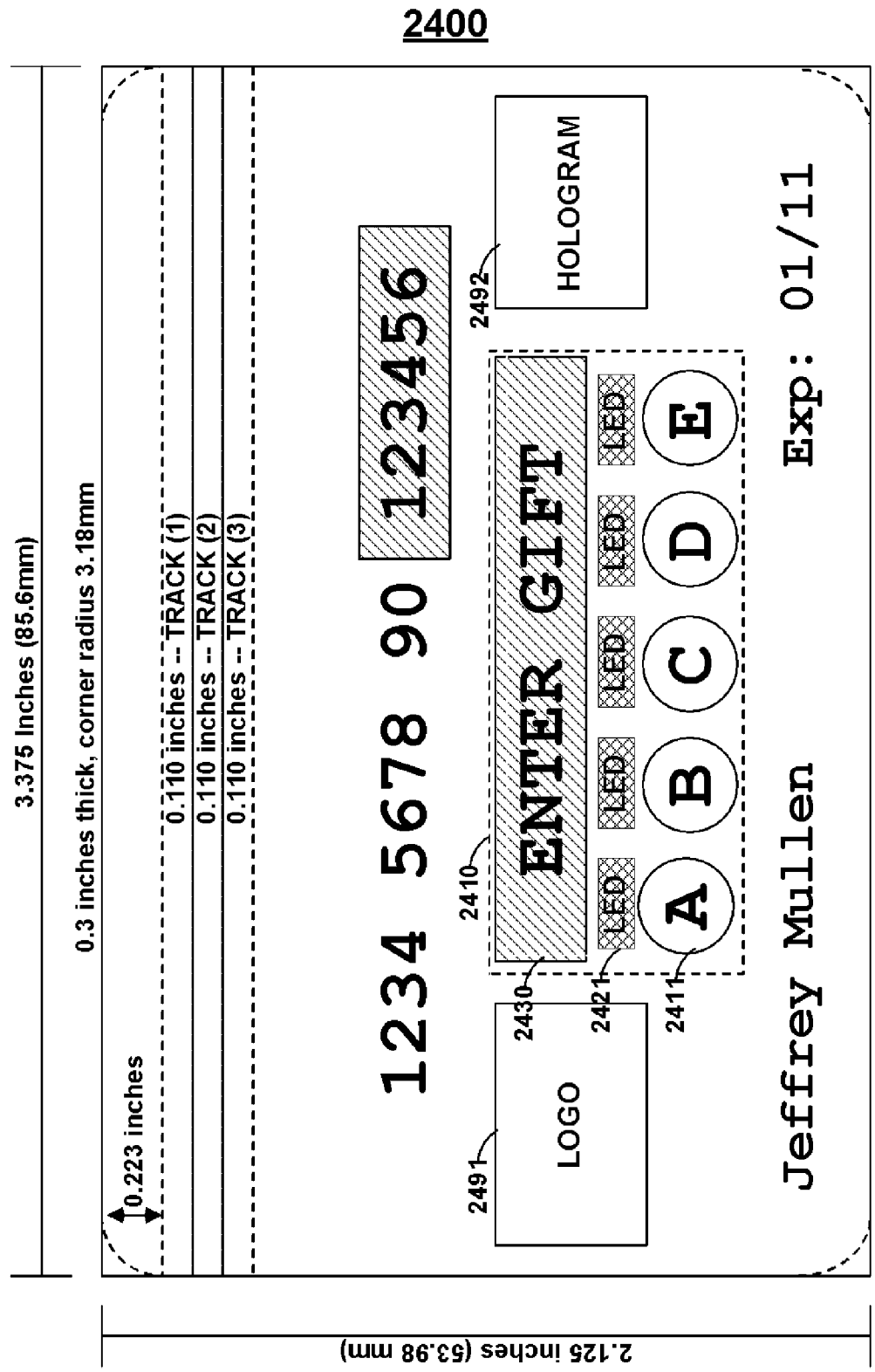

FIG. 24 shows card 2400 that may include portion 2410. Portion 2410 may include display 2430 and a multitude of buttons and light sources. For example, a light source may be provided for every button located in portion 2410. The activation of a button of portion 2410 may cause, for example, display 2430 to display particular information associated with the button activation. Additionally, the activation of button 2411 may cause associated light source 2421 to emit light. Light source 2421 may emit light for a particular period of time (e.g., less than a second, more than a second, more than five seconds). Light source 2421 may periodically emit light to indicate to a user that button 2411 has been activated by the user. Logo 2491 may be located on one side of portion 2410 and hologram 2492 may be located on the other side of portion 2410.

Figure 25:
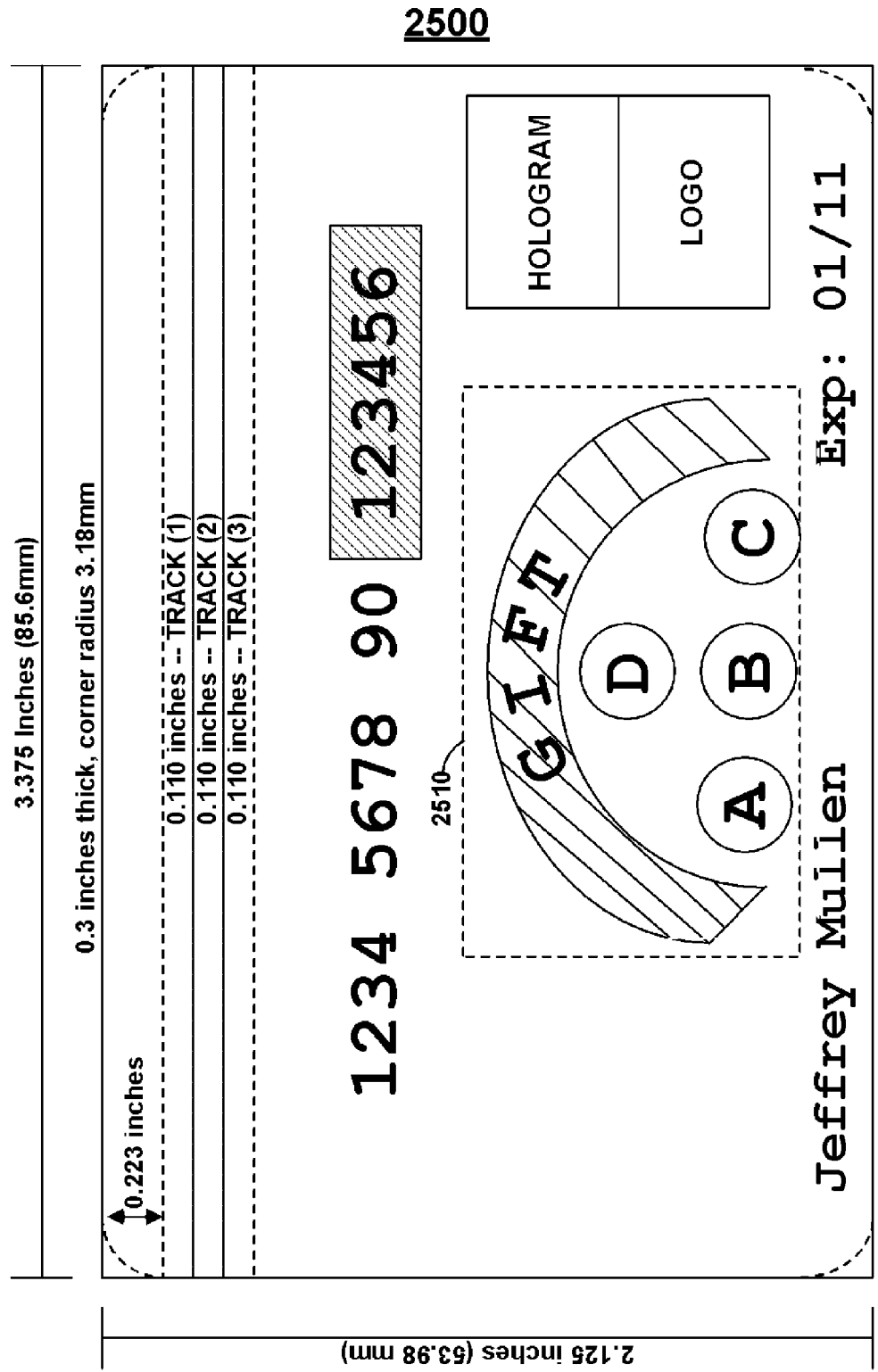

FIG. 25 shows card 2500 that may include portion 2510. Portion 2510 may include a display having one or more curved edges. Such displays may be, for example, LCD and/or electrochromic displays.

Figure 26:
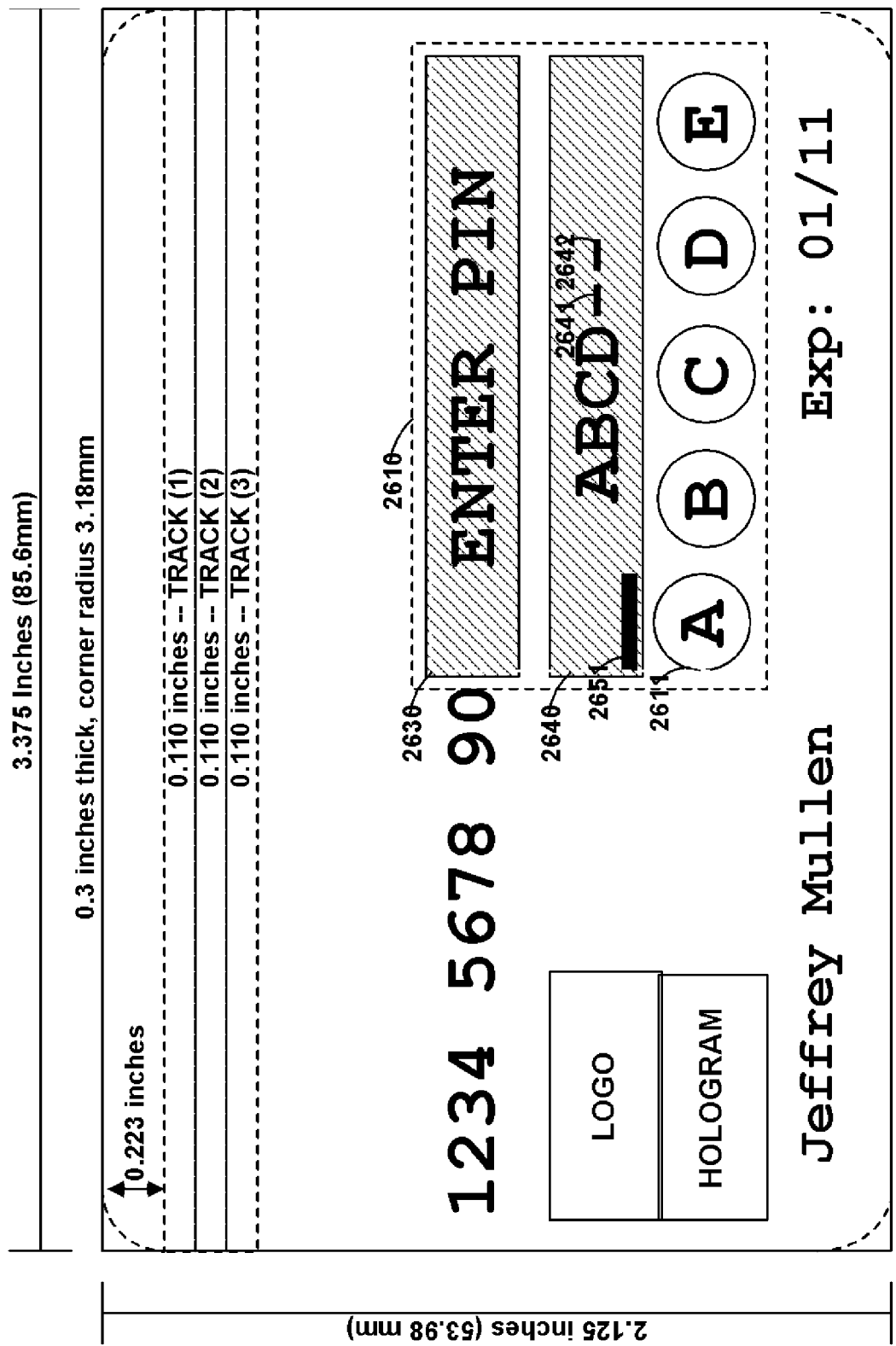

FIG. 26 shows card 2600 that may include portion 2610. Portion 2610 may include, for example, display 2630 and display 2640. A button press may, for example, result in information associated with the function of a button to be displayed in display 2630. Display 2640 may then be utilized, for example, to show the string of subsequent button presses. For example, a user may utilize button 2611 to indicate that a PIC is desired to be entered. Indicia 2651 may be displayed to denote that the function associated with button 2611 has been activated. Indicia 2641 and 2642 may be utilized to show the number of button entries needed to complete the function. As buttons are entered such indicia may change to indicia representative of the pressed buttons. After all buttons associated with a function have been entered, the function of the buttons of portion 2610 may be utilized to determine the next function (instead of, for example, information entry). Other functions may include, for example, amount desired for cash-back, amount desired for ATM withdrawal, tip percentage, amount to be charged to debit, and the amount to be charged to credit.

Persons skilled in the art will appreciate that a card may, for example, allow a user to enter in how much of a transaction is desired to be paid with a particular account. For example, a user may divide payment between a checking account and a savings account. Alternatively, for example, a user may divide payment between two or more credit accounts. Alternatively still, for example, a user may divide payment between a credit account and a debit account.

Figure 27:
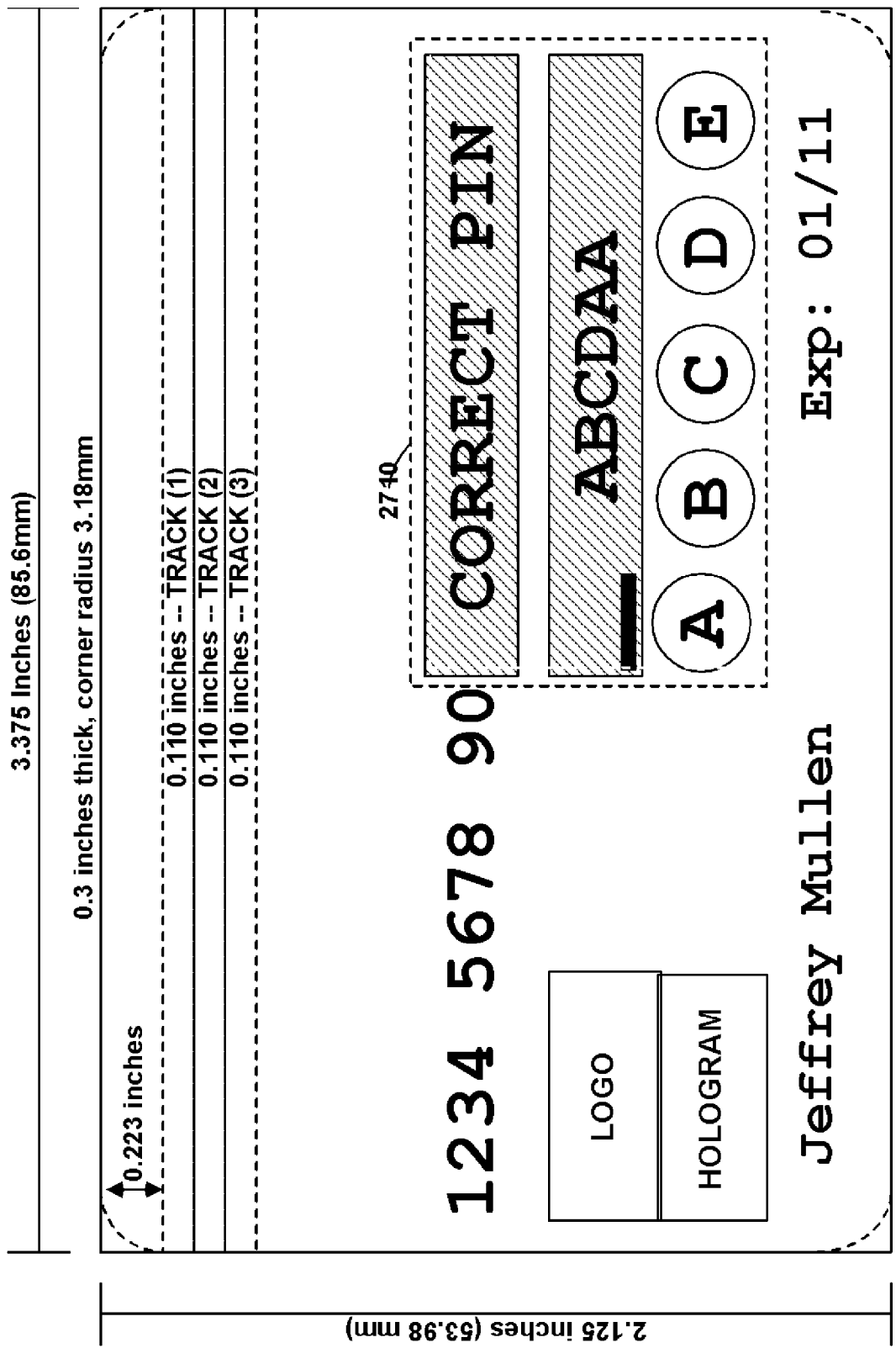

FIG. 27 shows card 2700 that may include portion 2700. Portion 2700 may include a display that, for example, provides information indicative of whether an entered PIN/PIC was correct or incorrect.

Figure 28:
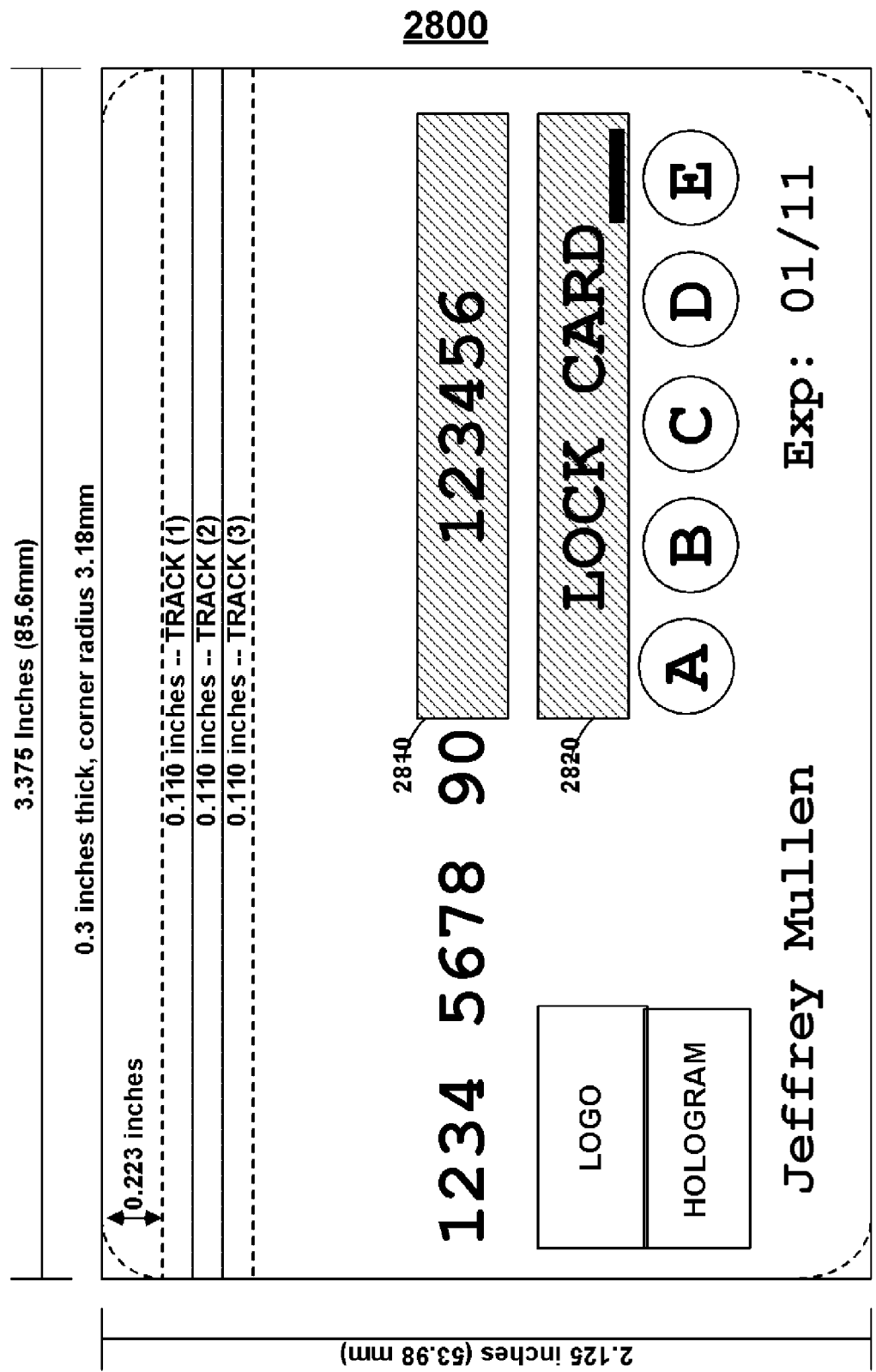

FIG. 28 shows card 2800 that may include, for example, display 2810 and display 2820. Display 2810 may, for example, be utilized to display a portion of a card number. Display 2820 may be utilized, for example, to display the various states of operation of a card. For example, display 2820 may be utilized to ask the user whether the user desires to lock a card.

Figure 29:
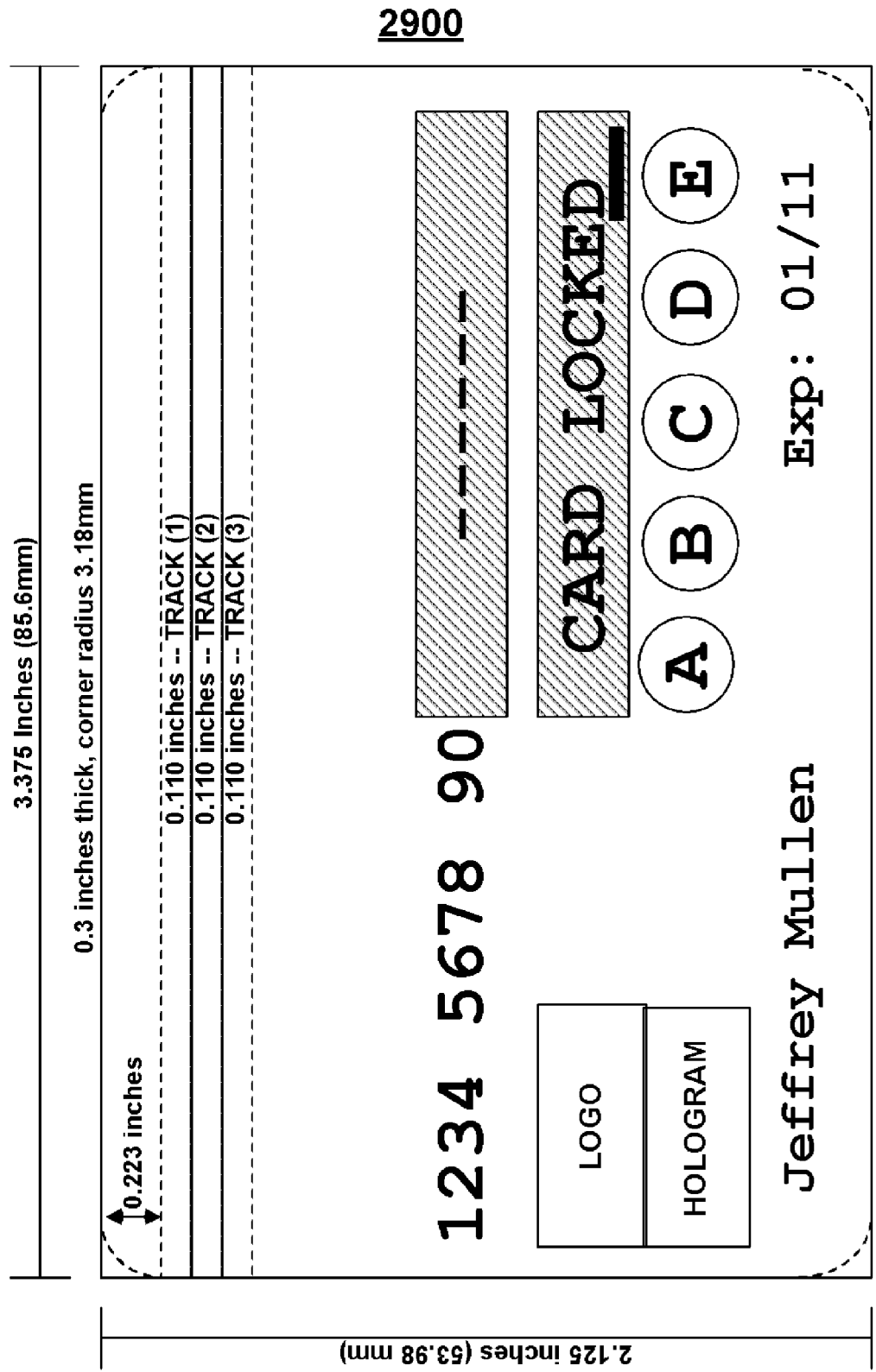

FIG. 29 shows card 2900 that may include, for example, display 2910 and display 2920. Display 2910 may, for example, be utilized to display a portion of a card number until a card is locked. Display 2920 may be utilized to indicate to a user that a card is locked and requires an appropriate PIC/PIN to unlock the card. A user may lock his/her card at anytime by providing the appropriate manual input to a card. A card may lock after a period of time of non-activity by a user. A card may lock and require an administrative unlock code if, for example, a particular number of consecutive incorrect PICs/PINs were entered into a card. Such an administrative unlock code may be obtained, for example, via a phone call to the appropriate card issuer or via a visit to a website of the appropriate card issuer.

Figure 30:
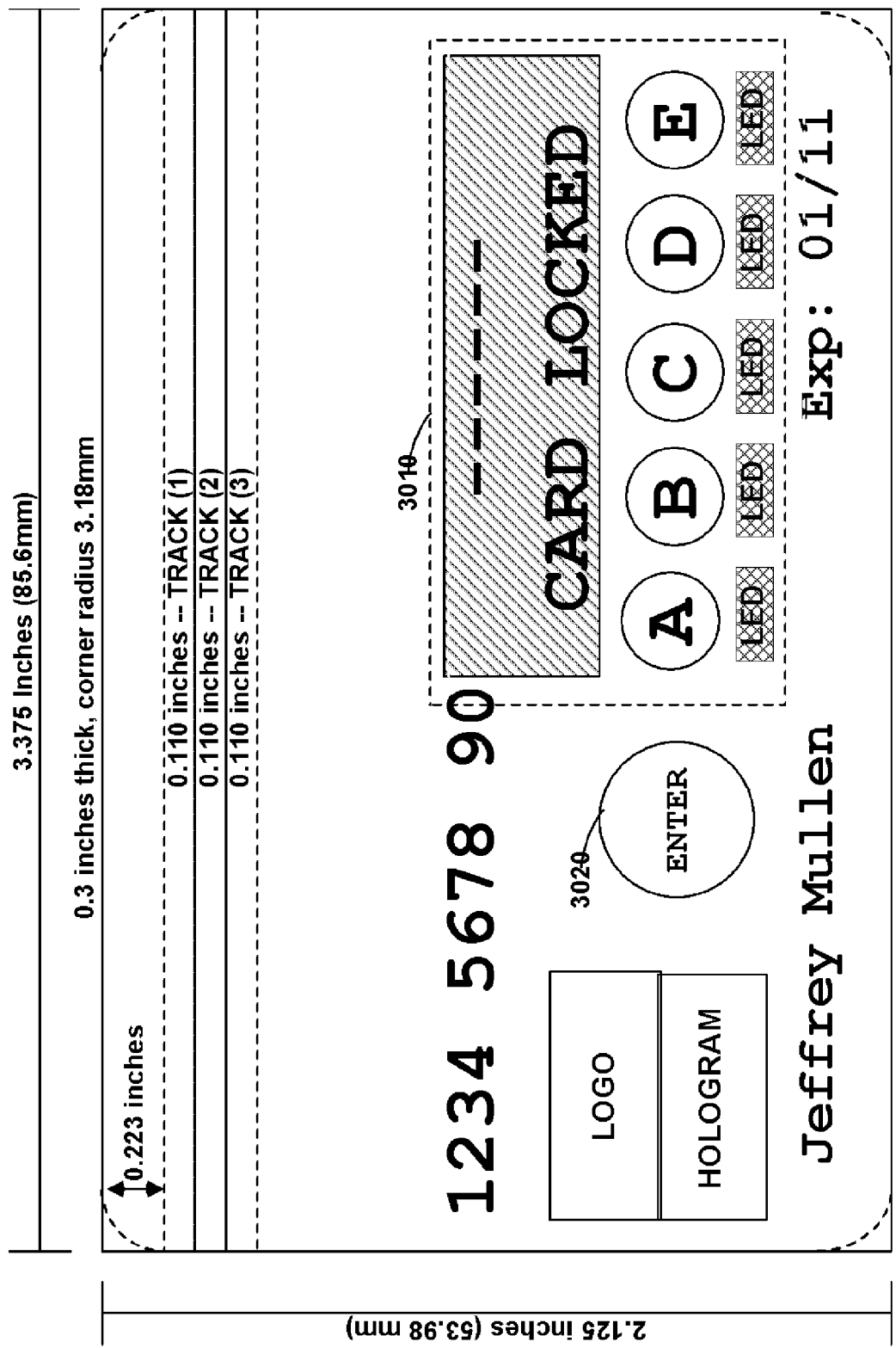

FIG. 30 shows card 3000 that may include portion 3010. Portion 3010 may include a multiple line display. Card 3000 may also include button 3020. Button 3020 may be, for example, larger than buttons in portion 3010. Such a button may be mechanical and/or capacitive. For example, button 3020 may be mechanical while other buttons located on card 3000 are capacitive. Accordingly, for example, more force may be needed to activate button 3020 than other buttons. Accordingly, for example, a user may press button 3020 in order to, for example, bring a processor of card 3000 out of hibernation such that a user may enter in a PIC/PIN. Accordingly, for example, card 3000 may automatically expect the entry of a PIN/PIC after activation of button 3020.

Figure 31:
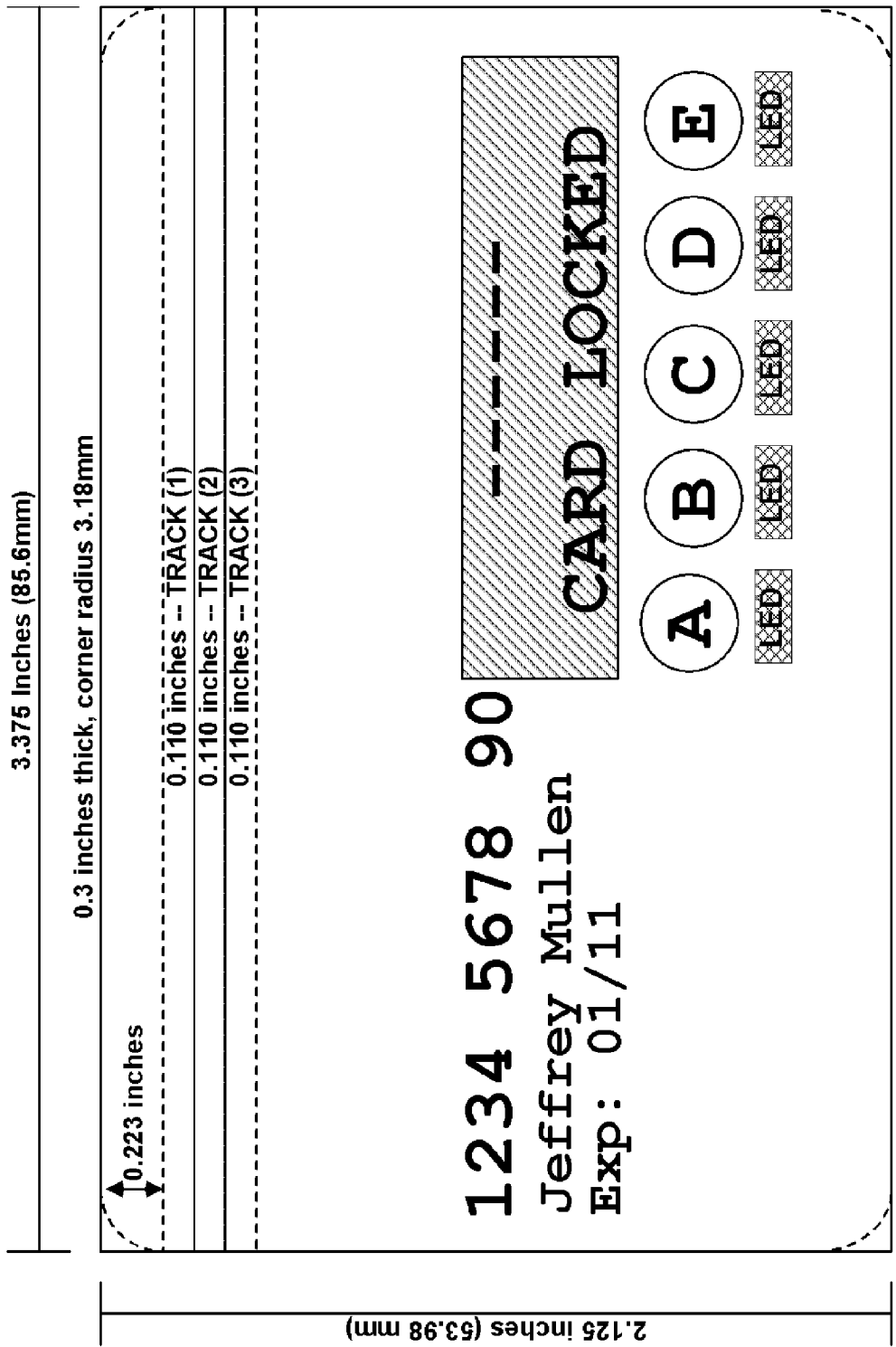

FIG. 31 shows card 3100 that may include, for example, a multiple line display where one of the lines of the display may display a portion of a payment card number.

Figure 32:
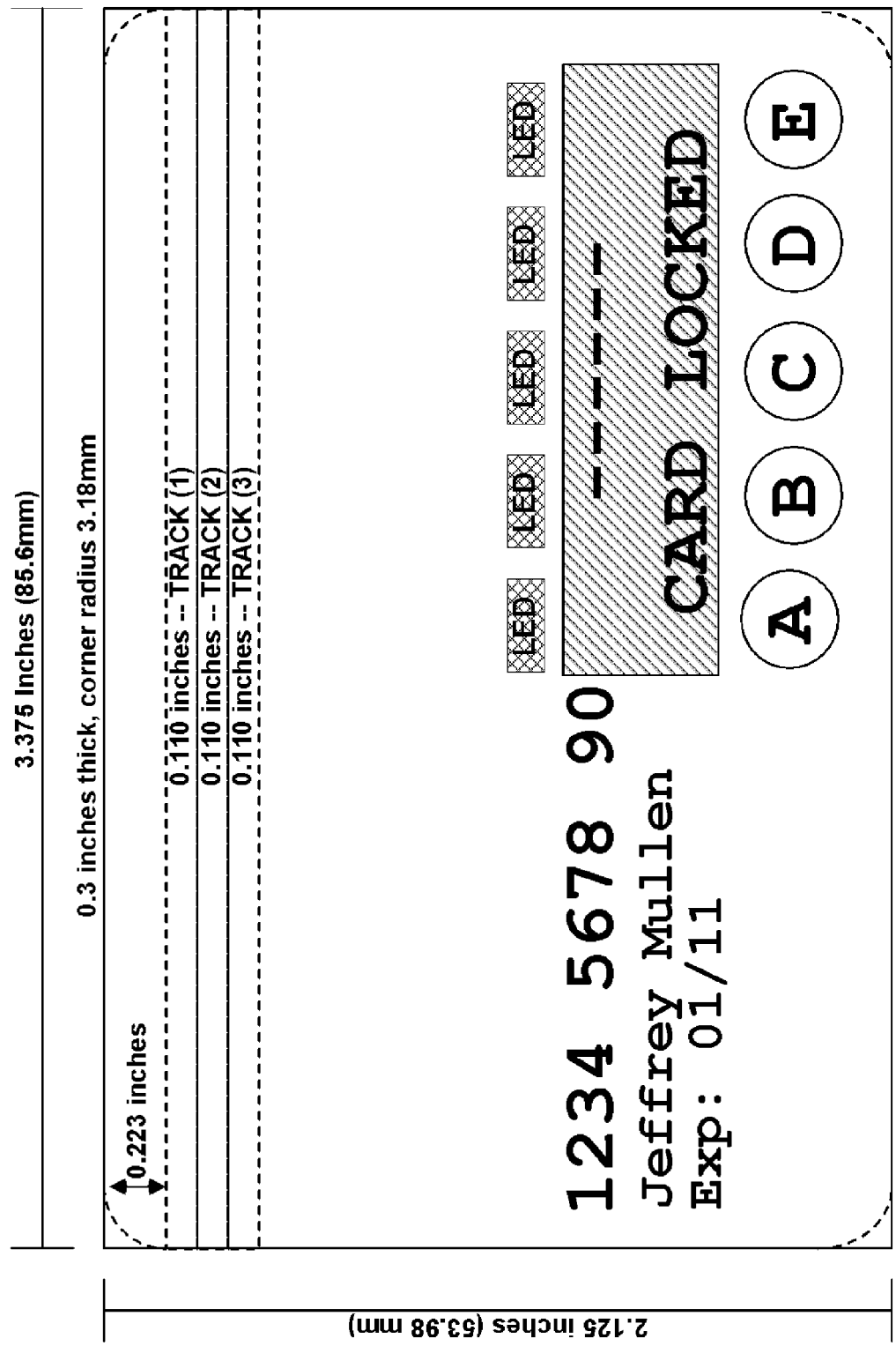

FIG. 32 shows card 3200 that may include, for example, a row of light sources above a multiple line display. The multiple line display may be located above, for example, a row of buttons.

Figure 33:
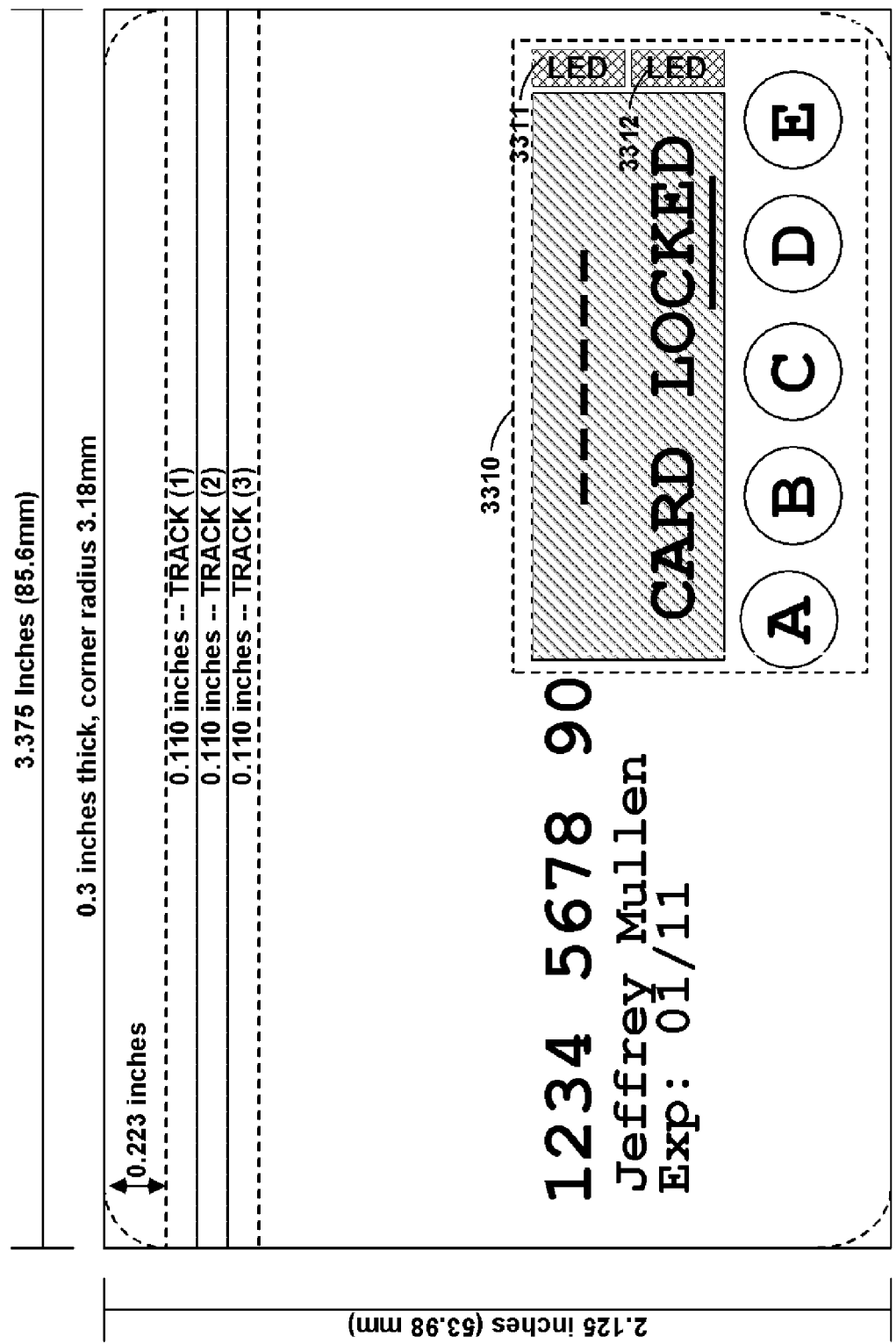

FIG. 33 shows card 3300 that may include, for example, portion 3310 that may include a multiple line display, buttons, and light sources 3311 and 3312. Light sources 3311 and 3312 may be aligned with, for example, a particular line of a multiple line display.

Figure 34:
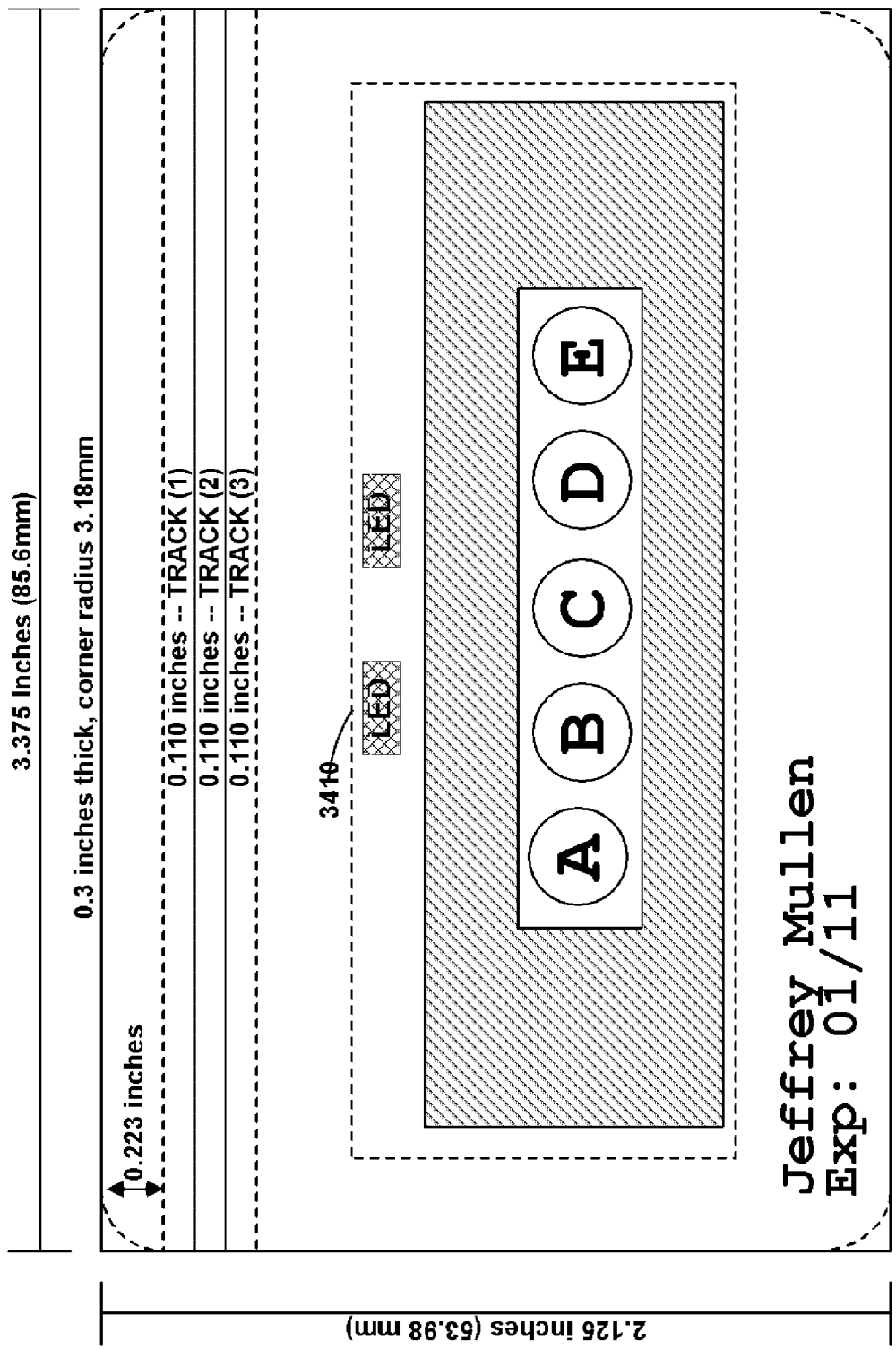

FIG. 34 shows card 3400 that may include, for example, portion 3410. Portion 3410 may include multiple buttons and light sources. Portion 3410 may also include a display with a non-display portion in its center. Buttons may be located in such a non-display portion.

Figure 35:
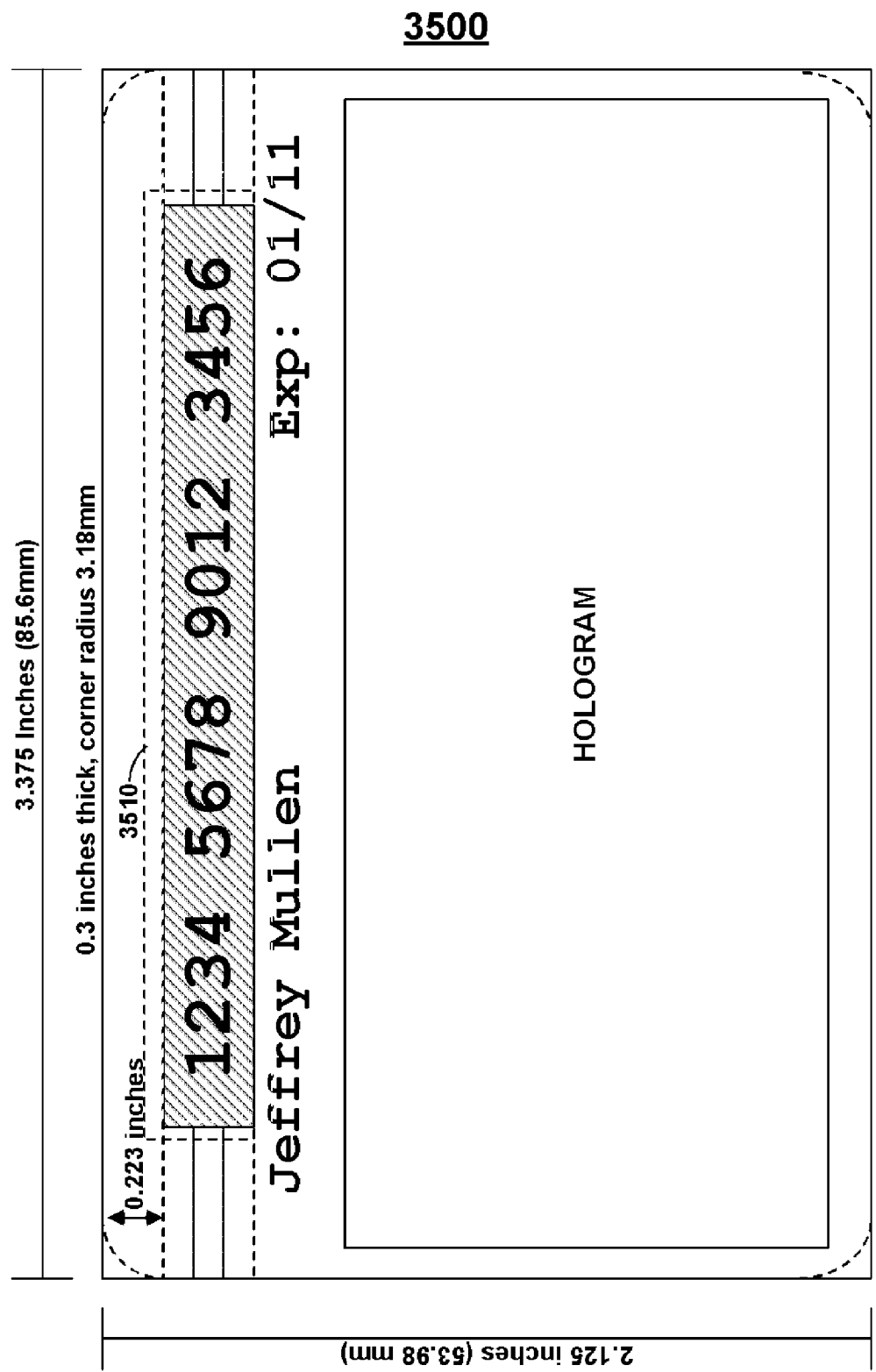

FIG. 35 shows card 3500. Card 3500 may include, for example, portion 3510 that may include a display (as well as buttons and light sources). A display may be provided, for example, over one or more magnetic emulators. For example, a magnetic emulator may be provided on one or more middle layers of a multiple layer PCB. A display may be provided, for example, on a surface layer of a multiple layer PCB or a different layer than the layers defining a magnetic emulator. By providing a display over a magnetic emulator, for example, the area that can be personalized may be increased. For example, a hologram or logo may be provided about more than ⅔rds the surface area of a surface of card 3500.

Figure 36:
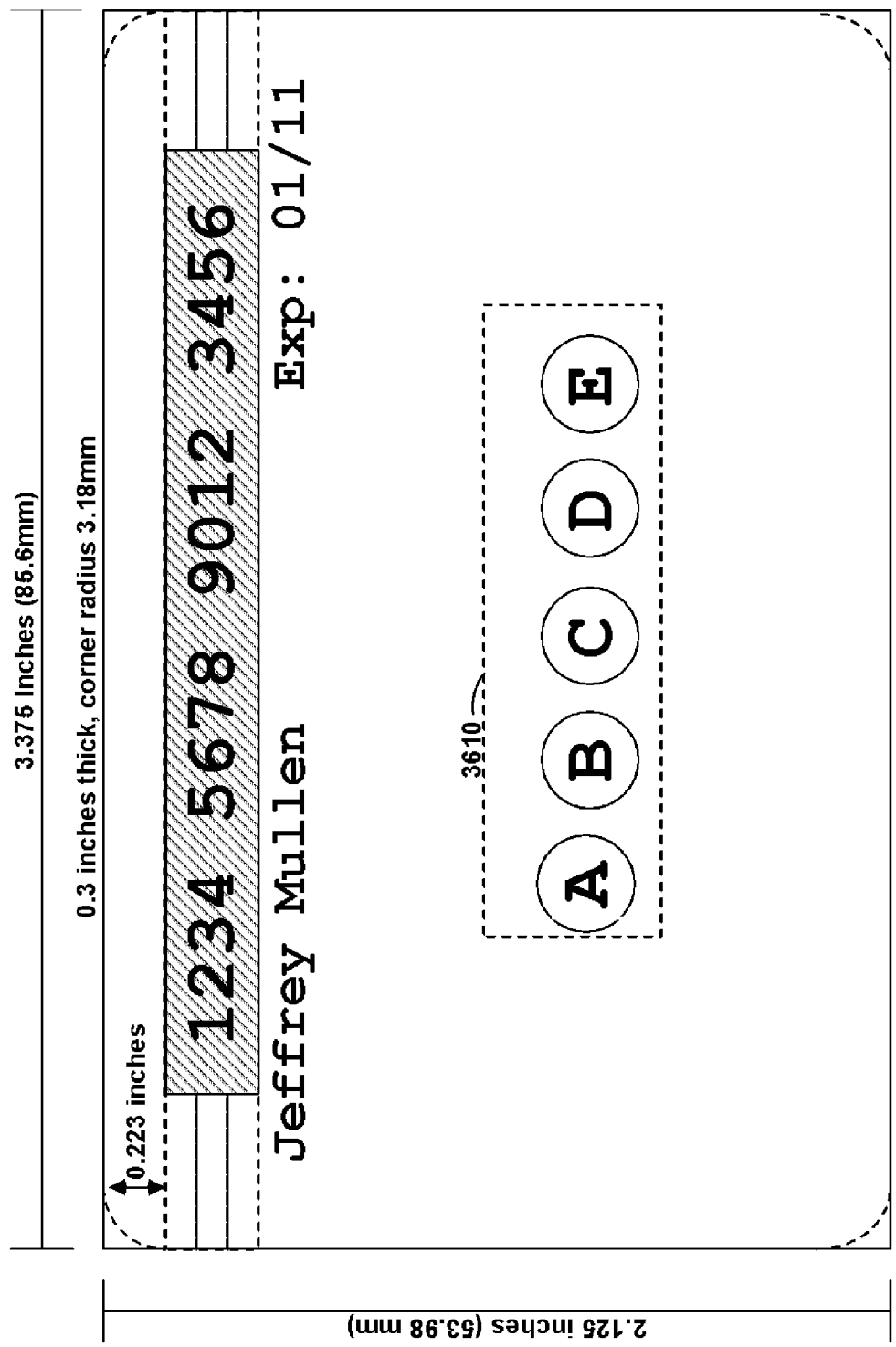

FIG. 36 shows card 3600 that may include portion 3610, which may include any number of buttons. For example, portion 3610 may include five buttons positioned in the center of card 3600 in a single row.

Figure 37:
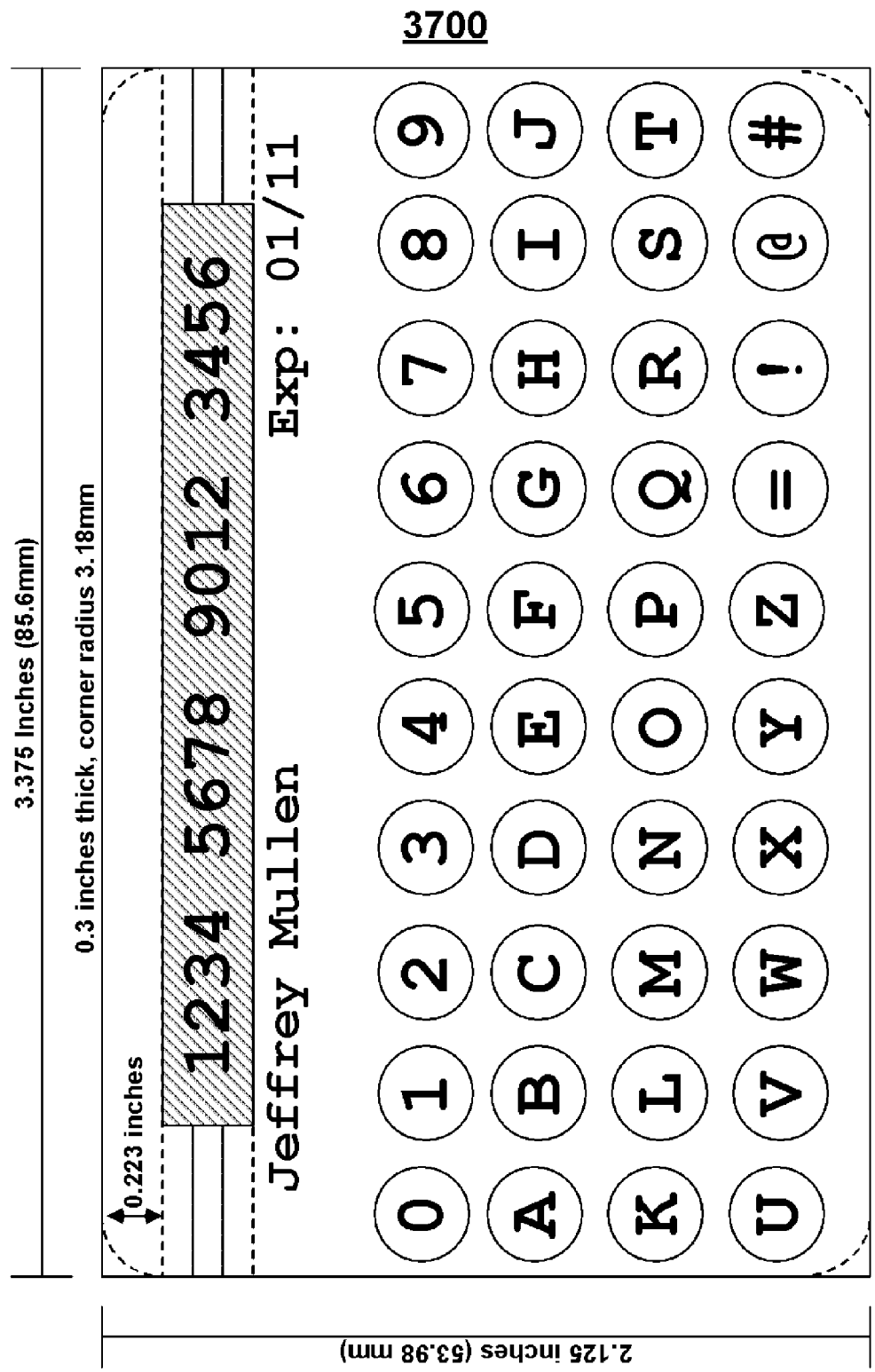

FIG. 37 shows card 3700 that may include over 26 buttons such that, for example, the entire alphabet may be represented by individual buttons. Buttons associated with a particular letter may also, for example, be associated with one or more numbers. Alternatively, for example, additional buttons may be provided for numbers as well as other characters.

Figure 38:
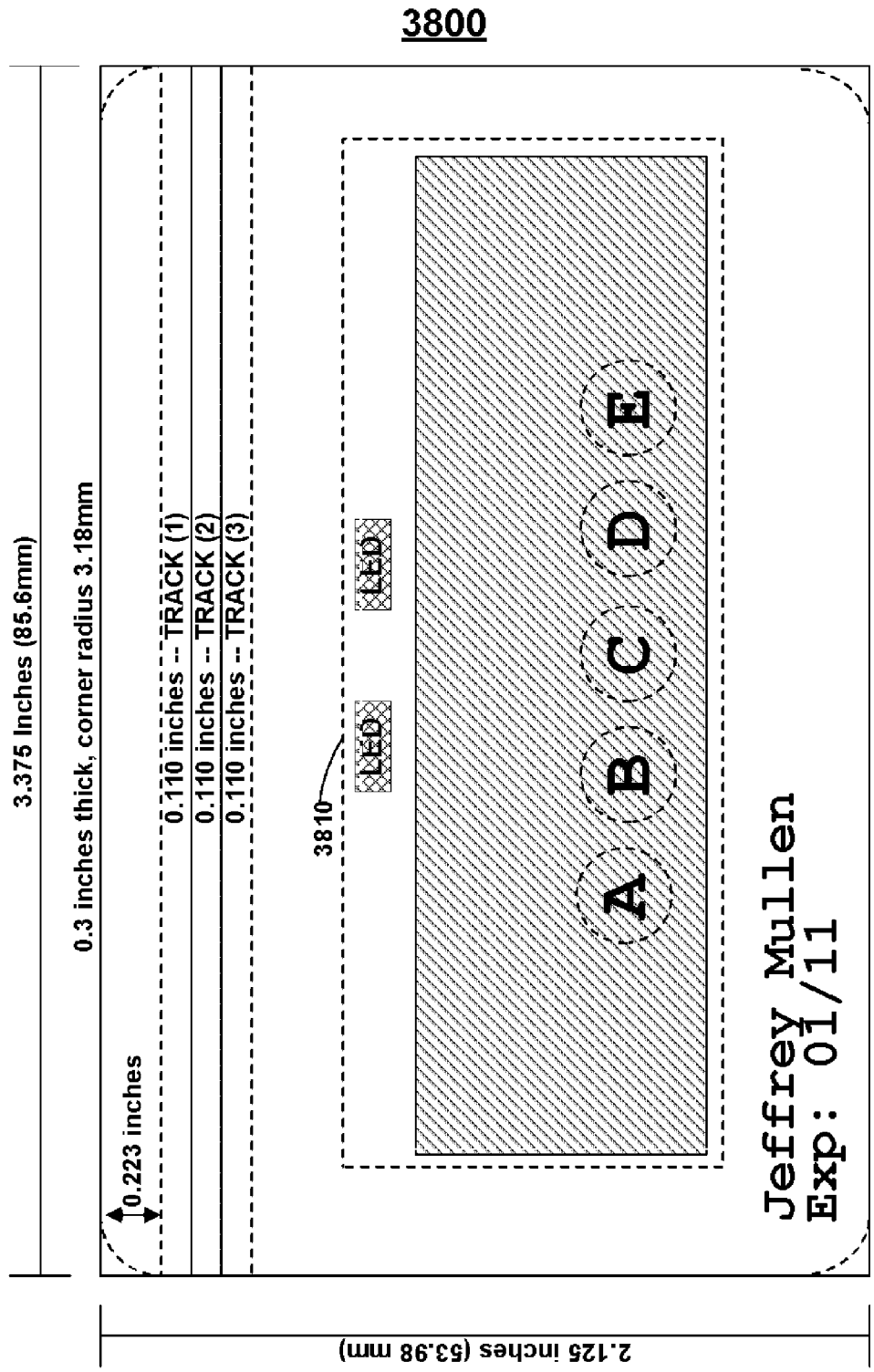

FIG. 38 shows card 3800 that may include portion 3810. Portion 3810 may include any number of buttons, light sources, or displays. Any display provided may, for example, be a touch-sensitive display. Accordingly, for example, such a touch-sensitive display may display indicia representative of areas of touch. Accordingly, each area of touch may be discerned as different manual input by a processor coupled to the touch-sensitive display. A touch-sensitive display may, for example, be provided as an electrochromic display with electrodes that are coupled to a capacitive sensor. Accordingly, for example, the electrodes may cause indicia to appear on the display in the shape of the electrodes, the capacitance of which may also change as a user's finger approaches the proximity of the electrode. A display may, for example, include five capacitive touch areas for receiving manual input.

Figure 39:
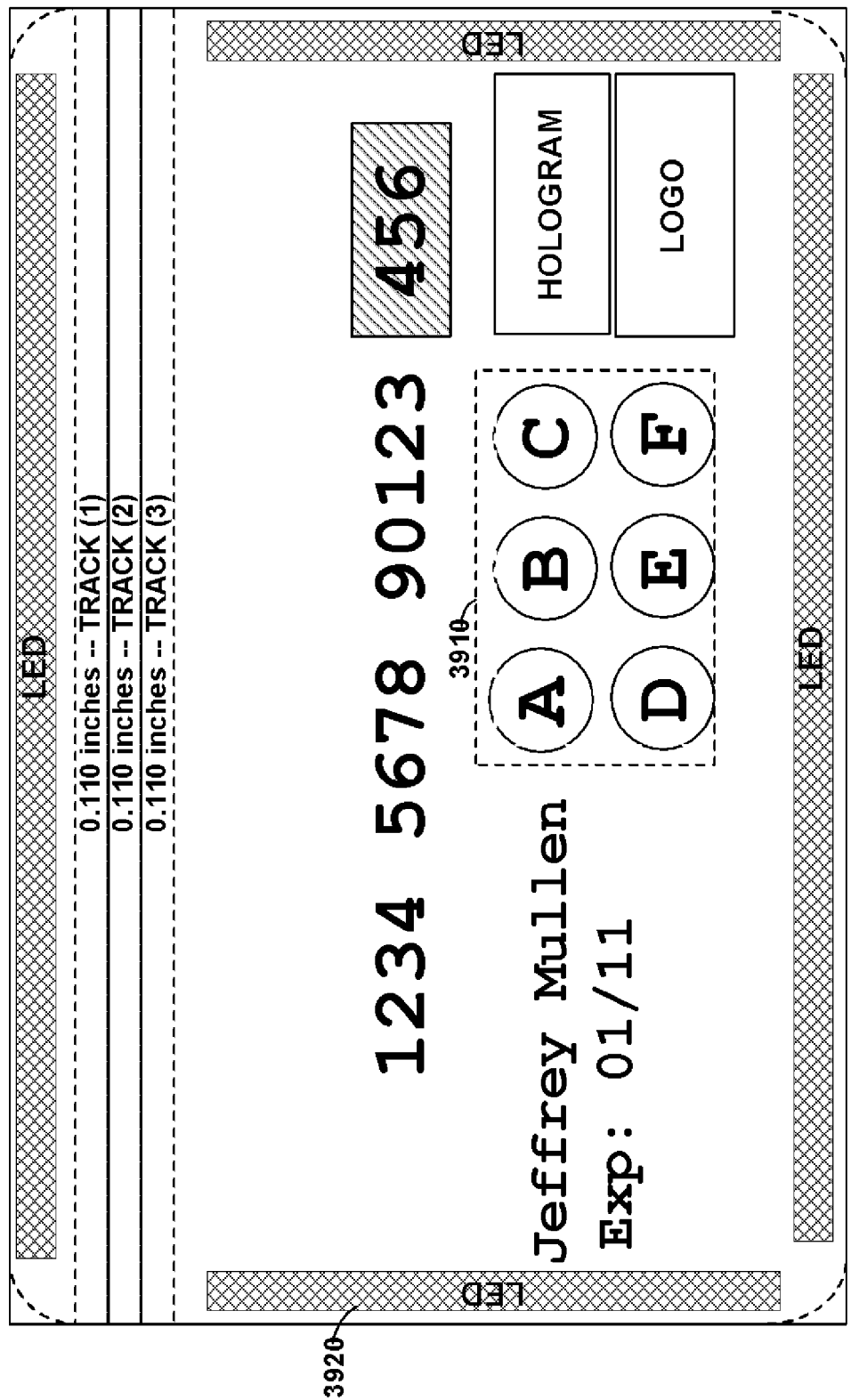

FIG. 39 shows card 3900 that may include, for example, button array 3910. Button array 3910 may include, for example, two rows of centered buttons. Each row may include, for example, three buttons. Light sources may be provided along each edge of a card. For example, light source 3920 may be provided along an edge of a card. A card may be laminated with transparent laminate.

Figure 40:
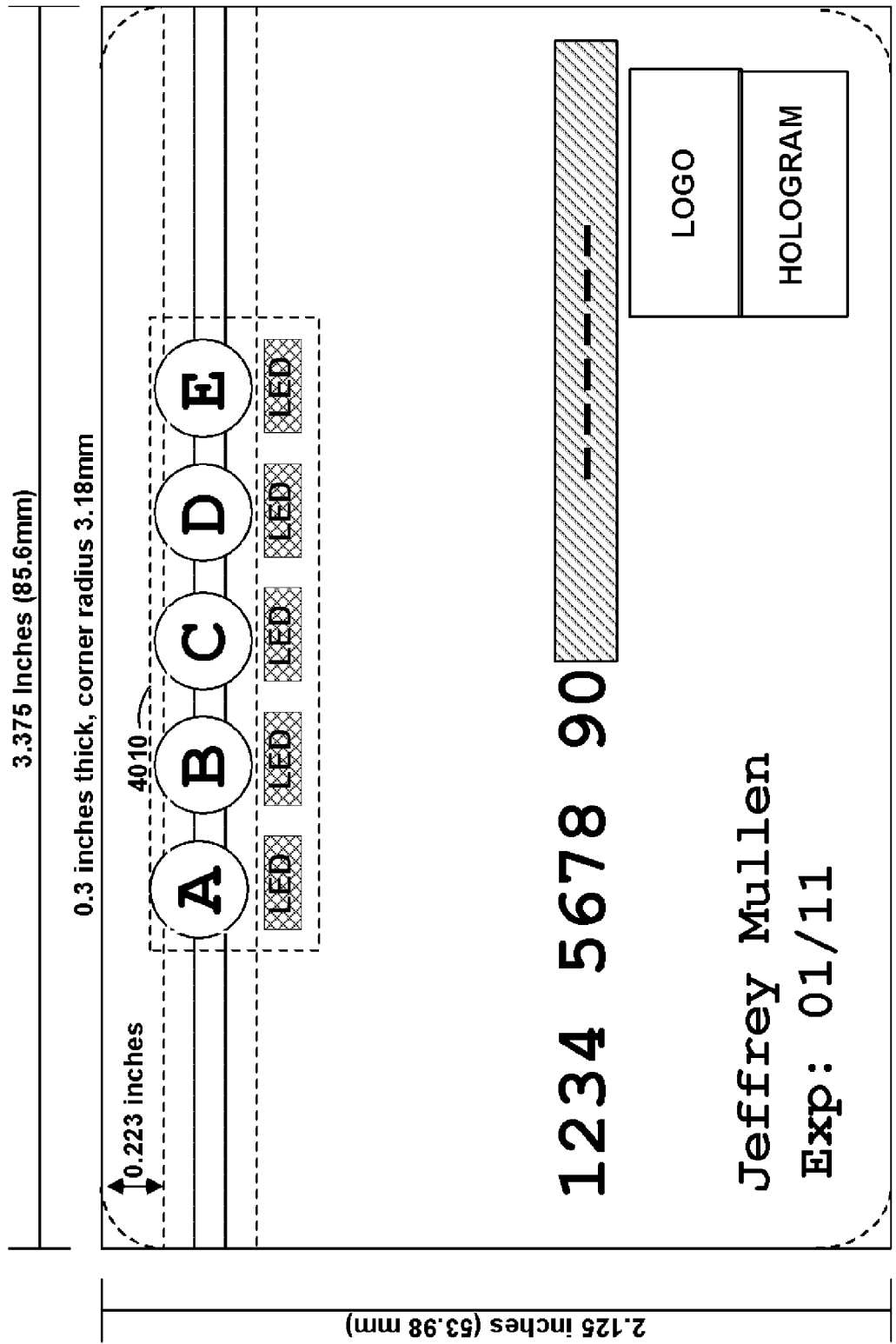

FIG. 40 shows card 4000 that may include, for example, portion 4010. Portion 4010 may include a row of buttons and light sources and may be provided over one or more magnetic emulators.

Figure 41:
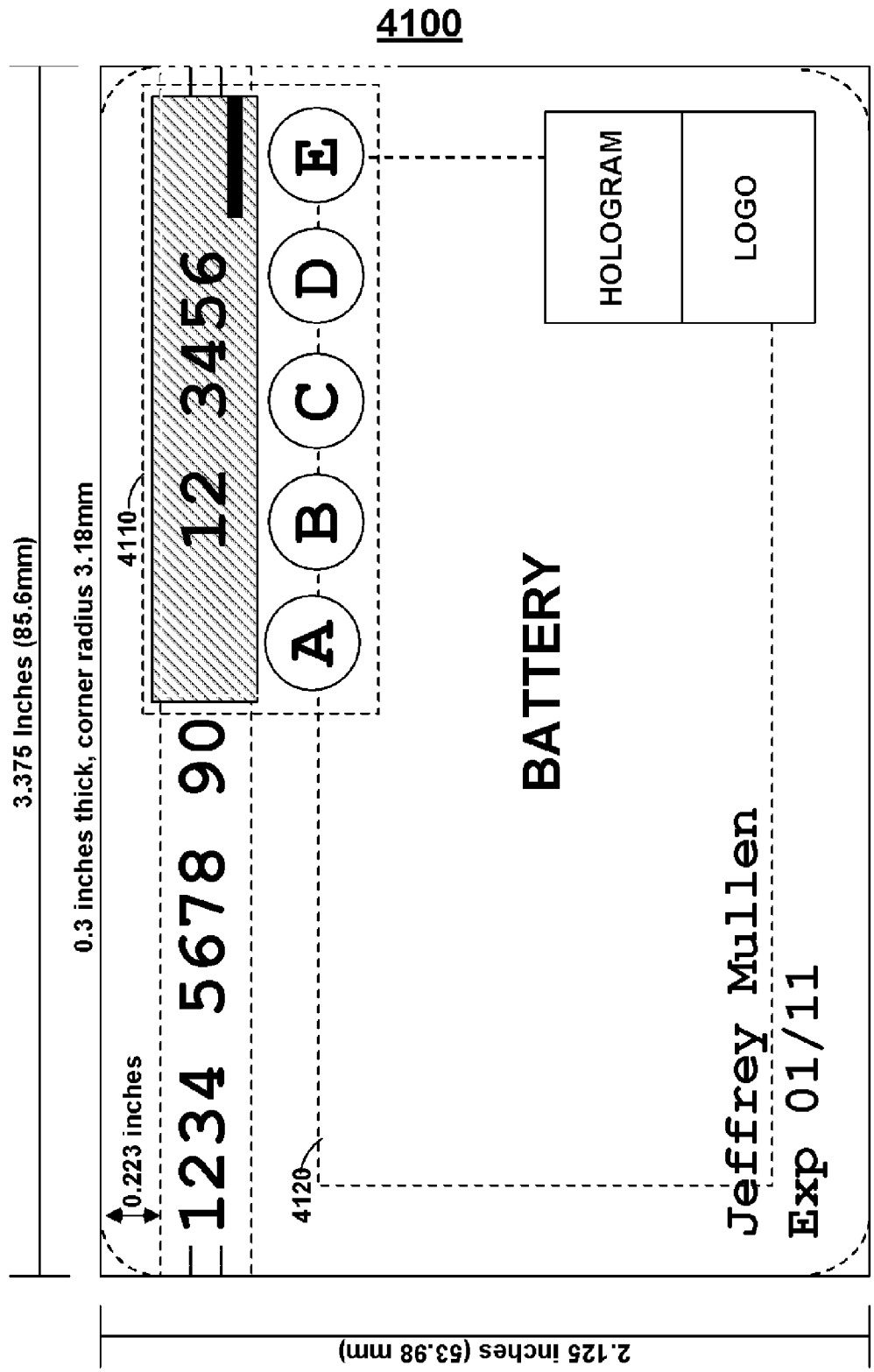

FIG. 41 shows card 4100 that may include portion 4110 at least partially located over one or more magnetic emulators or in line with a magnetic stripe read-head should card 4100 be swiped through a magnetic stripe reader such that card 4100 may transmit data to a magnetic read-head of the magnetic stripe reader through one or more magnetic emulators. Card 4100 may include, for example, battery 4120. Battery 4120 may, for example, span across a surface area of card 4100 that is greater than ⅔rds of the surface area of card 4100.

Figure 42:
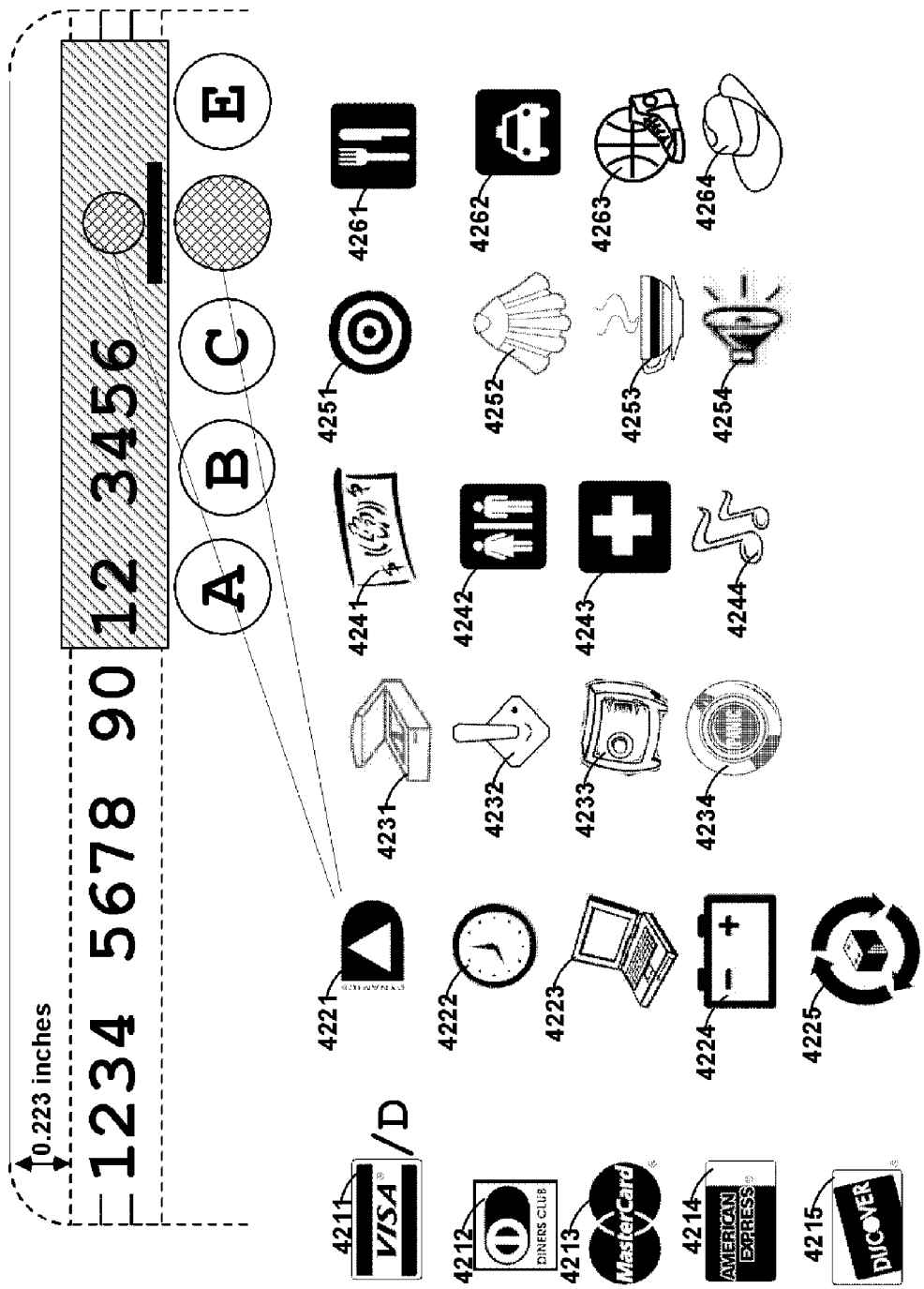

FIG. 42 shows card portion 4200 that may include a display. Various symbols may be provided on a display. Such various symbols may also be, for example, printed on a user interface (e.g., a button). Furthermore, the various symbols may be displayed on a display as part of a capacitive touch area.

Indicia 4211-4215 may be provided to signify different card issuers. Indicia 4211-4215 may take the form of corporate logos. Indicia 4221 may be utilized with a button, for example, to display a card number such as a dynamic card number. Indicia 4221 may take the form of a logo. A button may include both a symbol and one or more letters and/or numbers. Indicia 4222 may be utilized with a button, for example, to display the time. Indicia 4222 may take the form of, for example, a clock. Indicia 4223 may be utilized with a button, for example, a code for an online purchase. Indicia 4223 may take the form of, for example, a computer. Indicia 4224 may be utilized with a button, for example, to display the remaining battery power. Indicia 4224 may take the form of, for example, a battery. Indicia 4225 may be utilized by a microprocessor when a battery is low and the card or battery needs replacement. Indicia 4225 may take the form of a battery and another symbol (e.g., a recycling symbol). Alternatively, for example, indicia 4225 may take the form of an empty battery.

Indicia 4231 may be utilized with a button, for example, in order to signal to the microprocessor that a user desires to upload data. Indicia 4231 may take the form of, for example, a scanner or light reader. Accordingly, for example, a light sensor located on card 4200 may be utilized to receive light-based information. Indicia 4232 may be utilized with a button, for example, to initiate a game on the card. Indicia 4232 may take the form of, for example, a joystick. Indicia 4233 may be utilized with a button, for example, to lock a card (e.g., until an appropriate PIN/PIC is entered). Indicia 4233 may take the form of, for example, a safe. Indicia 4234 may be utilized with a button, for example, to add information in discretionary data indicative of a user warning. Such a warning may take many forms. For example, if a user is held at gunpoint at an ATM to withdraw money, the user may press a panic button on the card and the information may be communicated through the payment interchange to a server that may identify that a panic button was pressed. Accordingly, for example, the authorities (e.g., police) may be contacted and provided with the location of the reader from which the panic information was communicated. Indicia 4234 may take the form of, for example, a panic button.

Indicia 4241 may be utilized with a button, for example, to indicate that a user desires to withdraw cash. Indicia 4241 may take the form of, for example, money. Indicia 4242 may be utilized with a button, for example, to indicate the user of card 4200. For example, a card may be utilized by both a husband and a wife. A button may be utilized to toggle between the user such that the appropriate user's PIN/PIC can be recognized. Accordingly, for example, a card may operate different depending on the user of the card. For example, a husband may have one spending limit and a wife may have a different spending limit. Indicia 4242 may take the form of, for example, a man and a woman. Indicia 4243 may be utilized with a button, for example, to indicate that a user is in need of medical attention due to a medical emergency. Accordingly, for example, a card may communicate such information (e.g., via discretionary data) via a card reader. Indicia 4243 may take the form of, for example, a medical cross. Indicia 4244 may be utilized with a button, for example, to play a tone. Such a tone may be a song or a clip from a song. Such a tone may also be, for example, an identifying audible sound that may be forwarded to a remote server for identity recognition. Indicia 4244 may take the form of, for example, a musical note.

Indicia 4251-4253 may be utilized with a button, for example, to utilize a payment card associated with a particular store. Indicia 4251-4253 may take the form of, for example, a logo of a store such as a target, a shell, or a cup of coffee. Indicia 4254 may be utilized with a button, for example, to change the volume of a speaker of a card. Indicia 4254 may take the form of, for example, a speaker.

Indicia 4261-4264 may be utilized with a button to denote the type of purchase that was made. Such information may be communicated with payment data (e.g., via discretionary data) such that a user's bill may be organized based on the types of purchases a user indicated at the time of purchase. Indicia 4261-4264 take the form of, for example, a knife/form (e.g., for food), a car (e.g., for travel), a basketball (e.g., for entertainment), and a hat (e.g., for clothing).

Figure 43:
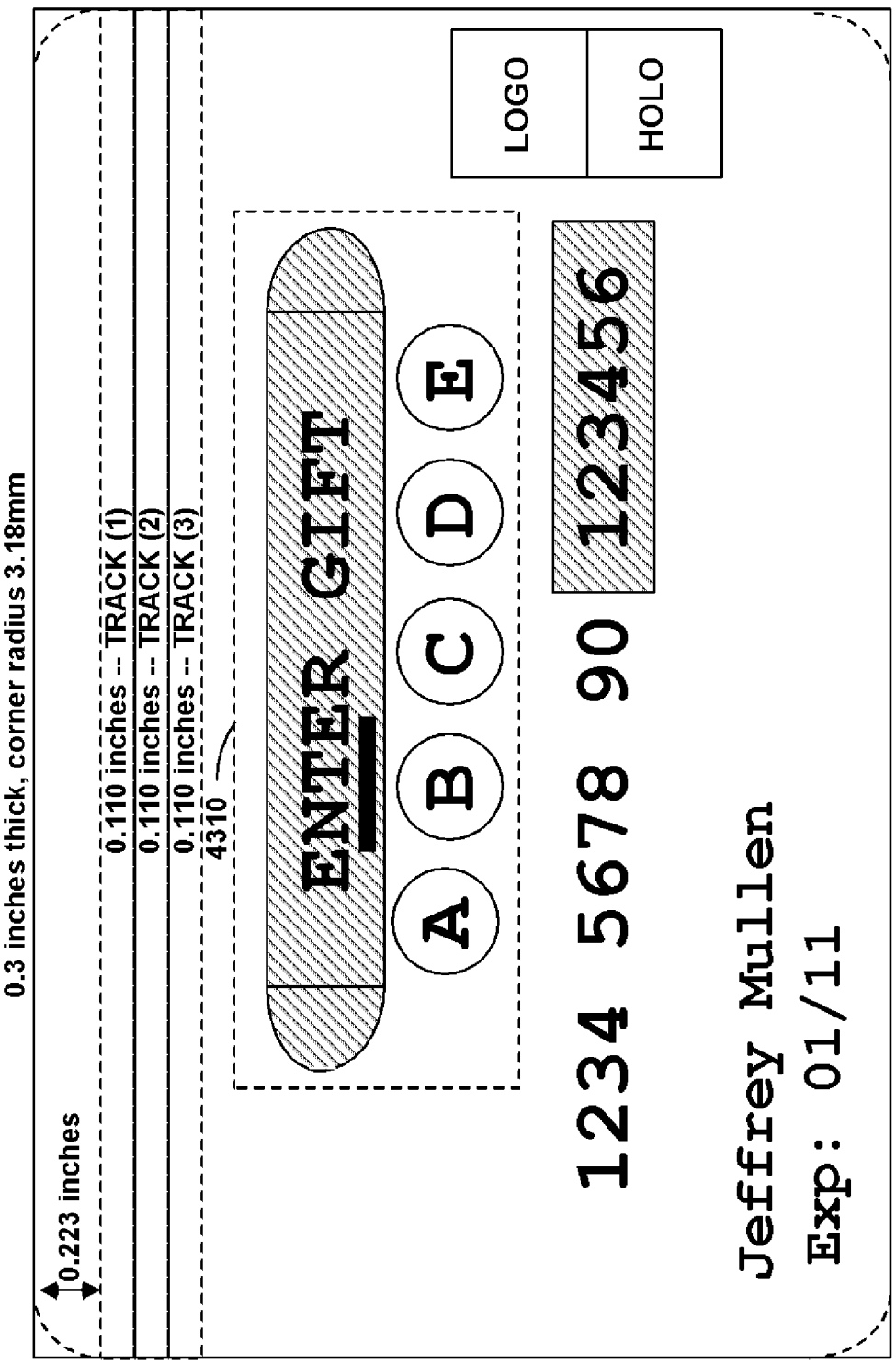

FIG. 43 shows card 4300 that may include portion 4310. Portion 4310 may include a display, for example, with rounded edges. Such a display may be, for example, in the shape of an oval.

Figure 44:
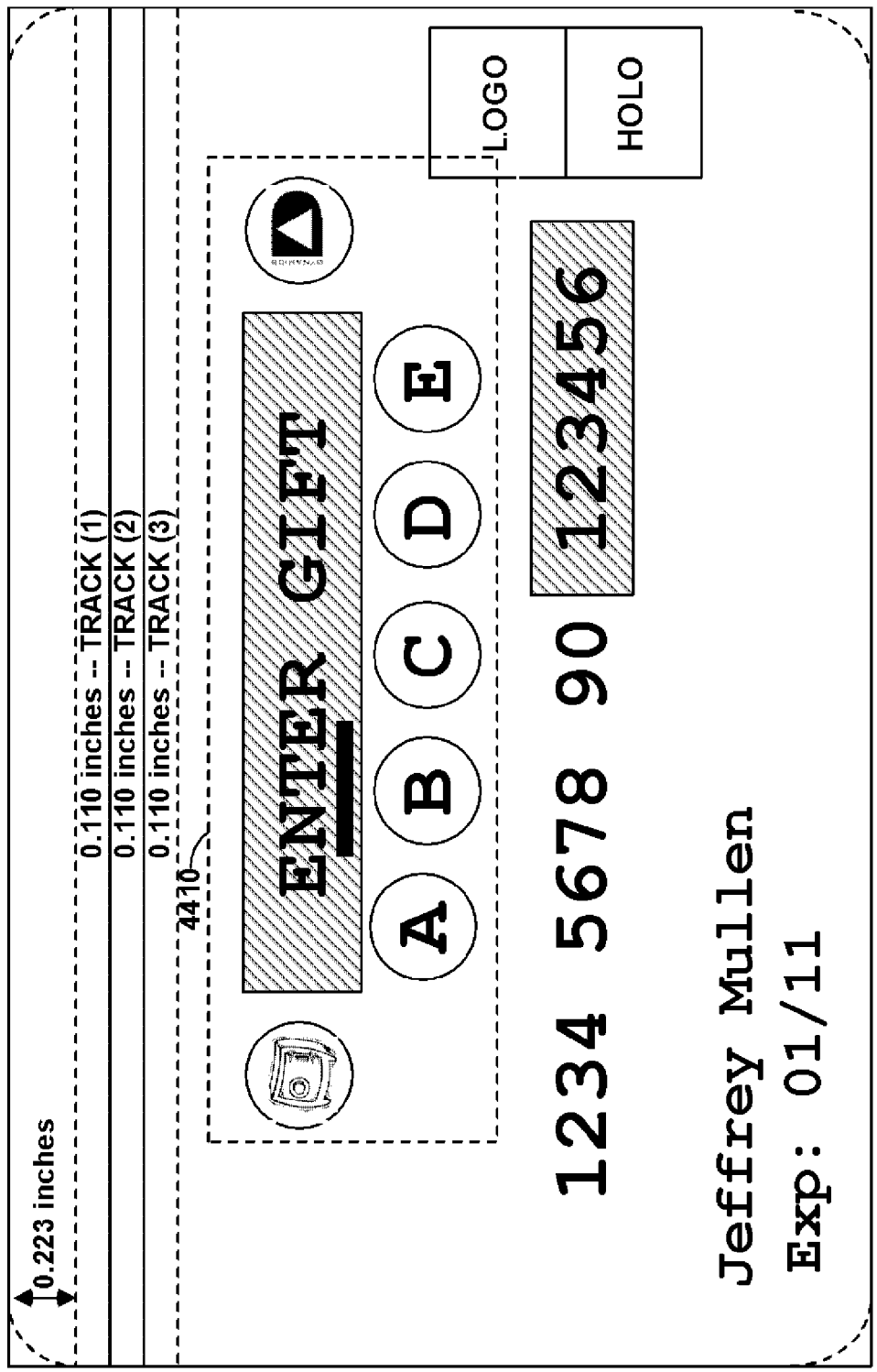

FIG. 44 shows card 4400 that may include portion 4410. Portion 4410 may include a display. Multiple buttons may be located below the display. A button may be located on each side of the display.

Figure 45:
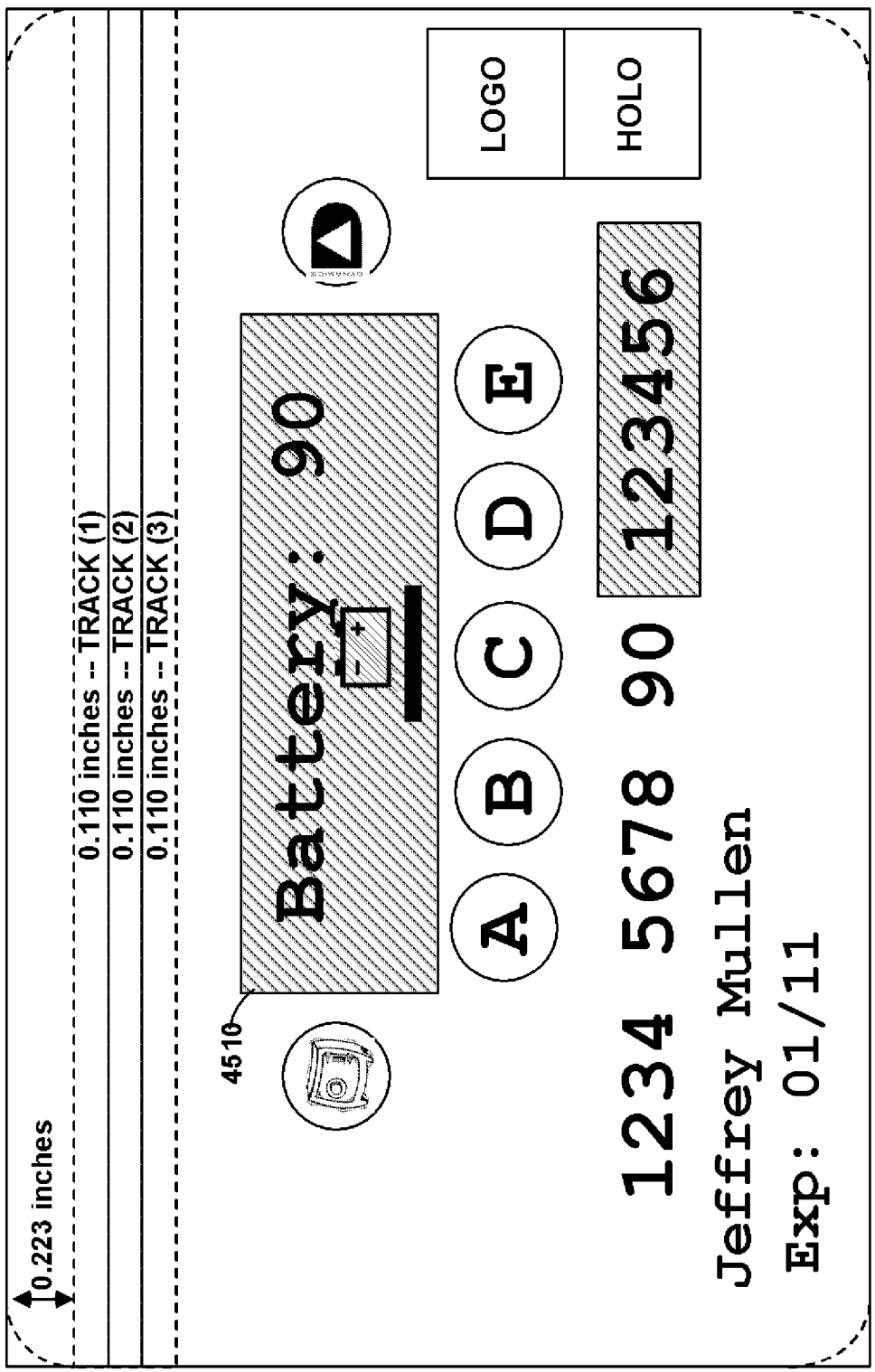

FIG. 45 shows card 4500 that may include display 4510. Display 4510 may include multiple lines of display. Display 4510 may display symbols. Display 4510 may display indicia representative of the activation of a button.

Figure 46:
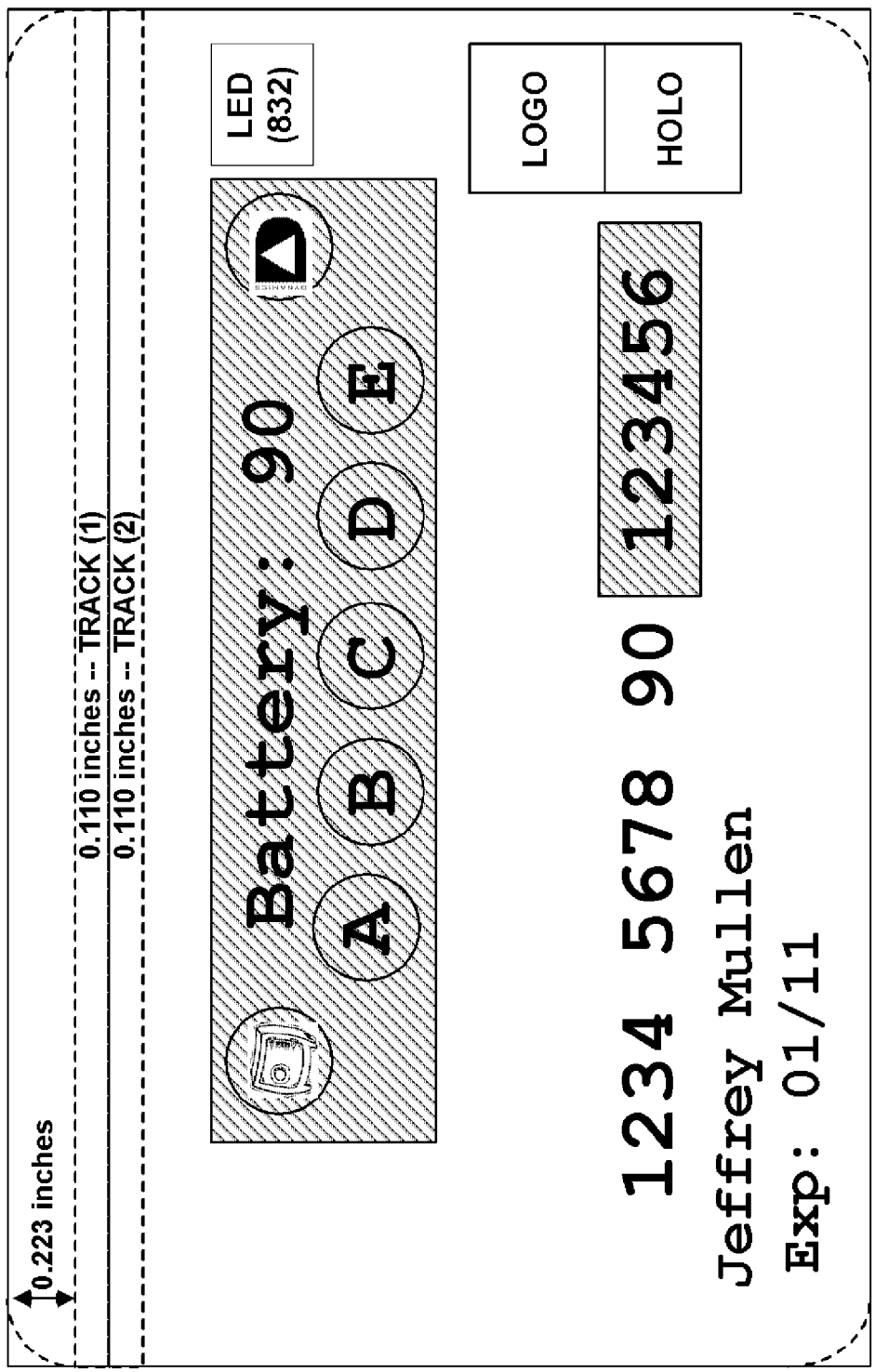

FIG. 46 shows card 4600 that may include a display having touch-sensitive display areas as well as non-touch sensitive display areas.

Figure 47:
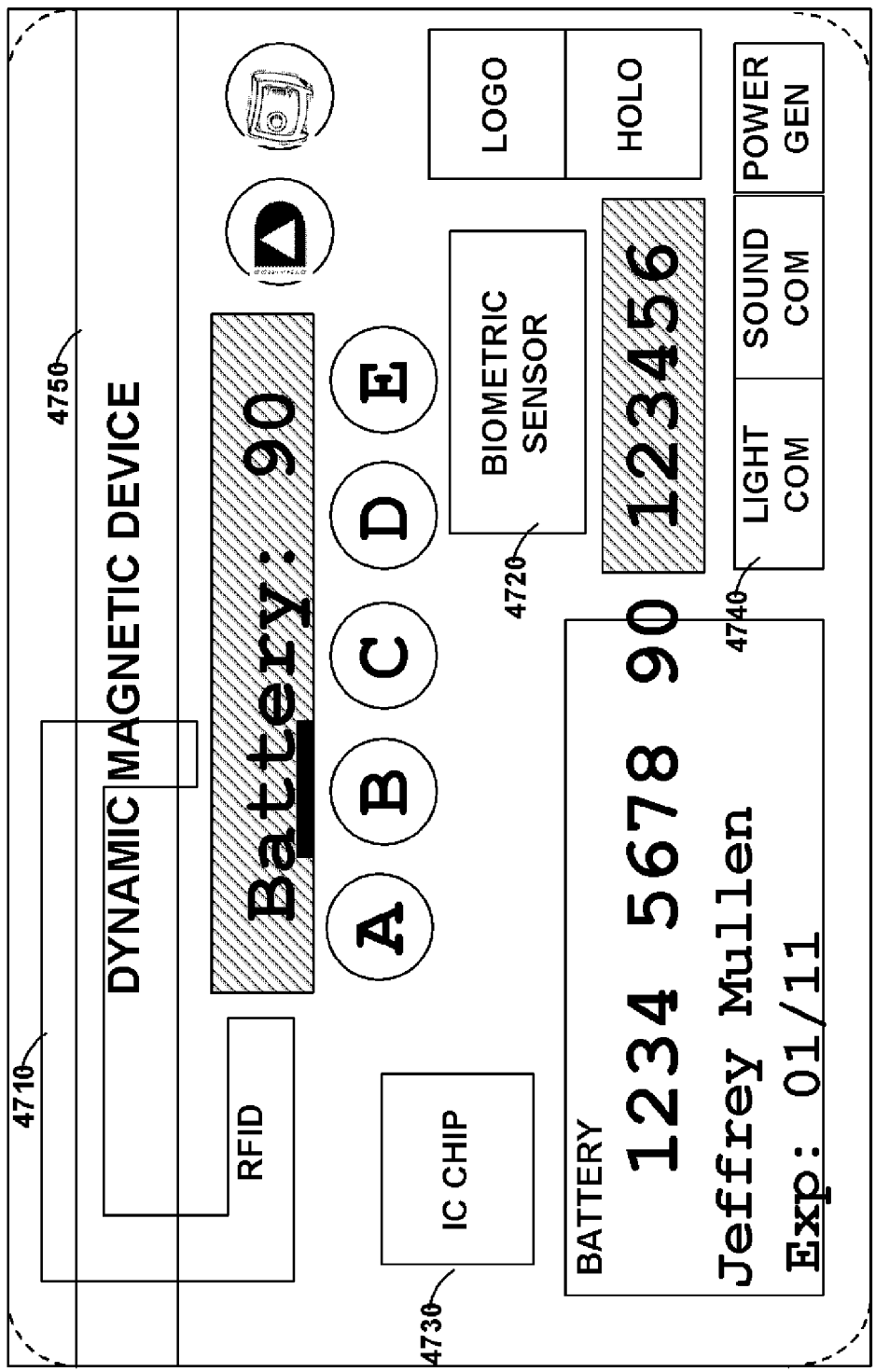

FIG. 47 shows card 4700 that may include any number of components. For example, card 4700 may include RFID antenna 4710. Card 4700 may also include a structure able to communicate dynamic magnetic stripe data (e.g., device 4750). Card 4700 may include IC chip 4730. Card 4700 may include biometric sensor 4720. Biometric sensor 4700 may be, for example, a fingerprint reader (e.g., a partial fingerprint reader) or a retina scanner. Biometric sensor 4700 may be utilized, for example, to unlock a card (e.g., used in lieu of a PIN/PAC). Light transmitter and receiver 4740 may be provided in order to transmit and receive light-based information signals. Card 4700 may include, for example, one or more batteries as well as a processor and memory. A processor may direct an IC chip, any number of magnetic emulators or encoders, and an RFID antenna to communicate information. IC chip 4730 may, alternatively, for example, direct an RFID antenna (e.g., a passive or active RFID antenna) and any number of magnetic emulators or encoder to communicate data. A sound receiver and transmitter may be provided in order for card 4700 to receive information via sound-based signals and send information via sound-based signals.

Card 4700 may also include, for example, power harvesting circuitry. Power harvesting circuitry may be utilized, for example, to repower a battery or provide charge to a capacitor to control a burst of data from an RFID antenna or one or more magnetic emulators and/or encoders. Power harvesting circuitry may include, for example, circuitry for harvesting electromagnetic fields such as fields utilized to power passive RFID antennas. Power harvesting circuitry may also include, for example, a kinetic-to-electrical energy converter that can convert mechanical energy to electrical energy. Alternatively, for example harvesting circuitry may include a thermal-to-electrical energy converter. Alternatively still, for example, harvesting circuitry may include an array of solar cells.

Figure 48:
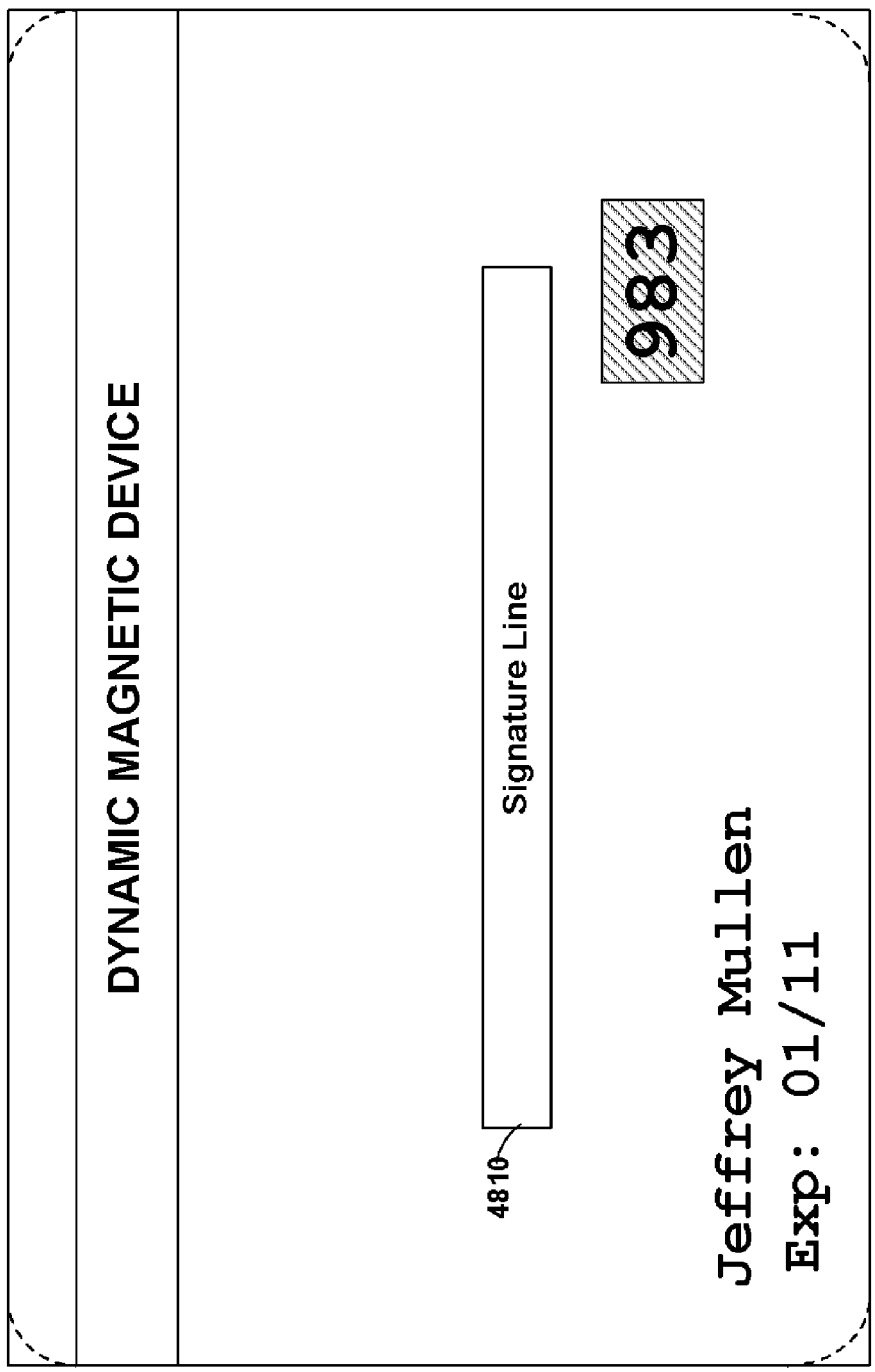

FIG. 48 shows card 4800. Signature-receivable portion 4810 may be provided. A display for a code (e.g., three or four digit code) may also be provided. Portion 4810 and a display for a code may be, for example, provided on the reverse side of any card.

Figure 49:
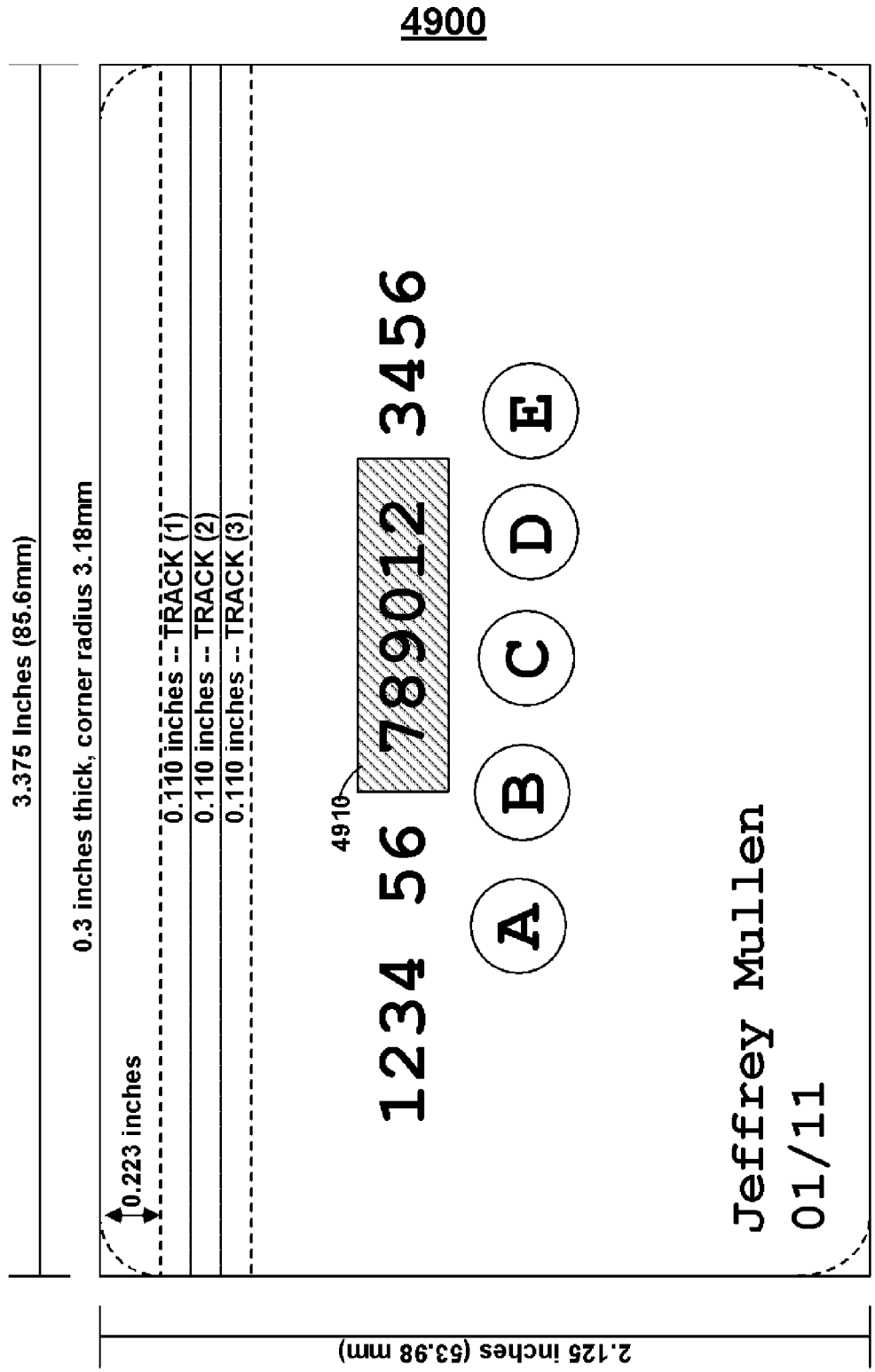

FIG. 49 shows card 4900 that may include a display to display a middle portion of a payment card number.

Figure 50:
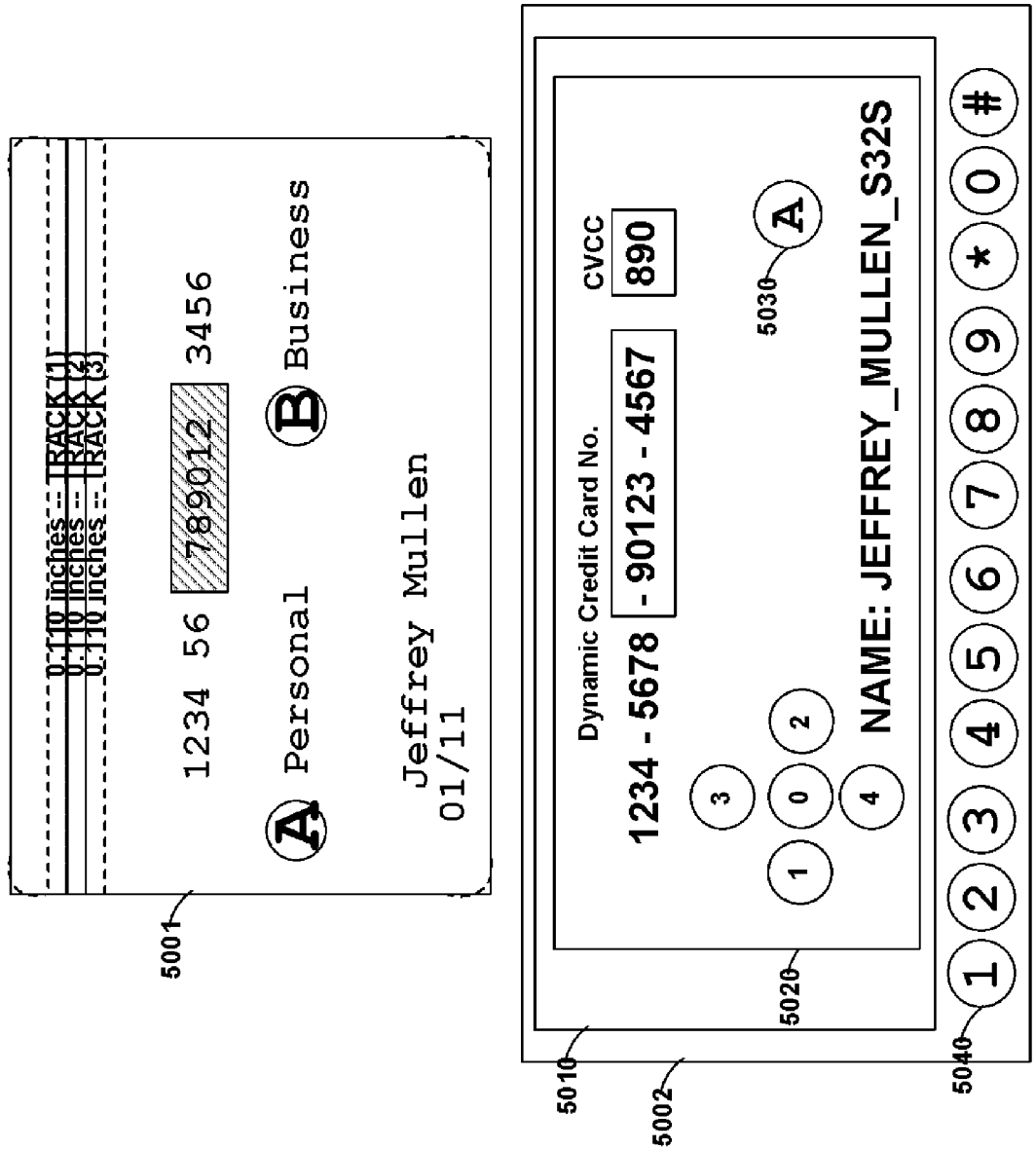
FIG. 50 is an illustrations of a card and a personal electronic device constructed in accordance with the principles of the present invention.

FIG. 50 shows card 5001 that may include a button associated with one account and another button associated with another account.

Persons skilled in the art will appreciate that data may be transferred, such as gift card and/or pre-paid card data, to a card in a variety of ways. For example, a card may be swiped a second time through a magnetic stripe reader that includes a magnetic stripe encoder. A coil on the card may be utilized to receive the information and provide the received information to a processor. In doing so, information may be loaded into the card. Similarly, an IC chip may be utilized to receive data as well as a passive or active RFID. Additionally, one or more microphones may be included to receive audio information that may be representative of data. Accordingly, for example, a user may hold his/her card, or other device, next to a device that is operable to transmit audio via a speaker (e.g., laptop, stationary computer, or mobile telephonic device). The audio information may be discerned by the card and utilized to load information into the card (e.g., a gift card or pre-paid card. An application may also be loaded that enhances the functionality of the card. Such an application may include, for example, a user's medical information such that medical information can be displayed via the card (or other device) during a medical emergency. Accordingly, applications and/or payment cards may be purchased online and a speaker may communicate information to a card. Similarly, the card may include a speaker for transmitting information such that bi-directional communications are established. A light detector may be provided on a card that may receive light pulses indicative of data. Accordingly, for example, a user may hold a card up to a display—such as the screen of a laptop, stationary computer, or mobile phone—and information may be communicated from the display to the card via the light detector. Similarly, a light source may be utilized to communicate information from one device to another. For example, a light source (e.g., LED) may be utilized to communicate information from one card to another. Similarly, a magnetic stripe reader may include a light source. A card may be positioned over the light source such that a light detector of the card is aligned with the light source to receive light. Accordingly, the light of a magnetic stripe reader (or other type of reader) may be utilized to communicate information back to a card. A user may utilize interfaces on the card (e.g., buttons) to initiate a transfer of data from one card to another card or from a device to a card. A variety of types of data may be communicated. For example, money may be communicated from one debit card to another debit card such that payments may occur between the cards. Accordingly, for example, the next time a card is utilized via a reader (e.g., a magnetic stripe reader) information of the transfer may be communicated to a server for processing. Light may be utilized to transfer data from a card to a computer using, for example, a camera (e.g., webcam) on the computer. Sound may be utilized to transfer data from a card to a computer using, for example, a microphone on the computer.

A display may also be utilized as an interface. For example, a display may include a contact and an electronic ink. The electronic ink may change colors in response to, for example, a particular electrical signal being supplied to the contact. A capacitive sensor may be coupled to such a contact, however, such that a user interaction with the contact may be sensed by the capacitive sensor. Accordingly, a card may include a display that can also receive user input. Persons skilled in the art will appreciate that a display may include multiple contacts. For example, a display may include multiple 7-segment (e.g., to display digits) or 11-segment, 14-segment, or 16-segment (e.g., to display alphanumerics) regions where each segment may be coupled to a capacitive sensor.

A biometric sensor may be placed on a card or other device. Such a biometric sensor may be, for example, a fingerprint reader. Accordingly, one or more fingerprints may be stored in the memory of a card and compared to scanned fingerprints. Different fingerprints may activate the card differently (e.g., utilize a different user's payment card info).

Persons skilled in the art will appreciate that a user's payment card number (e.g., credit card or debit card number) does not have to change. A display may hide this payment card number until an appropriate unlocking code is entered into buttons of the card. Similarly, a magnetic emulator may not be provided current until the proper unlocking code is entered—thus keeping magnetic information private and not allowing undesirable readers to read a card. A security code may be displayed on the same or a different display. A button may be provided representative of an online purchase (or a user may utilize buttons to instruct the processor that an online purchase is desirable). For such an online purchase, the credit card number and the security code may be displayed—but the magnetic emulator may not be activated. In doing so, the level of security of the card is increased. Furthermore, for example, a button may be provided representative of in-store purchases (or a user may utilize buttons to instruct the processor that an in-store purchase is desirable). Accordingly, a processor may be signaled that an in-store purchase is desired. A different operation may be associated with different types of purchases (e.g., online or in-store). Accordingly, for example, magnetic emulators may be activated for an in-store environment—but not the displays. Accordingly, for example, a restaurant cashier may not be able to read the credit card number from the card, but may still be able to swipe the card. If a reader is down or a cashier requires reading particular information (e.g., a security code or credit card number information) then controls may be utilized to communicate this information. A record of the types of transactions may be stored and may be communicated in discretionary fields of data within a transmitted data track. Such record information may be utilized, for example, to further increase security and/or introduce a variety of additional functionality.

Different types of cards may be provided on a card. For example, a security ID number and a credit card number may both be provided on the same card. A button may be utilized to allow a user to provide instruction to a processor such that the processor can display (e.g., visually and/or magnetically) the desired information. For example, a user may determine to use one of a variety of payment accounts (e.g., credit and/or debit) for a purchase. An entire payment number (e.g., credit or debit) may be changed and/or hidden visually and/or magnetically. A portion of a payment card number (e.g., credit or debit) may be changed and/or hidden visually and/or magnetically.

Persons skilled in the art will appreciate that a display on the card may display a credit card number that does not change with time (or transaction or button press). Additionally, for example, a magnetic emulator (or multiple magnetic emulators) may magnetically communicate financial data that does not change with time. Such a card may reduce, for example, the effects of physical card theft and card cloning.

Persons skilled in the art will appreciate that any numbers of a credit card number may remain static and/or change either with time or based off a transaction (e.g., by sensing a read-head "swipe"). Additionally, any static and/or dynamic numbers may be displayed via a display or printed on a card. For example, a middle 6 digits of a credit/debit card number may be static and may be displayed on a display. Such a middle 6 digits may be displayed, for example, upon the entry of a correct PIC. Similarly, a magnetic emulator may not communicate information until a correct PIC has been entered by a user. Doing so may, for example, reduce fraud associated with card cloning. Additionally, a receipt may be provided that includes masked credit card numbers except for the last few digits of credit card numbers. Accordingly, displaying a static middle 6 digits of credit card numbers may allow for such a receipt to be provided while still reducing credit card fraud from hiding numbers that are not displayed on such a receipt. Any amount of numbers and/or characters may be displayed through a display. For example, nineteen digits may be displayed as part of a credit/debit numbers and these numbers may also be communicated through one or more magnetic emulation circuits. The entry of particular PICs may provide different results. For example, a first PIC may only display a string of alphanumeric characters. A second PIC may only activate a magnetic emulation circuit to transmit information including that string of alphanumeric characters (or a different string). A third PIC may activate a magnetic emulation circuit and a display. A display and/or magnetic emulation circuit may be turned OFF, for example, upon entry of an incorrect PIC and/or after a period of time has passed since the entry of the PIC and/or after the detection of a particular number of swipes by a read-head detector (e.g., one or two).

Persons skilled in the art will appreciate that a credit/debit card number (or any other information) may remain static until an event occurs and then may become dynamic (e.g., change based on swipes and/or time). For example, a particular PIC may change from a static to a dynamic topology and/or a topology may be changed from static to dynamic after a pre-determined period of time. Additionally a card and/or device may include a wireless receiver and a topology may be changed from a static to a dynamic topology upon, for example, receiving an appropriate signal from the wireless receiver. Accordingly, a validation process may change at a validation server depending upon whether a card is utilizing a static and/or dynamic topology at any given time. Additionally, a static credit/debit card number may be printed on the face of a card and information (e.g., a security code) may be displayed via a display and remain static over time (or with use) or be provided dynamically.

A card or other device (e.g., a mobile telephone) may accept a pre-determined number of consecutive incorrect PICs before locking the card for a period of time or until an appropriate secondary PIC is entered. Accordingly, a user may enter in an incorrect PIC a number of times and then, after a card becomes locked, call a support center for a secondary one-time use PIC. A card may cycle through unlocking PICs based, for example, on time or the number of previous unlock attempts.

FIG. 50 shows personal electronic device 5002 which may be, for example, a portable telephonic device, portable media player, or any type of electronic device. Persons skilled in the art will appreciate that the functionality of a card may be provided on a personal device and displayed through a graphical user interface. Personal electronic device 2000 may include, for example, user inputs 2040 and display 5010. Virtual card 5020 may be displayed on display 5020. Display 5020 may be a touch-sensitive display such that, for example, virtual button 5030 may be provided on virtual card 5020. Persons skilled in the art will appreciate that cards may be provided as virtual cards and a user may interact with such virtual cards in order to provide a variety of functions. Personal electronic device 5002 may communicate to a card reader such as, for example, an RFID reader.

A display may be bi-stable or non bi-stable. A bi-stable display may consume electrical energy to change the information displayed on the bi-stable display but may not consume electrical energy to maintain the display of that information. A non bi-stable display may consume electrical energy to both change and maintain information on the non bi-stable display. A display driving circuit may be provided, for example, for a bi-stable display (or a non bi-stable display). Such a display driving circuit may step-up a supply voltage (e.g., 1-5 volts) to a larger voltage (e.g., 6-15 volts) such that a bi-stable display may change displayed information. A controller (e.g., a processor) may be utilized to control such a display driving circuit. Persons skilled in the art will appreciate that a display may be configured to display numerical data or alphanumerical data. A display may also be configured to display other indicia (e.g., the image of a battery and its remaining life).

A magnetic stripe reader may, for example, determine information on a magnetic stripe by detecting the frequency of changes in magnetic fields (e.g., flux transversals). A particular frequency of flux transversals may correlate to, for example, a particular information state (e.g., a logic "1" or a logic "0"). Accordingly, for example, a magnetic emulator may change the direction of an electromagnetic field at particular frequencies in order to communicate a different state of information (e.g., a logic "1" or a logic "0").

Persons skilled in the art will appreciate that a magnetic emulator may electromagnetically communicate information serially by changing the magnitude of an electromagnetic field with respect to time. As such, for example, a current in a single direction may be provided through a magnetic emulator in order for that magnetic emulator to generate an electromagnetic field of a single direction and a particular magnitude. The current may then be removed from the magnetic emulator such that, for example, the electromagnetic field is removed. The creation of a presence of an electromagnetic field, and the removal of that electromagnetic field, may be utilized to communicate information to, for example, a magnetic stripe reader. A magnetic stripe reader may be configured to read, for example, the change in flux versus time and may associate an increase in an electromagnetic field (e.g., creation of a field) as one flux transversal and a decrease (e.g., removal of a field) as another transversal. In doing so, for example, driving circuitry (not shown) may be provided which, in turn, controls when current is provided to a magnetic emulator. The timing of magnetic flux transversals, as determined by a magnetic stripe reader, may be utilized by that reader to determine whether a logic one ("1") or logic zero ("0") was communicated. Accordingly, a driving circuit may change the frequency of when current is supplied and removed from a magnetic emulator in order to communicate a logic one ("1") or a logic zero ("0").

A driving circuit may, for example, change the direction of current supplied to a magnetic emulator to increase the amount of change in an electromagnetic field magnitude for a period of time. In doing so, for example, a magnetic stripe reader may more easily be able to discern overall changes in an electromagnetic field and, as such, may more easily be able to discern information. As such, for example, a driving circuit may increase the magnitude of an electromagnetic field by providing negative current, decrease the amount of negative current until no current is provided and provide an increasing positive current in order to provide a large swing in the magnitude of an electromagnetic field. Similarly, a driving circuit may switch from providing one amount of negative current (or positive current) to one amount of positive current (or negative current).

Persons skilled in the art will appreciate that a string of a particular bit of data (e.g., a string of logic zeros "0s") may be communicated before as well as after information is communicated through a magnetic emulator. A magnetic stripe reader may utilize such data, for example, to determine base timing information such that the magnetic stripe reader has a timing reference that the reader can utilize to assist in determining timing changes of perceived flux transversals. Accordingly, for example, a magnetic emulator may send data at different overall frequencies and a magnetic stripe reader may be able to reconfigure itself to receive data at such overall frequencies. Information may be encoded using, for example, Frequency/Double Frequency (F2F) encoding such that magnetic stripe readers may perform, F2F decoding.

A processor may control one or more emulators by, for example, controlling the direction of the current supplied through one or more segments of an emulator. By changing the direction of current through a region, for example, the direction of an electromagnetic field may be changed. Similarly, a processor may control one or more emulators by, for example, controlling the change in magnitude of current supplied through one or more segments of an emulator. As such, for example, a processor may increase the magnitude of current as well as decrease the magnitude of current supplied through an emulator. A processor may control the timing of such increases and decreases in current such that a magnetic emulator may, for example, communicate F2F encoded information.

Persons skilled in the art will appreciate that a dynamic magnetic communications device (e.g., a magnetic emulator or magnetic encoder) may be fabricated, either completely or partially, in silicon and provided as a silicon-based chip. Other circuitry (e.g., driving circuitry) may also be fabricated on such a silicon-based chip. A processor, such as a processor for controlling a magnetic communications device, may be, for example, a programmable processor having on-board programmable non-volatile memory (e.g., FLASH memory), volatile memory (e.g., RAM), as well as a cache. Firmware as well as payment information (e.g., dynamic numbers) may be, for example, communicated from a programming device to a processor's on-board programmable non-volatile memory (e.g., a FLASH memory) such that a card may provide a variety of functionalities. Such a processor may also have one or more power-saving operating modes, in which each operating mode turns OFF a different set of circuitry to provide different levels of power consumption. One or more power-savings modes may turn OFF, for example, one or more clocking circuitry provided on a processor. An Application-Specific Integrated Circuit (ASIC) may also be included in a card or other device to provide, for example, processing, dynamic magnetic communications, as well as driving capabilities.

Persons skilled in the art will also appreciate that the present invention is not limited to only the embodiments described. Instead, the present invention more generally involves dynamic information. Persons skilled in the art will also appreciate that the apparatus of the present invention may be implemented in other ways then those described herein. All such modifications are within the scope of the present invention, which is limited only by the claims that follow.

What is claimed is:

1. A payment card comprising:
   a magnetic emulator for communicating data in serial;
   a button located over said magnetic emulator;
   a bi-stable display; and
   a non bi-stable display.

2. The payment card of claim 1, further comprising a read-head detector operable to detect a read-head of a magnetic stripe reader.

3. The payment card of claim 1, further comprising a second button, wherein said second button is not located over said magnetic emulator.

4. The payment card of claim 1, further comprising a processor.

5. A payment card comprising:
   a magnetic emulator for communicating data in serial;
   a button covering at least a portion of said magnetic emulator;
   a bi-stable display; and
   a non bi-stable display.

6. The payment card of claim 1, further comprising a processor, an IC chip, and an RFID.

7. The payment card of claim 1, further comprising a memory, wherein payment data is stored on said memory, at least a portion of said payment data is communicated through said magnetic emulator, and at least a portion of said communicated data is displayed on said bi-stable display.

8. The payment card of claim 1, further comprising a memory, wherein payment data is stored on said memory, at least a portion of said payment data is communicated through said magnetic emulator, and at least a portion of said communicated data is displayed on said non bi-stable display.

9. The payment card of claim 1, further comprising a memory, wherein payment data is stored on said memory, at least a portion of said payment data is communicated through said magnetic emulator, and at least a first portion of said communicated data is displayed on said bi-stable display and at least a second portion of said communicated data is displayed on said non bi-stable display.

10. The payment card of claim 1, further comprising;
    a first surface; and
    a memory, wherein a payment card number is stored in said memory, at least a portion of said payment card number is printed on said first surface, and said bi-stable display is viewable from said first surface.

11. The payment card of claim 1, further comprising a first surface, wherein said bi-stable and non bi-stable display are viewable from said first surface.

12. The payment card of claim 1, further comprising a memory, wherein a code is stored in said memory for, at least in part, display on said non bi-stable display.

13. The payment card of claim 1, further comprising a memory, wherein a portion of a payment card number is stored in said memory for, at least in part, display on said bi-stable display.

14. The payment card of claim 1, further comprising a source of light.

15. The payment card of claim 1, further comprising a second button, wherein said non bi-stable display is located within the proximity of said second button.

16. The payment card of claim 1, further comprising a second button, wherein said bi-stable display is located within the proximity of said second button.

17. A battery-powered card comprising: a magnetic emulator for serially communicating magnetic stripe data;
    a button covering at least a portion of said magnetic emulator;
    a bi-stable display; and
    a non bi-stable display.

18. The battery-powered card of claim 17, further comprising a read-head detector operable to detect a read-head of a magnetic stripe reader.

19. The battery-powered card of claim 17, further comprising a second button, wherein said second button is not located over said magnetic emulator.

20. The battery-powered card of claim 17, further comprising a memory, wherein data is stored on said memory, at least a portion of said data is communicated through said magnetic emulator, and at least a first portion of said communicated data is displayed on said bi-stable display and at least a second portion of said communicated data is displayed on said non bi-stable display.

* * * * *